(12) United States Patent
Amberg et al.

(10) Patent No.: US 8,921,406 B2
(45) Date of Patent: Dec. 30, 2014

(54) 5-RING HETEROAROMATIC COMPOUNDS AND THEIR USE AS BINDING PARTNERS FOR 5-HT5 RECEPTORS

(75) Inventors: Wilhelm Amberg, Mannheim (DE); Astrid Netz, Mannheim (DE); Andreas Kling, Mannheim (DE); Michael Ochse, Weisenheim am Barg (DE); Udo Lange, Berlin (DE); Andreas Haupt, Schweizingen (DE); Francisco Javier Garcia-Ladona, Kandel (DE); Wolfgang Wernet, Neustadl (DE); Alfred Hahn, legal representative, Mannheim (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 1932 days.

(21) Appl. No.: 11/990,731

(22) PCT Filed: Aug. 21, 2006

(86) PCT No.: PCT/EP2006/008223
§ 371 (c)(1),
(2), (4) Date: Jun. 15, 2010

(87) PCT Pub. No.: WO2007/022947
PCT Pub. Date: Mar. 1, 2007

(65) Prior Publication Data
US 2011/0207788 A1    Aug. 25, 2011

Related U.S. Application Data

(60) Provisional application No. 60/711,014, filed on Aug. 24, 2005.

(30) Foreign Application Priority Data

Aug. 21, 2005  (DE) .......................... 10 2005 040 600
Feb. 9, 2006   (DE) .......................... 10 2006 005 917

(51) Int. Cl.
| | |
|---|---|
| *A61K 31/415* | (2006.01) |
| *A61K 31/4168* | (2006.01) |
| *A61K 31/4192* | (2006.01) |
| *A61K 31/4196* | (2006.01) |
| *C07D 233/88* | (2006.01) |
| *C07D 231/38* | (2006.01) |
| *C07D 249/04* | (2006.01) |
| *C07D 249/14* | (2006.01) |
| *C07D 405/04* | (2006.01) |
| *C07D 409/04* | (2006.01) |
| *C07D 233/70* | (2006.01) |

(52) U.S. Cl.
CPC ............ *C07D 233/70* (2013.01); *C07D 405/04* (2013.01); *C07D 233/88* (2013.01); *C07D 409/04* (2013.01)

USPC ..... 514/398; 548/255; 548/264.8; 548/326.5; 514/383; 514/407

(58) Field of Classification Search
USPC ............ 548/326.5, 255, 264.8; 514/398, 383, 514/407
See application file for complete search history.

(56) References Cited

U.S. PATENT DOCUMENTS

| 4,957,935 | A | 9/1990 | Inamori et al. | |
|---|---|---|---|---|
| 6,303,638 | B1 * | 10/2001 | Latli et al. ...................... | 514/340 |
| 6,352,985 | B1 | 3/2002 | Yamasaki et al. | |
| 6,750,221 | B1 | 6/2004 | Garcia-Ladona et al. | |
| 2005/0245592 | A1 | 11/2005 | Suzuki et al. | |
| 2007/0066606 | A1 | 3/2007 | Stahle et al. | |

FOREIGN PATENT DOCUMENTS

| CA | 2359360 | 7/2000 |
|---|---|---|
| EP | 285896 | 3/1988 |
| EP | 285893 | 10/1988 |
| EP | 0 545 845 | 6/1993 |
| EP | 1 293 503 | 5/2001 |
| EP | 1 426 451 | 6/2004 |
| JP | 200209062 | 1/2002 |
| JP | 2002275165 | 9/2002 |
| WO | WO 92/15577 | 9/1992 |
| WO | WO 97/24334 | 7/1997 |
| WO | WO 97/36875 | 10/1997 |
| WO | WO 99/62908 | 12/1999 |
| WO | WO 00/31067 | 6/2000 |
| WO | WO 00/41472 | 7/2000 |
| WO | WO 00/41696 | 7/2000 |
| WO | WO 01/81326 | 11/2001 |
| WO | WO 01/87855 | 11/2001 |
| WO | WO 01/98276 | 12/2001 |
| WO | 02/004424 | 1/2002 |
| WO | WO 02/053158 | 7/2002 |
| WO | WO 02/088094 | 7/2002 |
| WO | WO02/072549 | 9/2002 |
| WO | WO02/076960 | 10/2002 |
| WO | 2005/028448 | 3/2005 |

OTHER PUBLICATIONS

Molina et al. J.Org.Chem. (1999), vol. 64, pp. 2540-2544.*

(Continued)

*Primary Examiner* — Kamal Saeed
*Assistant Examiner* — Janet L Coppins
(74) *Attorney, Agent, or Firm* — Lisa V. Mueller; Michael Best & Friedrich LLP

(57) ABSTRACT

The invention relates to 5-ring heteroaromatic compounds of general formula (I), their use for the treatment and/or prevention of diseases, and medicaments containing same.

23 Claims, No Drawings

(56) References Cited

OTHER PUBLICATIONS

Moline et al. J.Org.Chem. (1999), vol. 64, pp. 2540-2544.*
Plassat et al., The EMBO Journal, "The Mouse 5HT5 Receptor Reveals a Remarkable Heterogencity Within the 5HT1D Receptor Family", 1992 vol. 11 No. 13, pp. 4479-4786.
Carson et al., GLIA, "The 5-HT5A Serotonin Receptor is Expressed Predominantly by Astrocytes in Which it InhibitscAMP Accumulation of Reactive Astrocytes", 1996, pp. 317-326.
Boess et al., Neuropharmacology, "Review Molecular Biology of 5-HT Receptors", vol. 33, No. 3/4, (1994) pp. 275-317.
Kennet G.A., 5-HT Receptors and Their Ligands; Serotonin Receptors and Their Function, TOCRIS Review (http://www.tocris.com/serotonin.htm), May 1997.
Peroutka S.J., 1994 Molecular Biology of Serotonin (5-HT) Receptors, Synapse 18, 241-260.
Nelson, D.L., Current Drug Targets—CNS & Neurological Disorders 2004, , Issue 1, 53-58.
Erlander et al., Proc. Natl. Acad. Sci. USA, "Two Members of a Distinct Subfamily of 5-Hydroxytryptamine Receptors Differentially Expressed in Rat Brain", vol. 90, pp. 3452-3456 (1993).
Oliver et al., Brain Research, "Localization of 5-ht5A Receptor-Like Innumoreactivity in the Rat Brain", 867 (2000) pp. 131-142.
Pasqualetti et al., Molecular Brain Research, "Distribution of the 5-HT5A Serotonin Receptor mRNA in the Human Brain", 56 (1998), pp. 1-8.
Pilyugin et al., Russian Journal of General Chemistry, "Acyl Derivatives of 2-Aminobenzimidazole and Their Fungicide Activity", vol. 74, No. 5, (2004), pp. 804-810.
Kienzle, F. et al., Eur. J. Med. Chem.—Chim Ther., "1,5-Dihydroimidazoquinazolinones as Blood Platelets Aggregation Inhibitors", 1982-17, No. 6, pp. 547-556.
Nakamura et al., Heterocytes, "1-Methyl-3-Trimethylsilyparabanic Acid as an Effective Reagent for the Preparation of N-Substituted (1-Methyl-2,5-Dioxo-1,2,5H-Imidazolin-4-yl)-Amines and its Application to the Total Synthesis of Isonaamidines A and C, Antitumor Imidazole Alkaloids", vol. 60, No. 3, (2003), pp. 583-598.
Cross et al., Journal of Natural Products, "New and Biologically Active Imidazole Alkatoids from Two Sponges of the Genus *Leucetta*", 65(8)m (2002), pp. 1190-1193.
Crews et al., Journal of Natural Products, "Structures and Total Synthesis of 2-Aminoimidazoles from a Notodoris Nudibranch", vol. 54, No. 6, (1991), pp. 1509-1515.
Moline et al., Journal of Organic Chemistry, "Synthesis of Marine Alkatoids Isonaamine A, Dorimidazole A, and Preclathridine A, Iminophophorane-Mediated preparation of 2-Amino 1,4-distributed Imidazoles from a-Azido Esters", 64(7), (1999), pp. 2540-2544.
Carmely et al., Tetrahedron, "2-Amino Imidazole Alkaloids from the Marine Sponge Leucetta Chagosensis", vol. 45, No. 7, (1989), pp. 2193-2200.
Compte Rendues des Seances de l'Academie des Sciences, Serie C: Sciences Chimiques, 287(4), (1978), pp. 121-123.
Davidson, George Thieme Publishers, "A Preparation of 3-Amino-4,5-diaryl-1,2,4-triazoles", May 11979, pp. 359-361.
Davidson et al., Chemistry and Industry, "Benzyl Derivatives of 3-Amino-5-Phenyl-1,2,4-Triazole", Feb. 4, 1978, pp. 92-94.

* cited by examiner

5-RING HETEROAROMATIC COMPOUNDS AND THEIR USE AS BINDING PARTNERS FOR 5-HT5 RECEPTORS

CROSS-REFERENCE TO RELATED APPLICATIONS

This is a U.S. national stage entry of International Patent Application No. PCT/EP2006/008223, filed on Aug. 21, 2006, which claims priority to German Patent Application No. 102006005917.4, filed on Feb. 9, 2006, U.S. Patent Application No. 60/711,014, filed on Aug. 24, 2005, and German Patent Application No. 102005040600.9, filed on Aug. 21, 2005, the entire contents of all of which are fully incorporated herein by reference.

FIELD OF THE INVENTION

The present invention relates to 5-HT5 receptor ligands, methods for preparing such compounds and intermediate products for preparation of same, and pharmaceutical preparations and treatment methods for diseases which are modulated by 5-HT5 receptor activity, in particular for the treatment of neurodegenerative and neuropsychiatric disorders and the associated signs, symptoms, and dysfunctions.

BACKGROUND OF THE INVENTION

The neurotransmitter serotonin (5-hydroxytryptamine or "5-HT") is the subject of intensive research; anomalies in the processing of serotonin are a component of various disease profiles. Serotonin acts in the cardiovascular, gastrointestinal, and central nervous systems by binding to various types of 5-HT receptors. At least seven different receptor classes mediate the physiological activities of serotonin. These receptor classes are designated as 5-HT1, 5-HT2, 5-HT3, 5-HT4, 5-HT5, 5-HT6, and 5-HT7 according to an internationally recognized classification system. Most of these classes include further distinguishable receptor subtypes; thus, the 5-HT1 class includes receptors which in turn may be divided into at least five subclasses, designated 5-HT1A, 5-HT1B, 5-HT1C, 5-HT1D, and 5-HT1E (Boess, Martin; Neuropharmacology 33: 275-317 (1994)).

The properties, function, and pharmacology of these receptor subtypes have been summarized, for example, by: (a) Kennet G. A., "Serotonin Receptors and Their Function," TOCRIS Review (http://www.tocris.com/serotonin.htm), published May 1997; and (b) Peroutka, S. J., 1994, "Molecular Biology of Serotonin (5-HT) Receptors," Synapse 18, 241-260 and Current Drug Targets—CNS & Neurological Disorders 2004, 3, Issue 1.

The 5-HT5 class was first described by Plassat et al., The EMBO Journal, Vol. 11, No. 13, pp. 4779-4786 (1992). A distinction is made between 5-HT5A and 5-HT5B receptors (Erlander et al., Proc. Natl. Acad. Sci. USA 90:3452-3456 (1993). 5-HT5 receptors belong to the family of G protein-coupled receptors, and are negatively coupled to adenylyl cyclase. 5-HT5 receptors have been cloned using mouse, guinea pig, rat, and human cDNA. Despite a high interspecies homology, there are only slight sequence homologies between 5-HT5 receptors and other 5-HT receptors.

5-HT5 receptors may be localized in the hippocampus, cerebellum, hypothalamus, thalamus, and striatum, cortex, for example, using molecular biological techniques. Immunohistochemical methods have shown that 5-HT5 receptors of neurons are expressed in various regions of the brain (Oliver et al., Brain Res. 2000, 867, 131-142; Pasqualetti et al., Mol. Brain. Res. 1998, 56, 1-8). On the one hand these 5-HT5 receptors may directly or indirectly modulate important functions of the brain, and on the other hand may also participate in mechanisms involved in neuropathological, neurodegenerative, and neuropsychiatric diseases. 5-HT5 receptors have also been localized in astrocytes (Carson et al., GLIA 17:317-326 (1996)). Reactive astrocytes have been observed in conjunction with reactive gliosis for a number of pathological brain changes and neuropsychiatric diseases. In vitro tests of cultivated astrocytes have shown 5-HT5 receptor-mediated responses. For this reason it is suspected, on the one hand, that 5-HT5 receptors are involved in healing processes of the brain subsequent to disorders, but on the other hand it cannot be ruled out that they also contribute to the origin or even proliferation of damage.

5-HT5 receptors show a high affinity for various antidepressants and antipsychotic agents. Previous studies indicate that 5-HT5 receptors play a role in the following disease profiles:

Psychosis, depression, chronic schizophrenia, other psychotic conditions, anxiety, bipolar disorders, dementia, in particular Alzheimer's dementia, demyelinating diseases, in particular multiple sclerosis, and ischemia, stroke, and migraines.

The use of 5-HT5 receptor ligands for the general treatment of migraines and other cerebrovascular diseases is described in WO 00/041472, and for the treatment of neurodegenerative and neuropsychiatric diseases, in WO 00/041696.

Imidazole compounds have not been used heretofore as 5-HT5 ligands.

Substituted imidazoles, triazoles, and pyrazoles are known, for example, as kinase inhibitors, as inhibitors of various phosphodiesterase subtypes, as angiotensin receptor antagonists, and as polymerase inhibitors.

WO 2005028448 describes benzyl-substituted benzimidazoles as tyrosine kinase inhibitors. EP 545845 (U.S. Pat. No. 5,314,903) describes the preparation and use of substituted N-alkylphenylaminobenzimidazoles as calcium channel blockers. WO 9724334 (U.S. Pat. No. 6,352,985, U.S. Pat. No. 6,166,219, EP 882718) describes "carbonyl"-substituted N-alkylphenylalkylaminobenzimidazoles and their use as PDE5 inhibitors. EP 111993 describes the preparation of "carbonyl"-substituted N-alkylaminobenzimidazoles and their use as antiviral compounds. WO 9855120 describes benzoyl-substituted N-alkylaminobenzimidazoles and their use as antiviral compounds, and WO 9962908 describes, among other things, benzimidazole derivatives and their use as cell adhesion inhibitors. WO 200272549 and WO 200276960 relate to functionalized indoles and benzimidazoles and their use as kinase inhibitors. Lastly, benzoyl-substituted benzimidazoles are described in Russian Journal of General Chemistry 2004, 74 (5), 738-743. WO 200288094 describes the preparation of N,N'-disubstituted iminobenzimidazoles and their use as thrombin inhibitors, and WO 200253158 describes, among other things, the preparation and use of N,N'-disubstituted imidazolium compounds for the treatment of glaucoma.

WO 2001081326 describes 5-ring heteroaromatic compounds having phenethyl side chains as modulators of the α4β2$^1$ receptor. WO 2001098276 and WO 2000031067 relate to the use of imidazoles as hair colorants, and pyridyl-substituted imidazoles are described in U.S. Pat. No. 6,303,638. WO 9215577 describes imidazole toluoyl pyrroles as angiotensin receptor antagonists. Imidazolones as platelet aggregation inhibitors are described in Journal of Medicinal Chemistry 1982, 17 (6), 547-556. Imidazoles as intermediate products are described in WO 9736875. The activity and synthesis of imidazoles in natural substances are described in Heterocycles 2003, 60 (3), 583-598, Journal of Natural Products 2002, 65 (8), 1190-1193 and 1991, 54 (6), 1509-1515, Journal of Organic Chemistry 1999, 64 (7), 2540-2544, and Tetrahedron 1989, 45 (7), 2193-2200.

[1] Translator's note: Assumed for "□4□2" in the source.

Benzyl-substituted aminotriazoles for the treatment of autoimmune diseases are described in JP 2002275165, and the use of phenyl-substituted triazoles as insecticides and glycine transporters is described in JP 02091062, EP 285893, and WO 2001087855.

Synthesis examples for phenyl-substituted triazoles are found in Compte Rendues des Seances de l'Academie des Sciences, Serie C: Sciences Chimiques 1978, 287 (4), 121-123, Synthesis 1979, (5), 359-361, and Chemistry & Industry, 1978, (3), 92-94, WO 2002004424 describes pyrazoles and their use in the treatment of HIV infections.

SUMMARY OF THE INVENTION

The object of the present invention is to provide compounds which modulate the function of 5-HT5 receptors.

The present invention relates to compounds which modulate the function of 5-HT5 receptors and thus enable the treatment of neuropathological, neuropsychiatric, and neurodegenerative disorders. The invention further relates to pharmaceutical preparations containing these compounds, and the use of these compounds and preparations for the treatment of diseases in which the 5-HT5 receptor is involved.

According to one aspect of the present invention, at least one 5-ring heteroaromatic compound of general formula I

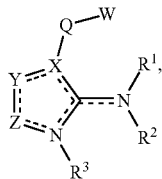

I and/or corresponding enantiomeric, diastereomeric, and/or tautomeric forms thereof, and/or pharmaceutically acceptable salts thereof, and/or active substance precursors ("prodrugs") thereof, are prepared, wherein the stated radicals have the following definitions:

W: is a radical of general formula W1 or W2

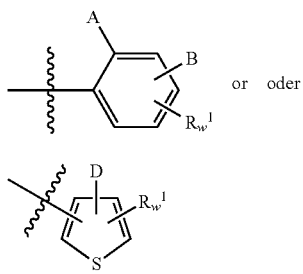

wherein

A: is $NO_2$, $NH_2$, CN, $CF_3$, $OCF_3$, $CHF_2$, $OCHF_2$, COOH, $O-CH_2-COOH$, halogen, SH, or in each case optionally substituted $O-C_1-C_6$ alkyl, $S-C_1-C_6$ alkyl, $-O-CO-C_1-C_6$ alkyl, $-O-CO$ aryl, $-O-CO$ hetaryl, $-O-COO-C_1-C_6$ alkyl, or in each case optionally substituted $C_1-C_6$ alkyl, $C_2-C_6$ alkenyl, $C_2-C_6$ alkynyl, $C_3-C_7$ cycloalkyl, $C_1-C_4$ alkylene-$C_3-C_7$ cycloalkyl, $C_1-C_4$ alkylene-heterocycloalkyl, aryl, hetaryl, heterocycloalkyl, $C_1-C_4$ alkylene-hetaryl, or $C_1-C_4$ alkylene-aryl, or in each case optionally substituted $O-R_A^1$, $CO-R_A^1$, $S-R_A^1$, $SO-R_A^1$, $CO-O-R_A^1$, $NR_A^4-CO-O-R_A^1$, $O-CH_2-COO-R_A^1$, $NR_A^2R_A^3$, $CONH_2$, $SO_2NH_2$, $NR_A^4-CO-R_A^1$, $SO_2-R_A^1$, $NR_A^4-SO_2-R_A^1$, $SO_2-NR_A^2R_A^3$, or $CO-NR_A^2R_A^3$;

$R_A^1$: is in each case optionally substituted $C_1-C_6$ alkyl, $C_2-C_6$ alkenyl, $C_2-C_6$ alkynyl, $C_3-C_7$ cycloalkyl, $C_1-C_4$ alkylene-$C_3-C_7$ cycloalkyl, $C_1-C_4$ alkylene-heterocycloalkyl, aryl, hetaryl, heterocycloalkyl, $C_1-C_4$ alkylene-aryl, $C_2-C_6$ alkenylene-aryl, $C_1-C_6$ alkylene-hetaryl;

$R_A^2$: is hydrogen, or
in each case optionally substituted $C_1-C_6$ alkyl, $C_2-C_6$ alkenyl, $C_2-C_6$ alkynyl, $C_1-C_4$ alkylene-$C_3-C_7$ cycloalkyl, $C_1-C_4$ alkylene-heterocycloalkyl, aryl, hetaryl, heterocycloalkyl, $C_1-C_4$ alkylene-aryl, $C_1-C_4$ alkylene-hetaryl, $C_1-C_6$ alkylene-O-$C_1-C_6$ alkyl, CO-$C_1-C_6$ alkyl, CO-aryl, CO-hetaryl, $C_1-C_4$ alkylene-aryl, CO-$C_1-C_4$ alkylene-hetaryl, CO-O-$C_1-C_6$ alkyl, CO-O aryl, CO-O-$C_1-C_4$ alkylene-aryl, CO-O-hetaryl, CO-O-$C_1-C_4$ alkylene-hetaryl, $SO_2$-$C_1-C_6$ alkyl, $SO_2$-aryl, $SO_2$-hetaryl, $SO_2$-$C_1-C_4$ alkylene-aryl, or $SO_2$-$C_1-C_4$ alkylene-hetaryl;

$R_A^3$: is in each case optionally substituted $C_1-C_6$ alkyl, $C_2-C_6$ alkenyl, $C_2-C_6$ alkynyl, $C_1-C_4$ alkylene-$C_3-C_7$ cycloalkyl, $C_1-C_4$ alkylene-heterocycloalkyl, aryl, hetaryl, heterocycloalkyl, $C_1-C_4$ alkylene-aryl, $C_1-C_4$ alkylene-hetaryl, $C_1-C_6$ alkylene-O-$C_1-C_6$ alkyl, CO-$C_1-C_6$ alkyl, CO-aryl, CO-hetaryl, CO-$C_1-C_4$ alkylene-aryl, CO-$C_1-C_4$ alkylene-hetaryl, CO-O-$C_1-C_6$ alkyl, CO-O-aryl, CO-O-$C_1-C_4$ alkylene-aryl, CO-O-hetaryl, CO-O-$C_1-C_4$ alkylene-hetaryl, $SO_2$-$C_1-C_6$ alkyl, $SO_2$-aryl, $SO_2$-hetaryl, $SO_2$-$C_1-C_4$ alkylene-aryl, or $SO_2$-$C_1-C_4$ alkylene-hetaryl;

or the radicals $R_A^2$ and $R_A^3$ together with the nitrogen form a 3- to 7-membered saturated or aromatic heterocycle which is optionally substituted in each case, which may contain one, two, or three further heteroatoms, which may be different or the same, from the group O, N, S; wherein two radicals substituted on this heterocycle together may optionally form a 3- to 7-membered anellated, saturated, unsaturated, or aromatic carbocycle or heterocycle, wherein the heterocycle may contain up to three heteroatoms O, N, S which may be different or the same, and wherein the cyclic compound thus formed may optionally be substituted, or a further 3- to 7-membered, optionally substituted cyclic compound may be condensed thereon;

$R_A^4$: is hydrogen, or
in each case optionally substituted $C_1-C_6$ alkyl, $C_2-C_6$ alkenyl, $C_2-C_{12}$ alkynyl, $C_3-C_7$ cycloalkyl, aryl, $C_1-C_4$ alkylene-aryl, $C_1-C_6$ alkylene-O-$C_1-C_6$ alkyl, hetaryl;

B: is hydrogen, or is defined as for radical A, independent of radical A, or two of the radicals A, B, or $R_w^1$ in each case independently form, together with the attached C atoms, a 3- to 7-membered, saturated, unsaturated, or aromatic carbocycle which is optionally substituted in each case, or a 3- to 7-membered saturated, unsaturated, or aromatic heterocycle which in each case is optionally substituted and which may contain one, two, or three further heteroatoms, which may be different or the same, selected from the group comprising O, N, and S, wherein in each case two radicals substituted on this carbocycle or heterocycle together may optionally form a 3- to 7-membered anellated, saturated, unsaturated, or aromatic carbocycle or heterocycle, wherein the heterocycle may contain up to three heteroatoms O, N, S which may be different or the same, and wherein the cyclic compound that is formed may optionally be substituted;

$R_w^1$: is hydrogen, OH, halogen, $NO_2$, $NH_2$, CN, $CF_3$, $CHF_2$, $CH_2F$, $OCF_3$, $OCHF_2$, $OCH_2F$, or
in each case optionally substituted $C_1$-$C_6$ alkyl, $C_3$-$C_7$ cycloalkyl, $C_1$-$C_6$ alkylene-O—$C_1$-$C_6$ alkyl, $C_1$-$C_6$ thioalkyl, aryl, hetaryl, O—$C_1$-$C_6$ alkyl, O-benzyl, $C_1$-$C_6$ alkylamino, $C_1$-$C_6$ dialkylamino, pyrrolidinyl, piperidinyl, morpholinyl, CO—$C_1$-$C_6$ alkyl, $SO_2$—$C_1$-$C_6$ alkyl, CO-aryl, $SO_2$-aryl, CO—$C_1$-$C_4$ alkylene-aryl, $SO_2$—$C_1$-$C_4$ alkylene-aryl, SO-aryl, $CONH_2$, CONH—$C_1$-$C_6$ alkyl, $SO_2NH$—$C_1$-$C_6$ alkyl, CON—$(C_1$-$C_6$ alkyl$)_2$, $SO_2N$—$(C_1$-$C_6$ alkyl$)_2$, NH—$SO_2$—$C_1$-$C_6$ alkyl, or NH—CO—$C_1$-$C_6$ alkyl;

and/or optionally, preferably with the condition that when W=W1, $R_w^1$ or B is not an optionally substituted N-pyrrolidinyl radical in the 4-position (para position) with respect to the coupling position with Q;

D: is hydrogen or is defined as for radical A, independent of radical A;

Q: is a radical of general formula Q1

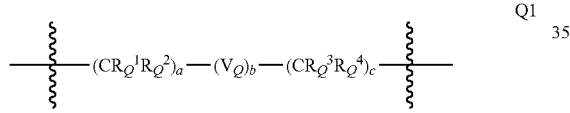

having the indices
a=0-4 (i.e., an integer selected from 0, 1, 2, 3, or 4)
b=0, 1 (i.e., an integer selected from 0 or 1)
c=0-4 (i.e., an integer selected from 0, 1, 2, 3, or 4) wherein the sum of a, b, and c is at least 1 and no greater than 5, and is equal to 0 to 5 for the case: X=N, Y=$CR^4$, Z=$CR^6$;

$R_Q^1$, $R_Q^2$, $R_Q^3$, $R_Q^4$ independently stand for:
hydrogen, halogen, OH, or
in each case optionally substituted $C_1$-$C_6$ alkyl, $C_2$-$C_6$ alkenyl, $C_2$-$C_6$ alkynyl, $C_1$-$C_6$ alkylene-$C_3$-$C_7$ cycloalkyl, $C_3$-$C_7$ cycloalkyl, aryl, $C_1$-$C_4$ alkylene-aryl, hetaryl, or $C_1$-$C_4$ alkylene-hetaryl, or in each case two radicals $R_Q^1$ and $R_Q^2$ or $R_Q^3$ and $R_Q^4$ independently form together with the respective C atom a 3- to 7-membered, in each case optionally substituted, saturated or unsaturated carbocycle or heterocycle, wherein the heterocycle may contain one, two, or three heteroatoms selected from the group comprising O, N, and/or S;

$V_Q$: is in each case optionally substituted —CO—, —CO—$NR_Q^5$—, —$NR_Q^5$—CO—, —O—, —S—, —SO—, —$SO_2$—, —$SO_2$—$NR_Q^5$—, —$NR_Q^5$—$SO_2$—, —CS—, —CS—$NR_Q^5$—, —$NR_Q^5$—CS—, —CS—O—, —O—CS—, —CO—O—, —O—CO—, —O—, ethynylene, —C(=$CR_Q^6R_Q^7$)—, —$CR_Q^6$=$CR_Q^7$—, —$NR_Q^5$—CO—$NR_Q^{5*}$—, —O—CO—$NR_Q^5$—, or —$NR_Q^5$—;

$R_Q^5$, $R_Q^{5*}$ independently stand for:
hydrogen or
in each case optionally substituted $C_1$-$C_6$ alkyl, $C_1$-$C_6$ alkylene-O—$C_1$-$C_6$ alkyl, $C_2$-$C_6$ alkenyl, $C_3$-$C_{12}$ alkynyl, CO—$C_1$-$C_6$ alkyl, CO—O—$C_1$-$C_6$ alkyl, $SO_2$—$C_1$-$C_6$ alkyl, $C_3$-$C_7$ cycloalkyl, aryl, $C_1$-$C_4$ alkylene-aryl, CO—O—$C_1$-$C_4$ alkylene-aryl, CO—$C_1$-$C_4$ alkylene-aryl, CO-aryl, $SO_2$-aryl, hetaryl, CO-hetaryl, or $SO_2$—$C_1$-$C_4$ alkylene-aryl;

$R_Q^6$, $R_Q^7$ independently stand for:
hydrogen, OH, or
in each case optionally substituted $C_1$-$C_6$ alkyl, $C_1$-$C_6$ alkoxy, $C_2$-$C_6$ alkenyl, $C_2$-$C_6$ alkynyl, $C_1$-$C_6$ alkylene-$C_3$-$C_7$ cycloalkyl, $C_3$-$C_7$ cycloalkyl, aryl, $C_1$-$C_4$ alkylene-aryl, hetaryl, or $C_1$-$C_4$ alkylene-hetaryl;

$R^1$, $R^2$ independently stand for:
hydrogen, OH, CN, or
in each case optionally substituted $C_1$-$C_6$ alkyl, O—$C_1$-$C_6$ alkyl, $C_1$-$C_6$-alkylene-O—$C_1$-$C_6$ alkyl, $C_3$-$C_7$ cycloalkyl, O—$C_3$-$C_7$ cycloalkyl, aryl, hetaryl, $C_1$-$C_4$ alkylene-aryl, $C_1$-$C_4$ alkylene-hetaryl, O-aryl, O—$C_1$-$C_4$ alkylene-aryl, O-hetaryl, O—$C_1$-$C_4$ alkylene-hetaryl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O-hetaryl, CO—O—$C_1$-$C_4$ alkylene-aryl, $SO_2$—$C_1$-$C_6$ alkyl, $SO_2$-aryl, $SO_2$-hetaryl, $SO_2$—$C_1$-$C_4$ alkylene-aryl, OCO—$C_1$-$C_6$ alkyl, OCO-aryl, OCO-hetaryl, OCO—$C_1$-$C_4$ alkylene-aryl, OCO—$C_1$-$C_4$ alkylene-hetaryl, $SO_2$—$C_1$-$C_6$ alkyl, $SO_2$-aryl, $SO_2$-hetaryl, or $SO_2$—$C_1$-$C_4$ alkylene-aryl, or $R^1$ and $R^2$ together with the nitrogen form a 5- to 7-membered saturated or unsaturated heterocycle optionally substituted in each case, which may contain one, two, or three further heteroatoms, which may be different or the same, from the group O, N, S, wherein in each case two radicals substituted on this carbocycle or heterocycle together may optionally form a 3- to 7-membered anellated, saturated, unsaturated, or aromatic carbocycle or heterocycle which is optionally substituted in each case, wherein the heterocycle may contain up to three heteroatoms, which may be different or the same, selected from the group comprising O, N, and S, and wherein the cyclic compound that is formed may optionally be substituted;

$R^3$ is a free electron pair or hydrogen;

X, Y, Z X=N, Y=$CR^4$, Z=$CR^6$, or
X=C, Y=$NR^5$, Z=$CR^6$, or
X=C, Y=$CR^4$, Z=$NR^7$, or
X=N, Y=N, Z=$CR^6$, or
X=N, Y=N, Z=$NR^7$
or
X, Y, Z X=N, Y=$CR^4$, Z=$CR^6$, or
X=C, Y=$NR^5$, Z=$CR^6$, or
X=C, Y=$CR^4$, Z=$NR^7$, or
X=N, Y=N, Z=$CR^6$, or
X=N, Y=$CR^4$, Z=N;

$R^4$, $R^6$ in each case independently stand for a radical, selected from the group comprising hydrogen and groups 1.), 3.), 4.), 5.), or 6.), which may be the same or different, and $R^5$, $R^7$ in each case independently stand for a radical selected from groups 2.), 3.), 4.), or 5.), which may be the same or different, wherein groups 1.) through 6.) are defined as follows:
1.) Hydrogen, $NO_2$, $NH_2$, CN, $CF_3$, $CHF_2$, $OCF_3$, $OCHF_2$, COOH, O—$CH_2$—COOH, halogen, or
   in each case optionally substituted $C_1$-$C_{10}$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, $C_1$-$C_6$ alkylene-O—$C_1$-$C_6$ alkyl, $C_1$-$C_6$ alkylene-O-aryl, COO—$C_1$-$C_6$ alkyl, or $C_1$-$C_4$ alkylene-COO—$C_1$-$C_6$ alkyl, or in each case optionally substituted
   O—$R_{Z,Y}^4$, S—$R_{Z,Y}^4$, $NR_{Z,Y}^6 R_{Z,Y}^7$, CO—$OR_{Z,Y}^6$, CO—$R_{Z,Y}^5$, $NR_{Z,Y}^7$—CO—O—$R_{Z,Y}^5$, O—$CH_2$—COO—$R_{Z,Y}^5$, $NR_{Z,Y}^7$—CO—$R_{Z,Y}^5$, $SO_2$—$R_{Z,Y}^5$, SO—$R_{Z,Y}^5$, $NR_{Z,Y}^7$—$SO_2$—$R_{Z,Y}^5$, $SO_2NH_2$, $CONH_2$, $SO_2$—$NR_{Z,Y}^6 R_{Z,Y}^7$, or CO—$R_{Z,Y}^6 R_{Z,Y}^7$;
2.) A free electron pair or hydrogen, $CH_2$—$CF_3$, $CH_2$—$CHF_2$, in each case optionally substituted $C_1$-$C_{10}$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, $C_1$-$C_6$ alkylene-O—$C_1$-$C_6$ alkyl, $C_1$-$C_6$ alkylene-O-aryl, COO—$C_1$-$C_6$ alkyl, or $C_1$-$C_4$ alkylene-COO—$C_1$-$C_6$ alkyl, or in each case optionally substituted
   CO—$OR_{Z,Y}^5$, CO—$R_{Z,Y}^5$, $SO_2$—$R_{Z,Y}^5$, SO—$R_{Z,Y}^5$, $SO_2NH_2$, $CONH_2$, $SO_2$—$NR_{Z,Y}^6 R_{Z,Y}^7$, or CO—$NR_{Z,Y}^6 R_{Z,Y}^7$;
3.) Phenyl, 1-naphthyl, or 2-naphthyl, which in each case are or may be substituted with one, two, or three radicals selected from $R_{Z,Y}^1$, $R_{Z,Y}^2$, and $R_{Z,Y}^3$, wherein
   $R_{Z,Y}^1$, $R_{Z,Y}^2$, and $R_{Z,Y}^3$ in each case independently represent a substituent from the following group:
   Hydrogen, $NO_2$, $NH_2$, OH, CN, $CF_3$, $CHF_2$, $OCF_3$, $OCHF_2$, COOH, O—$CH_2$—COOH, SH, halogen, or
   in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted
   O—$R_{Z,Y}^4$, S—$R_{Z,Y}^4$, $NR_{Z,Y}^6 R_{Z,Y}^7$, CO—$OR_{Z,Y}^5$, $NR_{Z,Y}^7$—CO—O—$R_{Z,Y}^5$, O—$CH_2$—COO—$R_{Z,Y}^5$, $NR_{Z,Y}^7$—CO—$R_{Z,Y}^5$, $NR_{Z,Y}^7$—CO—$NR_{Z,Y}^5$, $SO_2$—$R_{Z,Y}^5$, $NR_{Z,Y}^7$—$SO_2$—$R_{Z,Y}^5$, $NR_{Z,Y}^7$—$SO_2$—$NR_{Z,Y}^5$, $SO_2NH_2$, $CONH_2$, $SO_2$—$NR_{Z,Y}^6 R_{Z,Y}^7$, or CO—$NR_{Z,Y}^6 R_{Z,Y}^7$, or
   in each case two of the radicals selected from the group comprising $R_{Z,Y}^1$, $R_{Z,Y}^2$, or $R_{Z,Y}^3$ form, together with the ring atoms bearing these substituents, a 3- to 7-membered saturated or unsaturated carbocycle which in each case is optionally substituted, or a saturated or unsaturated heterocycle which in each case is optionally substituted and which may contain one, two, or three further heteroatoms, which may be different or the same, selected from the group comprising O, N, and S, wherein optionally in each case two radicals substituted on this carbocycle or heterocycle together may form a 3- to 7-membered, anellated, saturated, unsaturated, or aromatic carbocycle or heterocycle, wherein the heterocycle may contain one, two, or three heteroatoms, which may be different or the same, comprising O, N, and S, and wherein the cyclic compound thus formed may optionally be substituted, and/or a further 3- to 7-membered, optionally substituted cyclic compound may be condensed thereon;
$R_{Z,Y}^4$ is in each case optionally substituted $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, heterocycloalkyl, hetaryl, aryl, $C_1$-$C_4$ alkylene-hetaryl, hetaryl, $C_1$-$C_4$ alkylene-aryl, or $C_1$-$C_6$ alkyl, which in each case is optionally substituted with a substituent selected from the group comprising halogen, $NO_2$, $NH_2$, OH, CN, $CF_3$, $CHF_2$, $OCF_3$, $OCHF_2$, optionally substituted NH—($C_1$-$C_6$ alkyl), or optionally substituted $N(C_1$-$C_6$ alkyl$)_2$;

$R_{Z,Y}^5$ is in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, heterocycloalkyl, or $C_1$-$C_6$ alkylene-O—$C_1$-$C_6$ alkyl, dioxymethylenephenyl, benzofuranyl, dihydrobenzofuranyl, indanyl, or aryl or hetaryl which in each case is optionally singly, doubly, or triply substituted with substituents independently selected from the group comprising halogen, $NO_2$, $NH_2$, OH, CN, $CF_3$, $CHF_2$, $OCF_3$, $OCHF_2$, optionally substituted NH—($C_1$-$C_6$ alkyl) or optionally substituted $N(C_1$-$C_6$ alkyl$)_2$, and COOH, O—$CH_2$—COOH, SH, or
   in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl, or $C_1$-$C_4$ alkylene-aryl, or in each case optionally substituted
   O—$R_A^1$, CO—$R_A^1$, S—$R_A^1$, SO—$R_A^1$, CO—O—$R_A^1$, $NR_A^4$—CO—O—$R_A^1$, O—$CH_2$—COO—$R_A^1$, $NR_A^2 R_A^3$, $CONH_2$, $SO_2NH_2$, $NR_A^4$—CO—$R_A^1$, $SO_2$—$R_A^1$, $NR_A^4$—$SO_2$—$R_A^1$, $SO_2$—$NR_A^2 R_A^3$, or CO—$NR_A^2 R_A^3$;

$R_{Z,Y}^6$ is hydrogen, or
   in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, $C_1$-$C_4$ alkylene-aryl, $C_1$-$C_4$ alkylene-hetaryl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, CO—O—$C_1$-$C_4$ alkylene-aryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$R_{Z,Y}^7$ is hydrogen or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

or the radicals $R_{Z,Y}^6$ and $R_{Z,Y}^7$ together with the nitrogen form a 3- to 7-membered saturated or aromatic heterocycle which is optionally substituted in each case and which may contain one, two, or three further heteroatoms, which may be different or the same, selected from the group comprising O, N, and S; and in each case two radicals substituted on this heterocycle together may optionally form a 3- to 7-membered anellated, saturated, unsaturated, or aromatic carbocycle or heterocycle, wherein the heterocycle may contain one, two, or three heteroatoms, which may be different or the same, selected from the group comprising O, N, and S, and the cyclic compound thus formed may optionally be substituted, or a further 3- to 7-membered, optionally substituted cyclic compound may be condensed thereon;

4.) A 5- or 6-membered, in each case optionally substituted, aromatic heterocycle which may contain one, two, or three heteroatoms which may be different or the same, selected from the group comprising O, N, and S, and which in each case may be substituted with $R_{Z,Y}^1$, $R_{Z,Y}^2$, and $R_{Z,Y}^3$ as defined above;

5.) A $C_5$-$C_{18}$ bi- or tricyclic saturated hydrocarbon radical which in each case is optionally substituted;

6.) $R^4$ and $R^6$ together with X and Y form, optionally substituted in each case, a $C_6$-$C_{10}$-membered saturated, unsaturated or aromatic carbocycle, preferably a benzo radical, which may be substituted in each case with one, two, or three radicals which in each case are independently selected from $R_{Z,Y}^8$.

$R_{Z,Y}^8$: is hydrogen, $NO_2$, $NH_2$, OH, CN, $CF_3$, $CHF_2$, $OCF_3$, $OCHF_2$, COOH, O—$CH_2$—COOH, SH, halogen, or in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted O—$R_{Z,Y}^4$, S—$R_{Z,Y}^4$, $NR_{Z,Y}^6R_{Z,Y}^7$, CO—$OR_{Z,Y}^6$, $NR_{Z,Y}^7$—CO—O—$R_{Z,Y}^5$, O—$CH_2$—COO—$R_{Z,Y}^5$, $NR_{Z,Y}^7$—CO—$R_{Z,Y}^5$, $SO_2$—$R_{Z,Y}^6$, $NR_{Z,Y}^7$—$SO_2$—$R_{Z,Y}^6$, $SO_2NH_2$, $CONH_2$, $SO_2$—$NR_{Z,Y}^6R_{Z,Y}^7$, or CO—$NR_{Z,Y}^6R_{Z,Y}^7$, optionally preferably with one, two, or three of the conditions selected from the group comprising conditions (i), (ii), and (iii) listed below:

(i) with the condition (i) that when $R^4$ and $R^6$ have the meanings given for group 6.), the radicals A, B, Q, $R_Q^1$, and $R_Q^2$ are defined as follows:

A is located in W1 in the 2-position as indicated, and stands for $NH_2$, $OCF_3$, $OCHF_2$, O—$CH_2$—COOH, O—$C_1$-$C_6$ alkyl, S—$C_1$-$C_6$ alkyl, or O—$R_A^1$, CO—$R_A^1$, S—$R_A^1$, SO—$R_A^1$, $SO_2$—$R_A^1$, $SO_2$—$NR_A^2R_A^3$;

B is located in W1 in the 6-position and stands for halogen, CN, $CF_3$, —$CHF_2$, $OCF_3$, $OCHF_2$, or in each case optionally substituted $C_1$-$C_6$ alkyl or $C_2$-$C_6$ alkenyl, —O—$CH_2$—COO—$R_A^1$, —O—$R_A^1$, S—$R_A^1$, $NR_A^2R_A^3$, —$NR_A^4$—CO—$R_A^1$, or —CO—$NR_A^2R_A^3$; $NR_A^4$—$SO_2$—$R_A^1$; or B together with $R_w^1$ forms one of the radicals —$(CH_2)_3$—, —O—$CH_2$—O—, —O—$(CH_2)_2$—O—, —CH=CH—CH=CH—, —O—$(CH_2)_2$—, —$(CH_2)_2$—O—;

Q is —$CR_Q^1R_Q^2$—;

$R_Q^1$, $R_Q^2$ independently stand for:
hydrogen, halogen, optionally substituted $C_1$-$C_6$ alkyl; and/or (ii) with the condition (ii) that when W=W1, $R_w^1$ or B is not an optionally substituted N-pyrrolidinyl radical in the 4-position (para position) with respect to the coupling position with Q; and/or (iii) with the condition (iii) that the sum of a, b, and c is 1, 2, 3, 4, or 5 when X=N, Y=$CR^4$, and Z=$CR^6$.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to Claim 1, and/or corresponding enantiomeric, diastereomeric, and/or tautomeric forms thereof, and/or pharmaceutically acceptable salts thereof, and/or active substance precursors ("prodrugs") thereof, are prepared, wherein the radicals W, A, $R_A^1$, $R_A^2$, $R_A^3$, $R_A^4$, B, $Rw^1$, D, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, X, Y, Z, unless stated otherwise below, have the same meaning as given above or as stated in Claim 1, and the radicals below have the following definitions:

$R^4$, $R^6$ in each case independently stand for a radical selected from the group comprising hydrogen and groups 1.), 3.), 4.), or 5.), which may be the same or different, and $R^5$, $R^7$ in each case independently stand for a radical selected from groups 2.), 3.), 4.), or 5.), which may be the same or different, wherein groups 1.)-5.) in each case have the meanings stated above or in Claim 1.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to Claim 1 or 2, and/or corresponding enantiomeric, diastereomeric, and/or tautomeric forms thereof, and/or pharmaceutically acceptable salts thereof, and/or active substance precursors ("prodrugs") thereof, are prepared, wherein the radicals W, A, $R_A^1$, $R_A^2$, $R_A^3$, $R_A^4$, B, $R_w^1$, D, $R_1$, $R_2$, $R_3$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, $R_{Z,Y}^8$, unless stated otherwise below, have the same meanings as given above or as stated in Claim 1 or 2, and the radicals below have the following definitions:

Q: in formula Q1 is the sum of a, b, and c and is equal to 1, 2, or 3;

$R_Q^1$, $R_Q^2$, $R_Q^3$, $R_Q^4$ independently stand for:
hydrogen, halogen, OH, or optionally substituted $C_1$-$C_6$ alkyl;

$V_Q$: is —CO—, —CO—$NR_Q^5$—, —$NR_Q^5$—CO—, —O—, —S—;

$R_Q^5$: is hydrogen, $CH_3$.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to one of Claims 1 through 3, and/or corresponding enantiomeric, diastereomeric, and/or tautomeric forms thereof, and/or pharmaceutically acceptable salts thereof, and/or active substance precursors ("prodrugs") thereof, are prepared, wherein the radicals W, A, $R_A^1$, $R_A^2$, $R_A^3$, $R_A^4$, B, $R_w^1$, D, $R_1$, $R_2$, $R_3$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, $R_{Z,Y}^8$, unless stated otherwise below, have the same meaning as given above or as stated in one of Claims 1 through 3, and the radicals below have the following definitions:

Q: in formula Q1 is the sum of a=1 and b=c=0;

$R_Q^1$, $R_Q^2$ independently stand for:
  hydrogen, halogen, OH, or optionally substituted $C_1$-$C_6$ alkyl.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to one of Claims 1 through 4, and/or corresponding enantiomeric, diastereomeric, and/or tautomeric forms thereof, and/or pharmaceutically acceptable salts thereof, and/or active substance precursors ("prodrugs") thereof, are prepared, wherein the radicals Q, $R_Q^1$, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, $R_{Z,Y}^8$, unless stated otherwise below, have the same meaning as given above or as stated in one of Claims 1 through 4, and the radicals below have the following definitions:

W: stands for a radical of general formula W1, W21, or W22

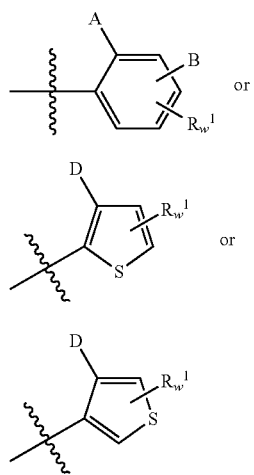

wherein the radicals A, B, D, and $R_w^1$ independently, and in each case independently of their respective occurrence, may have one of the meanings stated below:

A: is halogen, $NH_2$, CN, $CF_3$, $OCF_3$, $OCHF_2$, COOH, O—$CH_2$—COOH, SH, O—$C_1$-$C_6$ alkyl, S—$C_1$-$C_6$ alkyl, $C_1$-$C_6$ alkyl, or in each case optionally substituted O—$R_A^1$, CO—$R_A^1$, S—$R_A^1$, O—$CH_2$—COO—$R_A^1$, $NR_A^2R_A^3$, $CONH_2$, $SO_2NH_2$, $SO_2$—$R_A^1$, $NR_A^4$—$SO_2$—$R_A^1$, $SO_2$—$NR_A^2R_A^3$, or CO—$NR_A^2R_A^3$;

$R_A^1$: is in each case optionally substituted $C_1$-$C_6$ alkyl, $C_3$-$C_7$ cycloalkyl, phenyl, or benzyl;

$R_A^2$; $R_A^3$ independently stand for hydrogen, or
  in each case optionally substituted $C_1$-$C_6$ alkyl, phenyl, benzyl, phenethyl, CO—$C_1$-$C_6$ alkyl, CO-aryl, CO—O—$C_1$-$C_6$ alkyl, $SO_2$—$C_1$-$C_6$ alkyl, $SO_2$-aryl, $SO_2$-hetaryl, or $SO_2$—$C_1$-$C_4$ alkylene-aryl; or both radicals $R_A^2$ and $R_A^3$ together with the nitrogen form a 5- or 6-membered saturated or aromatic ring which is optionally substituted in each case, and which may contain one or two heteroatoms, which may be the same or different, selected from the group comprising O and N;

$R_A^4$: is hydrogen or an optionally substituted $C_1$-$C_6$ alkyl radical;

B: is hydrogen, halogen, CN, $CF_3$, —$CHF_2$, $OCF_3$, $OCHF_2$, or
  in each case optionally substituted $C_1$-$C_6$ alkyl or $C_2$-$C_6$ alkenyl, or in each case optionally substituted —O—$CH_2$—COO—$R_A^1$, —O—$R_A^1$, S—$R_A^1$, $NR_A^2R_A^3$, —$NR_A^4$—CO—$R_A^1$, or CO—$NR_A^2R_A^3$; $NR_A^4$—$SO_2$—$R_A^1$;
  or B together with $R_w^1$ forms one of the radicals —($CH_2$)$_3$—, —O—$CH_2$—O—, —O—($CH_2$)$_2$—O—, —CH=CH—CH=CH—, —O—($CH_2$)$_2$—, or —($CH_2$)$_2$—O—;

$R_w^1$: is hydrogen, F, Cl, CN, $CF_3$, O—$CF_3$, or
  in each case optionally substituted $C_1$-$C_6$ alkyl, aryl, $C_1$-$C_6$ alkylamino, or $C_1$-$C_6$ dialkylamino;

D: is hydrogen or, independently from A, is defined the same way as radical A.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to one of Claims 1 through 5, and/or corresponding enantiomeric, diastereomeric, and/or tautomeric forms thereof, and/or pharmaceutically acceptable salts thereof, and/or active substance precursors ("prodrugs") thereof, are prepared, wherein the radicals W, A, $R_A^1$, $R_A^2$, $R_A^3$, $R_A^4$, B, $R_w^1$, D, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, $R_{Z,Y}^8$, unless stated otherwise below, have the same meaning as given above or as stated in one of Claims 1 through 5, and the radicals below have the following definitions:

$R^1$, $R^2$ independently stand for:
  hydrogen, OH, CN, $C_1$-$C_6$ alkyl, $C_1$-$C_6$ alkylene-O—$C_1$-$C_6$ alkyl, substituted aryl, benzyl, CO—$C_1$-$C_6$ alkyl, CO-aryl, or CO—$C_1$-$C_4$ alkylene-aryl;

$R^3$ is a free electron pair or hydrogen.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to one of Claims 1 through 6, and/or corresponding enantiomeric, diastereomeric, and/or tautomeric forms thereof, and/or pharmaceutically acceptable salts thereof, and/or active substance precursors ("prodrugs") thereof, are prepared, wherein the radicals W, A, $R_A^1$, $R_A^2$, $R_A^3$, $R_A^4$, B, $R_w^1$, D, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, $R_{Z,Y}^8$, unless stated otherwise below, have the same meaning as above or as stated in one of Claims 1 through 6, and the radicals below have the following definitions:

X, Y, Z X=N, Y=$CR^4$, Z=$CR^6$, or
  X=C, Y=$CR^4$, Z=$NR^7$, or
  X=N, Y=$NR^5$, Z=$CR^6$ or

X, Y, Z X=N, Y=CR$^4$, Z=CR$^6$, or
X=C, Y=CR$^4$, Z=NR$^7$, or
X=N, Y=N, Z=CR$^6$.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to one of Claims 1 through 7, and/or corresponding enantiomeric, diastereomeric, and/or tautomeric forms thereof, and/or pharmaceutically acceptable salts thereof, and/or active substance precursors ("prodrugs") thereof, are prepared, wherein the radicals W, A, $R_A^1$, $R_A^2$, $R_A^3$, $R_A^4$, B, $R_W^1$, D, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, $R_{Z,Y}^8$, unless stated otherwise below, have the same meaning as above or as stated in one of Claims 1 through 7, and the radicals below have the following definitions:

X, Y, Z X=N, Y=CR$^4$, Z=CR$^6$, or
X=N, Y=NR$^6$, Z=CR$^6$ or

X, Y, Z X=N, Y=CR$^4$, Z=CR$^6$, or
X=N, Y=N, Z=CR$^6$.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to one of Claims 1 through 8, and/or corresponding enantiomeric, diastereomeric, and/or tautomeric forms thereof, and/or pharmaceutically acceptable salts thereof, and/or active substance precursors ("prodrugs") thereof, are prepared, wherein the radicals W, A, $R_A^1$, $R_A^2$, $R_A^3$, $R_A^4$, B, $R_W^1$, D, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, X, Y, Z, unless stated otherwise below, have the same meaning as above or as stated in one of Claims 1 through 8, and the radicals below have the following definitions:

$R^4$, $R^6$ in each case independently stand for a radical selected from the group comprising hydrogen and groups 1.), 3.), 4.), or 5.), which may be the same or different, and $R^5$, $R^7$ in each case independently stand for a radical selected from groups 2.), 3.), 4.), or 5.), which may be the same or different, wherein groups 1.), 2.), 3.), 4.), and 5.) are defined as follows:

1.) H, CN, CF$_3$, CHF$_2$, O—CH$_2$—COOH, halogen, or
in each case optionally substituted C$_1$-C$_{10}$ alkyl, C$_2$-C$_{10}$ alkenyl, C$_2$-C$_{10}$ alkynyl, C$_3$-C$_7$ cycloalkyl, C$_1$-C$_6$ alkylene-C$_3$-C$_7$ cycloalkyl, C$_1$-C$_4$ alkylene-aryl, C$_1$-C$_4$ alkylene-hetaryl, or in each case optionally substituted O—$R_{Z,Y}^4$, N$R_{Z,Y}^6 R_{Z,Y}^7$, CO—O$R_{Z,Y}^5$, N$R_{Z,Y}^7$—CO—O—$R_{Z,Y}^5$, O—CH$_2$—COO—$R_{Z,Y}^5$, N$R_{Z,Y}^7$—CO—$R_{Z,Y}^5$, SO$_2$—$R_{Z,Y}^5$, N$R_{Z,Y}^7$—SO$_2$—$R_{Z,Y}^5$, SO$_2$NH$_2$, CONH$_2$, SO$_2$—N$R_{Z,Y}^6 R_{Z,Y}^7$, or CO—N$R_{Z,Y}^6 R_{Z,Y}^7$;

2.) A free electron pair or hydrogen,
in each case optionally substituted C$_1$-C$_{10}$ alkyl, C$_3$-C$_7$ cycloalkyl, C$_1$-C$_6$ alkylene-C$_3$-C$_7$ cycloalkyl, C$_1$-C$_4$ alkylene-aryl, C$_1$-C$_4$ alkylene-hetaryl, COO—C$_1$-C$_6$ alkyl, or in each case optionally substituted SO—$R_{Z,Y}^5$, SO$_2$NH$_2$, CONH$_2$, SO$_2$—N$R_{Z,Y}^6 R_{Z,Y}^7$ or CO—N$R_{Z,Y}^6 R_{Z,Y}^7$;

3.) Phenyl, 1-naphthyl, or 2-naphthyl, in each case substituted with $R_{Z,Y}^1$, $R_{Z,Y}^2$, and $R_{Z,Y}^3$, wherein
$R_{Z,Y}^1$, $R_{Z,Y}^2$, and $R_{Z,Y}^3$ in each case independently represent a substituent from the following group:

Hydrogen, NH$_2$, CN, CF$_3$, CHF$_2$, OCF$_3$, OCHF$_2$, O—CH$_2$—COOH, halogen, or in each case optionally substituted aryl, hetaryl, heterocycloalkyl, C$_1$-C$_6$ alkyl, C$_2$-C$_6$ alkenyl, C$_2$-C$_6$ alkynyl, C$_3$-C$_7$ cycloalkyl, C$_1$-C$_4$ alkylene-C$_3$-C$_7$ cycloalkyl, C$_1$-C$_4$ alkylene-heterocycloalkyl, C$_1$-C$_4$ alkylene-aryl, or C$_1$-C$_4$ alkylene-hetaryl, or in each case optionally substituted O—$R_{Z,Y}^4$, S—$R_{Z,Y}^4$, N$R_{Z,Y}^6 R_{Z,Y}^7$, N$R_{Z,Y}^7$—CO—O—$R_{Z,Y}^5$, N$R_{Z,Y}^7$—CO—$R_{Z,Y}^5$, SO$_2$—$R_{Z,Y}^5$, N$R_{Z,Y}^7$—SO$_2$—$R_{Z,Y}^5$, SO$_2$NH$_2$, CONH$_2$, SO$_2$—N$R_{Z,Y}^6 R_{Z,Y}^7$, or CO—N$R_{Z,Y}^6 R_{Z,Y}^7$, or in each case two of the radicals selected from $R_{Z,Y}^1$, $R_{Z,Y}^2$, or $R_{Z,Y}^3$ form, together with the ring atoms bearing these substituents, a 3- to 7-membered saturated or unsaturated carbocycle which in each case is optionally substituted, or a saturated or unsaturated heterocycle which in each case is optionally substituted and which may contain one, two, or three further heteroatoms, which may be the same or different, selected from the group comprising O, N, and S;

$R_{Z,Y}^4$ is in each case optionally substituted C$_1$-C$_4$ alkylene-C$_3$-C$_7$ cycloalkyl, C$_1$-C$_4$ alkylene-heterocycloalkyl, heterocycloalkyl, hetaryl, aryl, C$_1$-C$_4$ alkylene-hetaryl, hetaryl, C$_1$-C$_4$ alkylene-aryl, or C$_1$-C$_6$ alkyl which in each case is optionally substituted with a substituent selected from the group comprising halogen, NO$_2$, NH$_2$, OH, CN, CF$_3$, CHF$_2$, OCF$_3$, OCHF$_2$, NH—(C$_1$-C$_6$ alkyl), and N(C$_1$-C$_6$ alkyl)$_2$;

$R_{Z,Y}^5$ is in each case optionally substituted C$_1$-C$_6$ alkyl, C$_2$-C$_6$ alkenyl, C$_2$-C$_6$ alkynyl, C$_3$-C$_7$ cycloalkyl, C$_1$-C$_4$ alkylene-C$_3$-C$_7$ cycloalkyl, C$_1$-C$_4$ alkylene-heterocycloalkyl, heterocycloalkyl, or C$_1$-C$_6$ alkylene-O—C$_1$-C$_6$ alkyl, dioxymethylenephenyl, or aryl or hetaryl which in each case is optionally singly, doubly, or triply substituted with substituents independently selected from the group comprising halogen, NO$_2$, NH$_2$, OH, CN, CF$_3$, CHF$_2$, OCF$_3$, OCHF$_2$, NH—(C$_1$-C$_6$ alkyl) or N(C$_1$-C$_6$ alkyl)$_2$, COOH, O—CH$_2$—COOH, SH, or in each case optionally substituted C$_1$-C$_6$ alkyl, C$_3$-C$_7$ cycloalkyl, aryl, hetaryl, heterocycloalkyl, or in each case optionally substituted O—$R_A^1$, S—$R_A^1$, N$R_A^4$—CO—O—$R_A^1$, O—CH$_2$—COO—$R_A^1$, N$R_A^2 R_A^3$, CONH$_2$, SO$_2$NH$_2$, SO$_2$—$R_A^1$, N$R_A^4$—SO$_2$—$R_A^1$, or SO$_2$—N$R_A^2 R_A^3$, $R_{Z,Y}^6$ is hydrogen, or
in each case optionally substituted C$_1$-C$_6$ alkyl, C$_3$-C$_7$ cycloalkyl, C$_1$-C$_4$ alkylene-C$_3$-C$_7$ cycloalkyl, C$_1$-C$_4$ alkylene-heterocycloalkyl, aryl, hetaryl, heterocycloalkyl, C$_1$-C$_6$ alkylene-O—C$_1$-C$_6$ alkyl, CO—C$_1$-C$_6$ alkyl, C$_1$-C$_4$ alkylene-aryl, C$_1$-C$_4$ alkylene-hetaryl, CO-aryl, CO-hetaryl, CO—C$_1$-C$_4$ alkylene-aryl, CO—C$_1$-C$_6$ alkylene-hetaryl, CO—O—C$_1$-C$_6$ alkyl, CO—O-aryl, CO—O—C$_1$-C$_4$ alkylene-aryl, CO—O-hetaryl, CO—O—C$_1$-C$_4$ alkylene-hetaryl, CO—O—C$_1$-C$_4$ alkylene-aryl, SO$_2$—C$_1$-C$_6$ alkyl, SO$_2$-aryl, SO$_2$-hetaryl, SO$_2$—C$_1$-C$_4$ alkylene-aryl, or SO$_2$—C$_1$-C$_4$ alkylene-hetaryl;

$R_{Z,Y}^7$ is hydrogen or in each case optionally substituted C$_1$-C$_6$ alkyl;

or the radicals $R_{Z,Y}^6$ and $R_{Z,Y}^7$ together with the nitrogen form a 3- to 7-membered saturated or aromatic heterocycle which is optionally substituted in each case, which may contain one, two, or three further heteroatoms, which may be different or the same, selected from the group comprising O, N, and S;

4.) A 5- or 6-membered aromatic heterocycle which may contain one, two, or three heteroatoms selected from the group comprising O, N, and S, and which in each case may be substituted with $R_{Z,Y}^1$, $R_{Z,Y}^2$, and $R_{Z,Y}^3$, where the radicals $R_{Z,Y}^1$, $R_{Z,Y}^2$, and $R_{Z,Y}^3$ are defined as above;

5.) A C$_5$-C$_{10}$ bi- or tricyclic saturated hydrocarbon radical which is optionally substituted.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to one of Claims 1 through 9, and/or corresponding enantiomeric, diastereomeric, and/or tautomeric forms thereof, and/or pharmaceutically acceptable salts thereof, and/or active substance precursors ("prodrugs") thereof, are prepared, wherein the radicals Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, $R_{Z,Y}^8$, unless stated otherwise below, have the same meaning as above or as stated in one of Claims 1 through 9, and the radicals below have the following definitions:

W: is a radical of the general formula

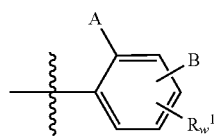

W1

[wherein]

A: is F, Cl, OCF$_3$, OCHF$_2$, in each case optionally substituted C$_1$-C$_6$ alkyl, O—C$_1$-C$_6$ alkyl, S—C$_1$-C$_6$ alkyl, or OR$_A^1$;

B: is hydrogen, F, Cl, CF$_3$, OCF$_3$, OCHF$_2$, in each case optionally substituted C$_1$-C$_6$ alkyl, O—C$_1$-C$_6$ alkyl, or S—C$_1$-C$_6$ alkyl;

$R_w^1$: is hydrogen, F, Cl, CN, CF$_3$, or O—CF$_3$;

$R_A^1$: is C$_1$-C$_6$ alkyl or phenyl optionally substituted in each case.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to one of Claims 1 through 10, and/or corresponding enantiomeric, diastereomeric, and/or tautomeric forms thereof, and/or pharmaceutically acceptable salts thereof, and/or active substance precursors ("prodrugs") thereof, are prepared, wherein the radicals W, A, $R_A^1$, $R_A^2$, $R_A^3$, $R_A^4$, B, $R_w^1$, D, $R_1$, $R_2$, $R_3$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, $R_{Z,Y}^8$, unless stated otherwise below, have the same meaning as given above or as stated in one of Claims 1 through 10, and the radicals below have the following definitions:

Q: is —CR$_Q^1$R$_Q^2$—;

$R_Q^1$, $R_Q^2$ in each case independently stand for hydrogen, F, or CH$_3$.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to one of Claims 1 through 11, and/or corresponding enantiomeric, diastereomeric, and/or tautomeric forms thereof, and/or pharmaceutically acceptable salts thereof, and/or active substance precursors ("prodrugs") thereof, are prepared, wherein the radicals W, A, $R_A^1$, $R_A^2$, $R_A^3$, $R_A^4$, B, $R_w^1$, D, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, X, Y, Z, $R_4$, $R_5$, $R_6$, $R_7$, $R_{Z,Y}^1/R_{Z,Y}^2$, $R_{Z,Y}^3$, $R_{Z,Y}^4$, $R_{Z,Y}^5$, $R_{Z,Y}^6$, $R_{Z,Y}^7$, $R_{Z,Y}^8$, unless stated otherwise below, have the same meaning as given above or as stated in one of Claims 1 through 11, and the radicals below have the following definitions:

$R^1$, $R^2$ independently stand for:
hydrogen, OH, CN, O-methyl, O-phenyl, acetyl, benzoyl, O-acetyl, or O-benzoyl;

$R^3$ is a free electron pair or hydrogen.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to one of Claims 1 through 12, and/or corresponding enantiomeric, diastereomeric, and/or tautomeric forms thereof, and/or pharmaceutically acceptable salts thereof, and/or active substance precursors ("prodrugs") thereof, are prepared, wherein the radicals W, A, $R_A^1$, $R_A^2$, $R_A^3$, $R_A^4$, B, $R_w^1$, D, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, $R_{Z,Y}^8$, unless stated otherwise below, have the same meaning as given above or as stated in one of Claims 1 through 12, and the radicals below have the following definitions:

$R^1$, $R^2$ are hydrogen;

$R^3$ is a free electron pair or hydrogen.

Each of the above-referenced definitions of a variable may be combined with any given number of the above-referenced definitions of the remaining variables. This applies in particular for the combination of preferred definitions of a variable with any given or preferred definitions of the remaining variables According to a further aspect of the present invention, at least one 5-ring heteroaromatic compound of general formula I as given above or according to one of Claims 1 through 13, corresponding enantiomeric, diastereomeric, and/or tautomeric forms thereof, and/or pharmaceutically acceptable salts thereof, and/or active substance precursors ("prodrugs") thereof, are prepared, wherein the radicals W, A, $R_A^1$, $R_A^2$, $R_A^3$, $R_A^4$, B, $R_w^1$, D, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, $R_{Z,Y}^8$, unless stated otherwise below, have the same meaning as given above or as stated in one of Claims 1 through 13, and the radicals below have the following definitions:

X, Y, Z X=N, Y=CR$^4$, Z=CR$^6$.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to one of Claims 1 through 14, and/or corresponding enantiomeric, diastereomeric, and/or tautomeric forms thereof, and/or pharmaceutically acceptable salts thereof, and/or active substance precursors ("prodrugs") thereof, are prepared, wherein the radicals W, A, $R_A^1$, $R_A^2$, $R_A^3$, $R_A^4$, B, $R_w^1$, D, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, X, Y, Z, unless stated otherwise below, have the same meaning as given above or as stated in one of Claims 1 through 14, and the radicals below have the following definitions:

$R^4$, $R^6$ in each case independently stand for a radical, selected from groups 1.), 3.), 4.) or 5.), which may be the same or different, and $R^5$, $R^7$ is a radical selected from groups 2.) or 3.), which may be the same or different, wherein groups 1.), 2.), 3.), 4.), and 5.) are defined as follows:

1.) Hydrogen, CF$_3$, CHF$_2$, or
in each case optionally substituted C$_1$-C$_{10}$ alkyl, C$_3$-C$_7$ cycloalkyl, C$_1$-C$_6$ alkylene-C$_3$-C$_7$ cycloalkyl, C$_1$-C$_4$ alkylene-aryl, C$_1$-C$_4$ alkylene-hetaryl, or in each case optionally substituted
NR$_{Z,Y}^7$—CO—O—R$_{Z,Y}^5$, SO$_2$—R$_{Z,Y}^5$, NR$_{Z,Y}^7$—SO$_2$—R$_{Z,Y}^5$, SO$_2$NH$_2$, CONH$_2$, SO$_2$—NR$_{Z,Y}^6$R$_{Z,Y}^7$ or CO—NR$_{Z,Y}^6$R$_{Z,Y}^7$;

2.) A free electron pair or hydrogen, or
in each case optionally substituted C$_1$-C$_{10}$ alkyl, C$_3$-C$_7$ cycloalkyl;

3.) Phenyl or naphthyl, in each case substituted with $R_{Z,Y}^1$, $R_{Z,Y}^2$, and $R_{Z,Y}^3$, wherein
$R_{Z,Y}^1$, $R_{Z,Y}^2$, and $R_{Z,Y}^3$ in each case independently represent a substituent from the following group:
Hydrogen, CN, NH$_2$, CF$_3$, CHF$_2$, OCF$_3$, OCHF$_2$, O—CH$_2$—COOH, halogen, or in each case optionally substituted aryl, hetaryl, heterocycloalkyl, C$_1$-C$_6$ alkyl, C$_3$-C$_7$ cycloalkyl, or in each case optionally substituted O—R$_{Z,Y}^4$, NR$_{Z,Y}^6$R$_{Z,Y}^7$, SO$_2$—R$_{Z,Y}^6$ R$_{Z,Y}^7$, NR$_{Z,Y}^7$SO$_2$—R$_{Z,Y}^5$, or
in each case two of the radicals from $R_{Z,Y}^1$, $R_{Z,Y}^2$, or $R_{Z,Y}^3$ form, together with the ring atoms bearing these substituents, a 3- to 7-membered saturated or unsaturated carbocycle which in each case is optionally substituted, or a saturated or unsaturated heterocycle which in each case is optionally substituted and which may contain one, two, or three further heteroatoms, which may be the same or different, selected from the group comprising O, N, and S; wherein
$R_{Z,Y}^4$ in each case is an optionally substituted hetaryl, aryl, or C$_1$-C$_6$ alkyl, which in each case is optionally substituted with a substituent selected from the group comprising halogen, CN, CF$_3$, CHF$_2$, OCF$_3$, OCHF$_2$, optionally substituted NH—(C$_1$-C$_6$ alkyl), and optionally substituted N(C$_1$-C$_6$ alkyl)$_2$;

$R_{Z,Y}^5$ in each case is an optionally substituted C$_1$-C$_6$ alkyl, or aryl or hetaryl which in each case is optionally singly, doubly, or triply substituted with substituents independently selected from the group comprising
halogen, NH$_2$, CN, CF$_3$, CHF$_2$, OCF$_3$, OCHF$_2$, NH—(C$_1$-C$_6$ alkyl), or N(C$_1$-C$_6$ alkyl)$_2$, or
optionally substituted C$_1$-C$_6$ alkyl, or in each case optionally substituted
O—R$_A^1$, NR$_A^2$R$_A^3$, SO$_2$NH$_2$, SO$_2$—R$_A^1$, NR$_A^4$—SO$_2$—R$_A^1$, or SO$_2$—NR$_A^2$R$_A^3$;

$R_{Z,Y}^6$ is hydrogen, or
in each case optionally substituted C$_1$-C$_6$ alkyl, aryl, C$_1$-C$_4$ alkylene-aryl, C$_1$-C$_4$ alkylene-hetaryl, SO$_2$—C$_1$-C$_6$ alkyl, SO$_2$-aryl, SO$_2$-hetaryl, or SO$_2$—C$_1$-C$_4$ alkylene-aryl;

$R_{Z,Y}^7$ is hydrogen or in each case optionally substituted C$_1$-C$_6$ alkyl;
or the radicals $R_{Z,Y}^6$ and $R_{Z,Y}^7$ together with the nitrogen form a 3- to 7-membered saturated or aromatic heterocycle which is optionally substituted in each case and which may contain one, two, or three further heteroatoms, which may be different or the same, selected from the group comprising O, N, and S;

4.) A 5- or 6-membered aromatic heterocycle which may contain one, two, or three heteroatoms, which may be different or the same, selected from the group comprising O, N, and S, and which in each case may be substituted with $R_{Z,Y}^1$, $R_{Z,Y}^2$, and $R_{Z,Y}^3$ as defined above;

5.) Optionally substituted adamantyl.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to one of Claims 1 through 15, and/or corresponding enantiomeric, diastereomeric, and/or tautomeric forms thereof, and/or pharmaceutically acceptable salts thereof, and/or active substance precursors ("prodrugs") thereof, are prepared, wherein the radicals $R_Q^1$, $R_Q^2$, $R_Q^3$, $R_Q^4$, $V_Q$, $R_Q^5$, $R_Q^{5*}$, $R_Q^6$, $R_Q^7$, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, $R_{Z,Y}^8$, unless stated otherwise below, have the same meaning as given above or as stated in one of Claims 1 through 15, and the radicals below have the following definitions:

W: is a radical of the general formula

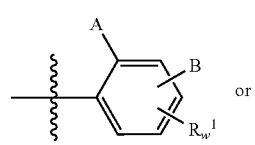

W1

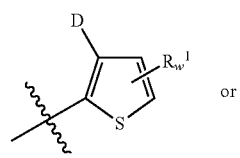

W21

-continued

W22

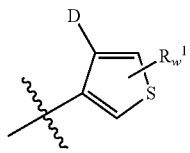

[wherein]
A: is $NH_2$, $OCF_3$, $OCHF_2$, COOH, O—$CH_2$—COOH, SH, or in each case optionally substituted O—$C_1$-$C_6$ alkyl, S—$C_1$-$C_6$ alkyl, $C_1$-$C_6$ alkyl, or in each case optionally substituted
O—$R_A^1$, CO—$R_A^1$, S—$R_A^1$, O—$CH_2$—COO—$R_A^1$, $NR_A^2 R_A^3$, $CONH_2$, $SO_2NH_2$, $SO_2$—$R_A^1$, $NR_A^4$—$SO_2$—$R_A^1$, $SO_2$—$NR_A^2 R_A^3$, or CO—$NR_A^2 R_A^3$;
wherein
$R_A^1$: is in each case optionally substituted $C_1$-$C_6$ alkyl, $C_3$-$C_7$ cycloalkyl, phenyl, or benzyl;
$R_A^2$; $R_A^3$ independently stand for
hydrogen, or
in each case optionally substituted $C_1$-$C_6$ alkyl, phenyl, benzyl, phenethyl, CO—$C_1$-$C_6$ alkyl, CO-aryl, CO—O—$C_1$-$C_6$ alkyl, $SO_2$—$C_1$-$C_4$ alkyl, $SO_2$-aryl, $SO_2$-hetaryl, or $SO_2$—$C_1$-$C_4$ alkylene-aryl;
or both radicals $R_A^2$ and $R_A^3$ together with the nitrogen form a 5- or 6-membered saturated or aromatic ring which is optionally substituted in each case and which may contain one or two heteroatoms, which may be the same or different, selected from the group comprising O and N;
$R_A^4$: is hydrogen or an optionally substituted $C_1$-$C_6$ alkyl radical;
B: is hydrogen, halogen, CN, $CF_3$, —$CHF_2$, $OCF_3$, $OCHF_2$, or in each case optionally substituted $C_1$-$C_6$ alkyl or $C_2$-$C_6$ alkenyl, or in each case optionally substituted —O—$CH_2$—COO—$R_A^1$, —O—$R_A^1$, S—$R_A^1$, $NR_A^2 R_A^3$, —$NR_A^4$—CO—$R_A^1$, or —CO—$NR_A^2 R_A^3$; $NR_A^4$—$SO_2$—$R_A^1$;
or B together with $R_w^1$ forms one of the radicals —$(CH_2)_3$—, —O—$CH_2$—O—, —O—$(CH_2)_2$—O—, —CH=CH—CH=CH—, —O—$(CH_2)_2$—, —$(CH_2)_2$—O—;
$R_w^1$: is hydrogen, F, Cl, CN, $CF_3$, O—$CF_3$, or in each case optionally substituted $C_1$-$C_6$ alkyl, aryl, $C_1$-$C_6$ alkylamino, or $C_1$-$C_6$ dialkylamino;
Q: in formula Q1 is the sum of a, b, and c, which is equal to 1, 2, or 3;
$R_Q^1$, $R_Q^2$, $R_Q^3$, $R_Q^4$ independently stand for:
hydrogen, halogen, OH, optionally substituted $C_1$-$C_6$ alkyl;
$V_Q$: is —CO—, —CO—$NR_Q^5$—, —$NR_Q^5$—CO—, —O—, —S—;
$R_Q^5$: is hydrogen, $CH_3$;
$R^1$, $R^2$ independently stand for:
hydrogen, OH, CN, or in each case optionally substituted $C_1$-$C_6$ alkyl, $C_1$-$C_6$ alkylene-O—$C_1$-$C_6$ alkyl, substituted aryl, benzyl, CO—$C_1$-$C_6$ alkyl, CO-aryl, or CO—$C_1$-$C_4$ alkylene-aryl;
$R^3$ is a free electron pair or hydrogen;
X, Y Z X=N, Y=$CR^4$, Z=$CR^6$, or
X=C, Y=$CR^4$, Z=$NR^7$, or
X=N, Y=N, Z=$CR^6$;
$R^4$, $R^6$ in each case independently stand for a radical, selected from groups 1.), 3.), 4.), or 5.), which may be the same or different, and $R^5$, $R^7$ in each case independently stand for a radical selected from groups 2.), 3.), 4.), or 5.), which may be the same or different, wherein groups 1.) through 5.) have the following meanings:
1.) Hydrogen, CN, $CF_3$, $CHF_2$, O—$CH_2$—COOH, halogen, or in each case optionally substituted $C_1$-$C_{10}$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, or $C_1$-$C_4$ alkylene-hetaryl, or in each case optionally substituted O—$R_{Z,Y}^4$, $NR_{Z,Y}^6 R_{Z,Y}^7$, CO—$OR_{Z,Y}^5$, $NR_{Z,Y}^7$—CO—O—$R_{Z,Y}^5$, O—$CH_2$—COO—$R_{Z,Y}^5$, $NR_{Z,Y}^7$—CO—$R_{Z,Y}^5$, $SO_2$—$R_{Z,Y}^5$, $NR_{Z,Y}^7$—$SO_2$—$R_{Z,Y}^5$, $SO_2NH_2$, $CONH_2$, $SO_2$—$NR_{Z,Y}^6 R_{Z,Y}^7$, or CO—$NR_{Z,Y}^6 R_{Z,Y}^7$;
2.) A free electron pair or hydrogen,
in each case optionally substituted $C_1$-$C_{10}$ alkyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, COO—$C_1$-$C_6$ alkyl, or
SO—$R_{Z,Y}^5$, $SO_2NH_2$, $CONH_2$, or in each case optionally substituted $SO_2$—$NR_{Z,Y}^6 R_{Z,Y}^7$, or CO—$NR_{Z,Y}^6 R_{Z,Y}^7$;
3.) Phenyl, 1-naphthyl, or 2-naphthyl, which in each case are or may be substituted with $R_{Z,Y}^1$, $R_{Z,Y}^2$, and $R_{Z,Y}^3$, wherein
$R_{Z,Y}^1$, $R_{Z,Y}^2$, and $R_{Z,Y}^3$ in each case independently represent a substituent selected from the following group:
Hydrogen, $NH_2$, CN, $CF_3$, $CHF_2$, $OCF_3$, $OCHF_2$, O—$CH_2$—COOH, halogen, or in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted O—$R_{Z,Y}^4$, S—$R_{Z,Y}^4$, $NR_{Z,Y}^6 R_{Z,Y}^7$, $NR_{Z,Y}^7$—CO—O—$R_{Z,Y}^5$, $NR_{Z,Y}^7$—CO—$R_{Z,Y}^5$, $SO_2$—$R_{Z,Y}^5$, $NR_{Z,Y}^7$—$SO_2$—$R_{Z,Y}^5$, $SO_2NH_2$, $SO_2$—$NR_{Z,Y}^6 R_{Z,Y}^7$, $CO_2NH_2$, or CO—$NR_{Z,Y}^6 R_{Z,Y}^7$, or
in each case two of the radicals from $R_{Z,Y}^1$, $R_{Z,Y}^2$, or $R_{Z,Y}^3$ form, together with the ring atoms bearing these substituents, a 3- to 7-membered saturated or unsaturated carbocycle which in each case is optionally substituted, or a saturated or unsaturated heterocycle which in each case is optionally substituted and which may contain one, two, or three further heteroatoms, which may be different or the same, selected from the group comprising O, N, and S;
$R_{Z,Y}^4$ is in each case optionally substituted $C_1$-$C_4$ alkylene-$C_3$-$C_7$ cycloalkyl, $C_1$-$C_4$ alkylene-heterocycloalkyl, heterocycloalkyl, hetaryl, aryl, $C_1$-$C_4$ alkylene-hetaryl, hetaryl, $C_1$-$C_4$ alkylene-aryl, or
$C_1$-$C_6$ alkyl, which in each case is optionally substituted with a substituent selected from the group comprising halogen, $NO_2$, $NH_2$, OH, CN, $CF_3$, $CHF_2$, $OCF_3$, $OCHF_2$, optionally substituted NH—($C_1$-$C_6$ alkyl), and optionally substituted N($C_1$-$C_6$ alkyl)$_2$;
$R_{Z,Y}^5$ is in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, heterocycloalkyl, or $C_1$-$C_6$ alkylene-O—$C_1$-$C_6$ alkyl, dioxymethylenephenyl, or aryl or hetaryl which in each case is optionally singly, doubly, or triply substituted with substituents independently selected from the group comprising halogen, $NO_2$, $NH_2$, OH, CN, $CF_3$, $CHF_2$, $OCF_3$, $OCHF_2$, optionally substituted NH—($C_1$-$C_6$ alkyl) or optionally substituted N($C_1$-$C_6$ alkyl)$_2$, COOH, O—$CH_2$—COOH, SH, or optionally substituted $C_1$-$C_6$ alkyl, $C_3$-$C_7$ cycloalkyl, aryl, hetaryl, heterocycloalkyl, or O—$R_A^1$, S—$R_A^1$, $NR_A^4$—CO—O—$R_A^1$, O—$CH_2$—COO—$R_A^1$, $NR_A^2R_A^3$, $CONH_2$, $SO_2NH_2$, $SO_2$—$R_A^1$, $NR_A^4$—$SO_2$—$R_A^1$, or $SO_2$—$NR_A^2R_A^3$;

$R_{Z,Y}^6$ is hydrogen, or in each case optionally substituted $C_1$-$C_6$ alkyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, $C_1$-$C_4$ alkylene-aryl, $C_1$-$C_4$ alkylene-hetaryl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, CO—O—$C_1$-$C_4$ alkylene-aryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$R_{Z,Y}^7$ is hydrogen or in each case optionally substituted $C_1$-$C_6$ alkyl;

or the radicals $R_{Z,Y}^6$ and $R_{Z,Y}^7$ together with the nitrogen form a 3- to 7-membered saturated or aromatic heterocycle which is optionally substituted in each case and which may contain one, two, or three further heteroatoms, which may be different or the same, selected from the group comprising O, N, and S;

4.) A 5- or 6-membered aromatic heterocycle which may contain one, two, or three heteroatoms, which may be different or the same, selected from the group comprising O, N, and S, and which in each case may be substituted with $R_{Z,Y}^1$, $R_{Z,Y}^2$, and $R_{Z,Y}^3$ as defined above;

5.) A $C_5$-$C_{10}$ bi- or tricyclic saturated hydrocarbon radical which is optionally substituted in each case.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to one of Claims 1 through 16, and/or corresponding enantiomeric, diastereomeric, and/or tautomeric forms thereof, and/or pharmaceutically acceptable salts thereof, and/or active substance precursors ("prodrugs") thereof, are prepared, wherein the radicals W, A, $R_A^1$, $R_A^2$, $R_A^3$, $R_A^4$, B, $R_w^1$, D, Q, a, b, c, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, X, Y, Z, unless stated otherwise below, have the same meaning as given above or as stated in one of Claims 1 through 16, and the radicals below have the following definitions:

W: is a radical of the general formula

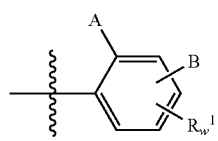

W1

[wherein]

A: is F, Cl, $OCF_3$, $OCHF_2$, in each case optionally substituted $C_1$-$C_6$ alkyl, O—$C_1$-$C_6$ alkyl or S—$C_1$-$C_6$ alkyl or optionally substituted $OR_A^1$;

$R_A^1$: is in each case optionally substituted $C_1$-$C_6$ alkyl or phenyl;

B: is hydrogen, F, Cl, $CF_3$, $OCF_3$, $OCHF_2$, or in each case optionally substituted $C_1$-$C_6$ alkyl, O—$C_1$-$C_6$ alkyl, or S—$C_1$-$C_6$ alkyl;

$R_w^1$: is hydrogen, F, Cl, CN, $CF_3$, or O—$CF_3$;

Q: is —$CR_Q^1R_Q^2$—;

$R_Q^1$, $R_Q^2$ in each case independently stand for hydrogen, F, $CH_3$;

$R^1$, $R^2$ independently stand for:
hydrogen, OH, CN, O-methyl, O-phenyl, acetyl, benzoyl, O-acetyl, O-benzoyl;

$R^3$ is a free electron pair or hydrogen;

X, Y, Z X=N, Y=$CR^4$, Z=$CR^6$, or
X=N, Y=N, Z=$CR^6$;

$R^4$, $R^6$ in each case independently stand for a radical, selected from groups 1.), 3.), 4.), or 5.), which may be the same or different, and $R^5$ is a radical selected from groups 2.) or 3.), which may be the same or different, wherein groups 1.) through 5.) have the following meanings:

1.) Hydrogen, CN, $CF_3$, $CHF_2$, O—$CH_2$—COOH, halogen, or in each case optionally substituted $C_1$-$C_{10}$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, or in each case optionally substituted O—$R_{Z,Y}^4$, $NR_{Z,Y}^6R_{Z,Y}^7$, CO—$OR_{Z,Y}^6$, $NR_{Z,Y}^7$—CO—O—$R_{Z,Y}^6$, O—$CH_2$—COO—$R_{Z,Y}^5$, $NR_{Z,Y}^7$—CO—$R_{Z,Y}^5$, $SO_2$—$R_{Z,Y}^5$, $NR_{Z,Y}^7$—$SO_2$—$R_{Z,Y}^5$, $SO_2NH_2$, $CONH_2$, $SO_2$—$NR_{Z,Y}^6R_{Z,Y}^7$, or CO—$NR_{Z,Y}^6R_{Z,Y}^7$;

2.) A free electron pair or hydrogen,
in each case optionally substituted $C_1$-$C_{10}$ alkyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, COO—$C_1$-$C_4$ alkyl, or SO—$R_{Z,Y}^5$, $SO_2NH_2$, $CONH_2$, optionally substituted $SO_2$—$NR_{Z,Y}^6R_{Z,Y}^7$, or optionally substituted CO—$NR_{Z,Y}^6R_{Z,Y}^7$;

3.) Phenyl, 1-naphthyl, or 2-naphthyl, which in each case may be substituted with $R_{Z,Y}^1$, $R_{Z,Y}^2$, and $R_{Z,Y}^3$, wherein $R_{Z,Y}^1$, $R_{Z,Y}^2$, and $R_{Z,Y}^3$ in each case independently represent a substituent from the following group:

Hydrogen, $NH_2$, CN, $CF_3$, $CHF_2$, $OCF_3$, $OCHF_2$, O—$CH_2$—COOH, halogen, or in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$-alkylene-aryl, or $C_1$-$C_4$ alkylene-hetaryl, or in each case optionally substituted O—$R_{Z,Y}^4$, S—$R_{Z,Y}^4$, $NR_{Z,Y}^6R_{Z,Y}^7$, $NR_{Z,Y}^7$—CO—O—$R_{Z,Y}^5$, $NR_{Z,Y}^7$—CO—$R_{Z,Y}^5$, $SO_2$—$R_{Z,Y}^5$, $NR_{Z,Y}^7$—$SO_2$—$R_{Z,Y}^5$, $SO_2NH_2$, $SO_2$—$NR_{Z,Y}^6R_{Z,Y}^7$, or CO—$NR_{Z,Y}^6R_{Z,Y}^7$, or in each case two of the radicals from $R_{Z,Y}^1$, $R_{Z,Y}^2$, or $R_{Z,Y}^3$ form, together with the ring atoms bearing these substituents, a 3- to 7-membered saturated or unsaturated carbocycle which in each case is optionally substituted, or a saturated or unsaturated heterocycle which in each case is optionally substituted and which may contain one, two, or three further heteroatoms, which may be different of the same, selected from the group comprising O, N, and S;

$R_{Z,Y}^4$ in each case is an optionally substituted $C_1$-$C_4$ alkylene-$C_3$-$C_7$ cycloalkyl, $C_1$-$C_4$ alkylene-heterocycloalkyl, heterocycloalkyl, hetaryl, aryl, $C_1$-$C_4$ alkylene-hetaryl, hetaryl, $C_1$-$C_4$ alkylene-aryl, or $C_1$-$C_6$ alkyl which in each case is optionally substituted with a substituent selected from the group comprising halogen, $NO_2$, $NH_2$, OH, CN, $CF_3$, $CHF_2$, $OCF_3$, $OCHF_2$, optionally substituted NH—($C_1$-$C_6$ alkyl), and optionally substituted $N(C_1$-$C_6$ alkyl$)_2$;

$R_{Z,Y}^5$ is in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, heterocycloalkyl, or $C_1$-$C_6$ alkylene-O—$C_1$-$C_6$ alkyl, dioxymethylenephenyl, or aryl or hetaryl which in each case is optionally singly, doubly, or triply substituted with substituents independently selected from the group comprising halogen, $NO_2$, $NH_2$, OH, CN, $CF_3$, $CHF_2$, $OCF_3$, $OCHF_2$, optionally substituted NH—($C_1$-$C_6$ alkyl) or optionally substituted $N(C_1$-$C_6$ alkyl$)_2$, COOH, O—$CH_2$—COOH, SH, or in each case optionally substituted $C_1$-$C_6$ alkyl, $C_3$-$C_7$ cycloalkyl, aryl, hetaryl, heterocycloalkyl, or in each case optionally substituted O—$R_A^1$, S—$R_A^1$, $NR_A^4$—CO—O—$R_A^1$, O—$CH_2$—COO—$R_A^1$, $NR_A^2R_A^3$, $CONH_2$, $SO_2NH_2$, $SO_2$—$R_A^1$, $NR_A^4$—$SO_2$—$R_A^1$, or $SO_2$—$NR_A^2R_A^3$;

$R_{Z,Y}^6$ is hydrogen, or
in each case optionally substituted $C_1$-$C_6$ alkyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, $C_1$-$C_4$ alkylene-aryl, $C_1$-$C_4$ alkylene-hetaryl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, CO—O—$C_1$-$C_4$ alkylene-aryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$R_{Z,Y}^7$ is hydrogen or optionally substituted $C_1$-$C_6$ alkyl; or the radicals $R_{Z,Y}^6$ and $R_{Z,Y}^7$ together with the nitrogen form a 3- to 7-membered saturated or aromatic heterocycle which is optionally substituted in each case and which may contain one, two, or three further heteroatoms, which may be different or the same, selected from the group comprising O, N, and S;

4.) A 5- or 6-membered aromatic heterocycle which may contain one, two, or three heteroatoms, which may be different or the same, selected from the group comprising O, N, and S,
and which in each case may be substituted with $R_{Z,X}^1$, $R_{Z,X}^2$, and $R_{Z,X}^3$ as defined above;

5.) Optionally substituted adamantyl.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as given above or according to one of Claims 1 through 17, and/or corresponding enantiomeric, diastereomeric, and/or tautomeric forms thereof, and/or pharmaceutically acceptable salts thereof, and/or active substance precursors ("prodrugs") thereof, are prepared, wherein the radicals W, A, $R_A^1$, $R_A^2$, $R_A^3$, $R_A^4$, B, $R_w^1$, D, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, X, Y, Z, unless stated otherwise below, have the same meanings as given above or as stated in one of Claims 1 through 17, and the radicals below have the following definitions:

W: is a radical of the general formula

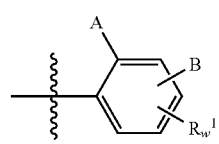

W1

[wherein]
A: is $OCF_3$, $OCHF_2$, $OCH_3$, methyl, O-ethyl, O-propyl, or O-isopropyl;
B: is hydrogen, F, Cl, $CF_3$, $OCF_3$, $OCHF_2$, optionally substituted $C_1$-$C_6$ alkyl, or optionally substituted O—$C_1$-$C_6$ alkyl;
$R_w^1$: is hydrogen, F, Cl;
Q: is —$CH_2$—;
$R^1$, $R^2$ are hydrogen;
$R^3$ is a free electron pair or hydrogen;
X is N
Y is $CR^4$
Z is $CR^6$;
$R^4$, $R^6$ in each case independently stand for a radical, selected from groups 1.), 2.), or 3.), which may be the same or different, wherein groups 1.) through 3.) mean the following:

1.) Hydrogen, $CF_3$, $CHF_2$, or in each case optionally substituted $C_1$-$C_{10}$ alkyl; or
2.) Phenyl, 1-naphthyl, or 2-naphthyl, which in each case are substituted with $R_{Z,Y}^1$, $R_{Z,Y}^2$, and $R_{Z,Y}^3$, wherein $R_{Z,Y}^1$, $R_{Z,Y}^2$, and $R_{Z,Y}^3$ in each case independently represent a substituent from the following group:
Hydrogen, CN, $CF_3$, $CHF_2$, $OCF_3$, $OCHF_2$, O—$CH_2$—COOH, halogen, or
in each case optionally substituted $C_1$-$C_6$ alkyl, aryl, or in each case optionally substituted O—$R_{Z,Y}^4$, $NR_{Z,Y}^6R_{Z,Y}^7$, $NR_{Z,Y}^7$—$SO_2$—$R_{Z,Y}^5$, or
in each case two of the radicals selected from the group comprising $R_{Z,Y}^1$, $R_{Z,Y}^2$, or $R_{Z,Y}^3$ together form one of the radicals —O—$CH_2$—O—, —O—$CH_2$—$CH_2$—O—, —O—$CH_2$—$CH_2$—, or —$CH_2$—$CH_2$—$CH_2$—;

$R_{Z,Y}^4$ is in each case optionally substituted hetaryl, aryl, or $C_1$-$C_6$ alkyl;
$R_{Z,Y}^5$ is in each case optionally substituted $C_1$-$C_6$ alkyl, or aryl or hetaryl, which in each case is optionally singly, doubly, or triply substituted with substituents independently selected from the group comprising halogen, $NH_2$, CN, $CF_3$, $CHF_2$, $OCF_3$, $OCHF_2$, optionally substituted NH—($C_1$-$C_6$ alkyl) or in each case optionally substituted $N(C_1$-$C_6$ alkyl$)_2$, or optionally substituted $C_1$-$C_6$ alkyl, or optionally substituted O—$R_A^1$, $NR_A^2R_A^3$, $SO_2NH_2$, $SO_2$—$R_A^1$, $NR_A^4$—$SO_2$—$R_A^1$, or $SO_2$—$NR_A^2R_A^3$;

$R_{Z,Y}^6$ is hydrogen, or
in each case optionally substituted $C_1$-$C_6$ alkyl, aryl, $SO_2$—$C_1$-$C_6$ alkyl, $SO_2$-aryl;
$R_{Z,Y}^7$ is hydrogen or optionally substituted $C_1$-$C_6$ alkyl;

3.) Benzothiophenyl, benzofuranyl, quinolinyl, isoquinolinyl, thienyl, furanyl, pyridinyl, pyrimidinyl, or thiazolyl, which in each case may be substituted with $R_{Z,Y}^1$, $R_{Z,Y}^2$, and $R_{Z,Y}^3$.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, at least one 5-ring heteroaromatic compound of general formula I as described above, and/or corresponding enantiomeric, diastereomeric, and/or tautomeric forms thereof, and/or pharmaceutically acceptable salts thereof, and/or active substance precursors ("prodrugs") thereof, wherein the radicals $R^1$, $R^2$, $R^3$, Q, W, X, Y, and Z have the meanings stated above, are prepared for use as medicaments.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, a pharmaceutical composition containing at least one 5-ring heteroaromatic compound of general formula I as described above, and/or corresponding enantiomeric, diastereomeric, and/or tautomeric forms thereof, and/or pharmaceutically acceptable salts thereof, and/or active substance precursors ("prodrugs") thereof, and optionally at least one pharmaceutically acceptable carrier and/or diluent, is prepared, wherein the radicals $R^1$, $R^2$, $R^3$, Q, W, X, Y, and Z have the meanings stated above.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, the use of at least one 5-ring heteroaromatic compound of general formula I

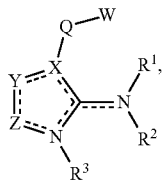

I and/or corresponding enantiomeric, diastereomeric, and/or tautomeric forms thereof, and/or pharmaceutically acceptable salts thereof, and/or active substance precursors ("prodrugs") thereof, wherein the radicals $R^1$, $R^2$, $R^3$, Q, W, X, Y, and Z are defined as follows:

W: is a radical of general formula W11 or W2

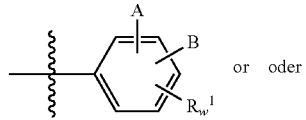 or oder W11

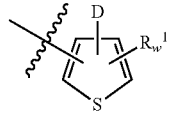 W2 wherein
A: is $NO_2$, $NH_2$, CN, $CF_3$, $OCF_3$, $CHF_2$, $OCHF_2$, COOH, O—$CH_2$—COOH, halogen, SH, or in each case optionally substituted O—$C_1$-$C_6$ alkyl, S—$C_1$-$C_6$ alkyl, —O—CO—$C_1$-$C_6$ alkyl, —O—CO aryl, —O—CO hetaryl, —O—COO—$C_1$-$C_6$ alkyl, or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl, or $C_1$-$C_4$ alkylene-aryl, or in each case optionally substituted
O—$R_A^1$, CO—$R_A^1$, S—$R_A^1$, SO—$R_A^1$, CO—O—$R_A^1$, $NR_A^4$—CO—O—$R_A^1$, O—$CH_2$—COO—$R_A^1$, $NR_A^2R_A^3$, $CONH_2$, $SO_2NH_2$, $NR_A^4$—CO—$R_A^1$, $SO_2$—$R_A^1$, $NR_A^4$—$SO_2$—$R_A^1$, $SO_2$—$NR_A^2R_A^3$, or CO—$NR_A^2R_A^3$;

$R_A^1$: is in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_2$-$C_6$ alkenylene-aryl, or $C_1$-$C_6$ alkylene-hetaryl;

$R_A^2$: is hydrogen, or
in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$R_A^3$: is in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$ alkyl, CO—$C_1$-$C_6$ alkyl, CO-aryl, CO hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;
or the radicals $R_A^2$ and $R_A^3$ together with the nitrogen form a 3- to 7-membered saturated or aromatic heterocycle which is optionally substituted in each case and which may contain one, two, or three further heteroatoms, which may be different or the same, selected from the group comprising O, N, and S;

wherein two radicals substituted on this heterocycle together may optionally form a 3- to 7-membered anellated, saturated, unsaturated, or aromatic carbocycle or heterocycle which is optionally substituted in each case, wherein the heterocycle may contain up to three heteroatoms, which may be different or the same, selected from the group comprising O, N, and S, and wherein the cyclic compound thus formed may optionally be substituted, or a further, optionally 3- to 7-membered, in each case optionally substituted cyclic compound may be condensed thereon;

$R_A^4$: is hydrogen, or
  in each case optionally substituted $C_1$-$C_6$ alkyl, $C_2$-$C_6$ alkenyl, $C_2$-$C_{12}$ alkynyl, $C_3$-$C_7$ cycloalkyl, aryl, $C_1$-$C_4$ alkylene-aryl, $C_1$-$C_6$ alkylene-O—$C_1$-$C_6$ alkyl, or hetaryl;

B: is hydrogen, OH, or is defined as for radical A, independently of A, or two of the radicals A, B, or $R_w^1$ in each case independently form, together with the attached C atoms, a 3- to 7-membered, saturated, unsaturated, or aromatic carbocycle which in each case is optionally substituted, or a 3- to 7-membered saturated, unsaturated or aromatic heterocycle which in each case is optionally substituted and which may contain one, two, or three further heteroatoms, which may be different or the same, selected from the group comprising O, N, and S, wherein in each case two radicals substituted on this carbocycle or heterocycle together may optionally form a 3- to 7-membered anellated, saturated, unsaturated, or aromatic carbocycle or heterocycle which is optionally substituted in each case, wherein the heterocycle may contain up to three heteroatoms, which may be different or the same, selected from the group comprising O, N, and S, and wherein the cyclic compound that is formed may optionally be substituted;

$R_w^1$: is hydrogen, OH, halogen, $NO_2$, $NH_2$, CN, $CF_3$, $CHF_2$, $CH_2F$, $OCF_3$, $OCHF_2$, $OCH_2F$, or
  in each case is optionally substituted $C_1$-$C_6$ alkyl, $C_3$-$C_7$ cycloalkyl, $C_1$-$C_6$ alkylene-O—$C_1$-$C_6$ alkyl, $C_1$-$C_6$ thioalkyl, aryl, hetaryl, O—$C_1$-$C_6$ alkyl, O-benzyl, $C_1$-$C_6$ alkylamino, $C_1$-$C_6$ dialkylamino, pyrrolidinyl, piperidinyl, morpholinyl, CO—$C_1$-$C_6$ alkyl, $SO_2$—$C_1$-$C_6$ alkyl, CO-aryl, $SO_2$-aryl, CO—$C_1$-$C_4$ alkylene-aryl, $SO_2$—$C_1$-$C_4$ alkylene-aryl, SO-aryl, $CONH_2$, CONH—$C_1$-$C_6$ alkyl, $SO_2NH$—$C_1$-$C_6$ alkyl, CON—$(C_1$-$C_6$ alkyl$)_2$, $SO_2N$—$(C_1$-$C_6$ alkyl$)_2$, NH—$SO_2$—$C_1$-$C_6$ alkyl, or NH—CO—$C_1$-$C_6$ alkyl;

D: is defined as for radical A, independently of A;

Q: is a radical of general formula Q1

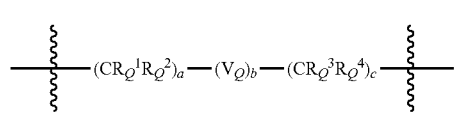

having the indices
a=0, 1, 3, or 4
b=0 or 1
c=0, 1, 2, 3, or 4
wherein the sum of a, b, and c is equal to 1, 2, 3, 4, or 5, preferably optionally with the condition that the sum of a, b, and c is equal to 0, 1, 2, 3, 4, or 5 when X=N, Y=$CR^4$, and Z=$CR^6$;

$R_Q^1$, $R_Q^2$, $R_Q^3$, $R_Q^4$ independently stand for:
  hydrogen, halogen, OH, or
  in each case optionally substituted $C_1$-$C_6$ alkyl, $C_2$-$C_6$ alkenyl, $C_2$-$C_6$ alkynyl, $C_1$-$C_6$ alkylene-$C_3$-$C_7$ cycloalkyl, $C_3$-$C_7$ cycloalkyl, aryl, $C_1$-$C_4$ alkylene-aryl, hetaryl, or $C_1$-$C_4$ alkylene-hetaryl, or
  in each case two radicals $R_Q^1$ and $R_Q^2$ or $R_Q^3$ and $R_Q^4$ independently form together with the respective C atom a 3- to 7-membered, in each case optionally substituted, saturated or
  unsaturated carbocycle or heterocycle, wherein the heterocycle may contain up to three heteroatoms selected from the group comprising O, N, and/or S;

$V_Q$: is in each case optionally substituted —CO—, —$NR_Q^5$—CO—, —O—, —S—, —SO—, —$SO_2$—, —$SO_2$—$NR_Q^5$—, —$NR_Q^5$—$SO_2$—, —CS—, —CS—$NR_Q^5$—, —$NR_Q^5$—CS—, —CS—O—, —O—CS—, —CO—O—, —O—CO—, —O—, ethynylene, —C(=$CR_Q^5R_Q^7$)—, —$CR_Q^6$=$CR_Q^7$—, —$NR_Q^5$—CO—$NR_Q^{5*}$—, —O—CO—$NR_Q^5$—, or —$NR_Q^5$—;

$R_Q^5$, $R_Q^{5*}$ independently stand for:
  hydrogen or
  in each case optionally substituted $C_1$-$C_6$ alkyl, $C_1$-$C_6$ alkylene-O—$C_1$-$C_6$ alkyl, $C_2$-$C_6$ alkenyl, $C_3$-$C_{12}$ alkynyl, CO—$C_1$-$C_6$ alkyl, CO—O—$C_1$-$C_6$ alkyl, $SO_2$—$C_1$-$C_6$ alkyl, $C_3$-$C_7$ cycloalkyl, aryl, $C_1$-$C_4$ alkylene-aryl, CO—O—$C_1$-$C_4$ alkylene-aryl, CO—$C_1$-$C_4$ alkylene-aryl, CO-aryl, $SO_2$-aryl, hetaryl, CO-hetaryl, or $SO_2$—$C_1$-$C_4$ alkylene-aryl;

$R_Q^6$, $R_Q^7$ independently stand for:
  hydrogen, OH, or
  in each case optionally substituted $C_1$-$C_6$ alkyl, $C_1$-$C_6$ alkoxy, $C_2$-$C_6$ alkenyl, $C_2$-$C_6$ alkynyl, $C_1$-$C_6$ alkylene-$C_3$-$C_7$ cycloalkyl, $C_3$-$C_7$ cycloalkyl, aryl, $C_1$-$C_4$ alkylene-aryl, hetaryl, or $C_1$-$C_4$ alkylene-hetaryl;

$R^1$, $R^2$ independently stand for:
  hydrogen, OH, CN, or
  in each case optionally substituted $C_1$-$C_6$ alkyl, O—$C_1$-$C_6$ alkyl, $C_1$-$C_6$ alkylene-O—$C_1$-$C_6$ alkyl, $C_3$-$C_7$ cycloalkyl, O—$C_3$-$C_7$ cycloalkyl, aryl, hetaryl, $C_1$-$C_4$ alkylene-aryl, $C_1$-$C_4$ alkylene-hetaryl, O-aryl, O—$C_1$-$C_4$ alkylene-aryl, O-hetaryl, O—$C_1$-$C_4$ alkylene-hetaryl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O-hetaryl, CO—O—$C_1$-$C_4$ alkylene-aryl, $SO_2$—$C_1$-$C_6$ alkyl, $SO_2$-aryl, $SO_2$-hetaryl, $SO_2$—$C_1$-$C_4$ alkylene-aryl, OCO—$C_1$-$C_6$ alkyl, OCO-aryl, OCO-hetaryl, OCO—$C_1$-$C_4$ alkylene-aryl, OCO—$C_1$-$C_4$ alkylene-hetaryl, $SO_2$—$C_1$-$C_6$ alkyl, $SO_2$-aryl, $SO_2$-hetaryl, or $SO_2$—$C_1$-$C_4$ alkylene-aryl, or
  $R^1$ and $R^2$ together with the nitrogen form a 5- to 7-membered saturated or unsaturated heterocycle which is optionally substituted in each case and which may contain one, two, or three further heteroatoms, which may be different or the same, selected from the group comprising O, N, and S, wherein in each case two radicals substituted on this carbocycle or heterocycle together may optionally form a 3- to 7-membered anellated, saturated, unsaturated, or aromatic carbocycle or heterocycle which is optionally substituted in each case, wherein the heterocycle may contain one, two, or three heteroatoms, which may be different or the same, selected from the group comprising O, N, and S, and wherein the cyclic compound thus formed may optionally be substituted;

$R^3$ is a free electron pair or hydrogen;
X, Y, Z X=N, Y=$CR^4$, Z=$CR^6$, or
  X=C, Y=$NR^6$, Z=$CR^6$, or X=C, Y=CR$^4$, Z=NR$^7$, or
X=N, Y=N, Z=CR$^6$, or
X=N, Y=CR$^4$, Z=N;

R$^4$, R$^6$ in each case independently stand for a radical, selected from groups 1.), 3.), 4.), 5.), or 6.), which may be the same or different, and R$^5$, R$^7$ in each case independently stand for a radical selected from groups 2.), 3.), 4.), or 5.), which may be the same or different, wherein groups 1.) through 6.) are defined as follows:

1.) H, NO$_2$, NH$_2$, CN, CF$_3$, CHF$_2$, OCF$_3$, OCHF$_2$, COOH, O—CH$_2$—COOH, halogen, or
  in each case optionally substituted C$_1$-C$_{10}$ alkyl, C$_2$-C$_{10}$ alkenyl, C$_2$-C$_{10}$ alkynyl, C$_3$-C$_7$ cycloalkyl, C$_1$-C$_6$ alkylene-C$_3$-C$_7$ cycloalkyl, C$_1$-C$_4$ alkylene-aryl, C$_1$-C$_4$ alkylene-hetaryl, C$_1$-C$_6$ alkylene-O—C$_1$-C$_6$ alkyl, C$_1$-C$_6$ alkylene-O-aryl, COO—C$_1$-C$_6$ alkyl, or C$_1$-C$_4$ alkylene-COO—C$_1$-C$_6$ alkyl, or in each case optionally substituted
    O—R$_{Z,Y}^4$, S—R$_{Z,Y}^4$, NR$_{Z,Y}^6$R$_{Z,Y}^7$, CO—OR$_{Z,Y}^5$, CO—R$_{Z,Y}^5$, NR$_{Z,Y}^7$—CO—O—R$_{Z,Y}^5$, O—CH$_2$—COO—R$_{Z,Y}^5$, NR$_{Z,Y}^7$—CO—R$_{Z,Y}^5$, SO$_2$—R$_{Z,Y}^5$, SO—R$_{Z,Y}^5$, NR$_{Z,Y}^7$—SO$_2$—R$_{Z,Y}^5$, SO$_2$NH$_2$, CONH$_2$, SO$_2$—NR$_{Z,Y}^6$R$_{Z,Y}^7$, or CO—NR$_{Z,Y}^6$R$_{Z,Y}^7$;

2.) A free electron pair or hydrogen, CH$_2$—CF$_3$, CH$_2$—CHF$_2$, in each case optionally substituted C$_1$-C$_{10}$ alkyl, C$_2$-C$_{10}$ alkenyl, C$_2$-C$_{10}$ alkynyl, C$_3$-C$_7$ cycloalkyl, C$_1$-C$_6$ alkylene-C$_3$-C$_7$ cycloalkyl, C$_1$-C$_4$ alkylene-aryl, C$_1$-C$_4$ alkylene-hetaryl, C$_1$-C$_6$ alkylene-O—C$_1$-C$_6$ alkyl, C$_1$-C$_6$ alkylene-O-aryl, COO—C$_1$-C$_6$ alkyl, or C$_1$-C$_4$ alkylene-COO—C$_1$-C$_6$ alkyl, or in each case optionally substituted
    CO—OR$_{Z,Y}^5$, CO—R$_{Z,Y}^5$, SO$_2$—R$_{Z,Y}^5$, SO—R$_{Z,Y}^5$, SO$_2$NH$_2$, CONH$_2$, SO$_2$—NR$_{Z,Y}^6$R$_{Z,Y}^7$, or CO—NR$_{Z,Y}^6$R$_{Z,Y}^7$;

3.) Phenyl, 1-naphthyl, or 2-naphthyl, which in each case may be substituted with R$_{Z,Y}^1$, R$_{Z,Y}^2$, and R$_{Z,Y}^3$, wherein R$_{Z,Y}^1$, R$_{Z,Y}^2$, and R$_{Z,Y}^3$ in each case independently represent a substituent from the following group:
  Hydrogen, NO$_2$, NH$_2$, OH, CN, CF$_3$, CHF$_2$, OCF$_3$, OCHF$_2$, COOH, O—CH$_2$—COOH, SH, halogen, or
  in each case optionally substituted aryl, hetaryl, heterocycloalkyl, C$_1$-C$_6$ alkyl, C$_2$-C$_6$ alkenyl, C$_2$-C$_6$ alkynyl, C$_3$-C$_7$ cycloalkyl, C$_1$-C$_4$ alkylene-C$_3$-C$_7$ cycloalkyl, C$_1$-C$_4$ alkylene-heterocycloalkyl, C$_1$-C$_4$ alkylene-aryl, or C$_1$-C$_4$ alkylene-hetaryl, or in each case optionally substituted
    O—R$_{Z,Y}^4$, S—R$_{Z,Y}^4$, NR$_{Z,Y}^6$R$_{Z,Y}^7$, CO—OR$_{Z,Y}^5$, NR$_{Z,Y}^7$—CO—O—R$_{Z,Y}^5$, O—CH$_2$—COO—R$_{Z,Y}^5$, NR$_{Z,Y}^7$—CO—R$_{Z,Y}^5$, NR$_{Z,Y}^7$—CO—NR$_{Z,Y}^6$R$_{Z,Y}^5$, SO$_2$—R$_{Z,Y}^5$, NR$_{Z,Y}^7$—SO$_2$—R$_{Z,Y}^5$, NR$_{Z,Y}^7$—SO$_2$—NR$_{Z,Y}^6$R$_{Z,Y}^5$, SO$_2$NH$_2$, CONH$_2$, SO$_2$—NR$_{Z,Y}^6$R$_{Z,Y}^7$, or CO—NR$_{Z,Y}^6$R$_{Z,Y}^7$, or
  in each case two of the radicals selected from R$_{Z,Y}^1$, R$_{Z,Y}^2$, or R$_{Z,Y}^3$ form, together with the ring atoms bearing these substituents, a 3- to 7-membered saturated or unsaturated carbocycle which in each case is optionally substituted, or a saturated or unsaturated heterocycle which in each case is optionally substituted and which may contain one, two, or three further heteroatoms, which may be different or the same, selected from the group comprising O, N, and S, wherein optionally in each case two radicals substituted on this carbocycle or heterocycle together may form a 3- to 7-membered, anellated, saturated, unsaturated, or aromatic carbocycle or heterocycle optionally substituted in each case, wherein the heterocycle may contain one, two, or three heteroatoms, which may be different or the same, selected from the group comprising O, N, and S, and wherein the cyclic compound thus formed may optionally be substituted, and/or a further 3- to 7-membered, optionally substituted cyclic compound may be condensed thereon;

R$_{Z,Y}^4$ in each case is an optionally substituted C$_2$-C$_6$ alkenyl, C$_2$-C$_6$ alkynyl, C$_1$-C$_4$ alkylene-C$_3$-C$_7$ cycloalkyl, C$_1$-C$_4$ alkylene-heterocycloalkyl, heterocycloalkyl, hetaryl, aryl, C$_1$-C$_4$ alkylene-hetaryl, hetaryl, C$_1$-C$_4$ alkylene-aryl, or
  C$_1$-C$_6$ alkyl, which in each case is optionally substituted with a substituent from the group comprising halogen, NO$_2$, NH$_2$, OH, CN, CF$_3$, CHF$_2$, OCF$_3$, OCHF$_2$, optionally substituted NH—(C$_1$-C$_6$ alkyl), or optionally substituted N(C$_1$-C$_6$ alkyl)$_2$;

R$_{Z,Y}^6$ in each case is an optionally substituted C$_1$-C$_6$ alkyl, C$_2$-C$_6$ alkenyl, C$_2$-C$_6$ alkynyl, C$_3$-C$_7$ cycloalkyl, C$_1$-C$_4$ alkylene-C$_3$-C$_7$ cycloalkyl, C$_1$-C$_4$ alkylene-heterocycloalkyl, heterocycloalkyl, or C$_1$-C$_6$ alkylene-O—C$_1$-C$_6$ alkyl, dioxymethylenephenyl, benzofuranyl, dihydrobenzofuranyl, indanyl, or aryl or hetaryl which in each case is optionally singly, doubly, or triply substituted with substituents independently selected from the group comprising halogen, NO$_2$, NH$_2$, OH, CN, CF$_3$, CHF$_2$, OCF$_3$, OCHF$_2$, optionally substituted NH—(C$_1$-C$_6$ alkyl) or optionally substituted N(C$_1$-C$_6$ alkyl)$_2$, COOH, O—CH$_2$—COOH, SH, or
  in each case optionally substituted C$_1$-C$_6$ alkyl, C$_2$-C$_6$ alkenyl, C$_2$-C$_6$ alkynyl, C$_3$-C$_7$ cycloalkyl, C$_1$-C$_4$ alkylene-C$_3$-C$_7$ cycloalkyl, C$_1$-C$_4$ alkylene-heterocycloalkyl, aryl, hetaryl, heterocycloalkyl, C$_1$-C$_4$ alkylene-hetaryl, or C$_1$-C$_4$ alkylene-aryl, or in each case optionally substituted
    O—R$_A^1$, CO—R$_A^1$, S—R$_A^1$, SO—R$_A^1$, CO—O—R$_A^1$, NR$_A^4$—CO—O—R$_A^1$, O—CH$_2$—COO—R$_A^1$, NR$_A^2$R$_A^3$, CONH$_2$, SO$_2$NH$_2$, NR$_A^4$—CO—R$_A^1$, SO$_2$—R$_A^1$, NR$_A^4$—SO$_2$—R$_A^1$, SO$_2$—NR$_A^2$R$_A^3$, or CO—NR$_A^2$R$_A^3$;

R$_{Z,Y}^6$ is hydrogen, or
  in each case optionally substituted C$_1$-C$_6$ alkyl, C$_2$-C$_6$ alkenyl, C$_2$-C$_6$ alkynyl, C$_3$-C$_7$ cycloalkyl, C$_1$-C$_4$ alkylene-C$_3$-C$_7$ cycloalkyl, C$_1$-C$_4$ alkylene-heterocycloalkyl, aryl, hetaryl, heterocycloalkyl, C$_1$-C$_6$ alkylene-O—C$_1$-C$_6$ alkyl, CO—C$_1$-C$_6$ alkyl, C$_1$-C$_4$ alkylene-aryl, C$_1$-C$_4$ alkylene-hetaryl, CO-aryl, CO-hetaryl, CO—C$_1$-C$_4$ alkylene-aryl, CO—C$_1$-C$_4$ alkylene-hetaryl, CO—O—C$_1$-C$_6$ alkyl, CO—O-aryl, CO—O—C$_1$-C$_4$ alkylene-aryl, CO—O-hetaryl, CO—O—C$_1$-C$_4$ alkylene-hetaryl, CO—O—C$_1$-C$_4$ alkylene-aryl, SO$_2$—C$_1$-C$_6$ alkyl, SO$_2$-aryl, SO$_2$-hetaryl, SO$_2$—C$_1$-C$_4$ alkylene-aryl, or SO$_2$—C$_1$-C$_4$ alkylene-hetaryl;

R$_{Z,Y}^7$ is hydrogen or in each case optionally substituted C$_1$-C$_6$ alkyl, C$_2$-C$_6$ alkenyl, C$_2$-C$_6$ alkynyl, C$_3$-C$_7$ cycloalkyl, C$_1$-C$_4$ alkylene-C$_3$-C$_7$ cycloalkyl, C$_1$-C$_4$ alkylene-heterocycloalkyl, aryl, hetaryl, heterocycloalkyl, C$_1$-C$_6$ alkylene-O—C$_1$-C$_6$ alkyl, CO—C$_1$-C$_6$ alkyl, CO-aryl, CO-hetaryl, CO—C$_1$-C$_4$ alkylene-aryl, CO—C$_1$-C$_4$ alkylene-hetaryl, CO—O—C$_1$-C$_6$ alkyl, CO—O-aryl, CO—O—C$_1$-C$_4$ alkylene-aryl, CO—O-hetaryl, CO—O—C$_1$-C$_4$ alkylene-hetaryl, SO$_2$—C$_1$-C$_6$ alkyl, SO$_2$-aryl, SO$_2$-hetaryl, SO$_2$—C$_1$-C$_4$ alkylene-aryl, or SO$_2$—C$_1$-C$_4$ alkylene-hetaryl;

or the radicals R$_{Z,Y}^6$ and R$_{Z,Y}^7$ together with the nitrogen form a 3- to 7-membered saturated or aromatic heterocycle which is optionally substituted in each case and which may contain one, two, or three further heteroatoms, which may be different or the same, selected from the group comprising O, N, and S; and in each case two radicals substituted on this heterocycle together may optionally form a 3- to 7-membered anellated, saturated, unsaturated, or aromatic carbocycle or heterocycle optionally substituted in each case, wherein the heterocycle may contain up to three heteroatoms, which may be different or the same, selected from the group comprising O, N, and S, and the cyclic compound thus formed may optionally be substituted, and/or a further 3- to 7-membered, optionally substituted cyclic compound may be condensed thereon;

4.) A 5- or 6-membered aromatic heterocycle which may contain one, two, or three heteroatoms, which may be different or the same, selected from the group comprising O, N, and S, and which in each case may be substituted with $R_{Z,Y}^1$, $R_{Z,Y}^2$, and $R_{Z,Y}^3$ as defined above;

5.) A $C_5$-$C_{18}$ bi- or tricyclic saturated hydrocarbon radical which in each case is optionally substituted;

6.) $R^4$ and $R^6$ together with X and Y form an optionally substituted $C_6$-$C_{10}$-membered saturated, unsaturated, or aromatic carbocycle, preferably an optionally substituted benzo radical, which may be substituted in each case with one, two, or three radicals which are independently selected from $R_{Z,Y}^8$.

$R_{Z,Y}^8$: is hydrogen, $NO_2$, $NH_2$, OH, CN, $CF_3$, $CHF_2$, $OCF_3$, $OCHF_2$, COOH, O—$CF_{12}$—COOH, SH, halogen, or in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted
O—$R_{Z,Y}^4$, S—$R_{Z,Y}^4$, $NR_{Z,Y}^6R_{Z,Y}^7$, CO—$OR_{Z,Y}^5$, $NR_{Z,Y}^7$—CO—O—$R_{Z,Y}^5$, O—$CH_2$—COO—$R_{Z,Y}^5$, $NR_{Z,Y}^7$—CO—$R_{Z,Y}^5$, $SO_2$—$R_{Z,Y}^5$, $NR_{Z,Y}^7$—$SO_2$—$R_{Z,Y}^5$, $SO_2NH_2$, $CONH_2$, $SO_2$—$NR_{Z,Y}^6R_{Z,Y}^7$, or CO—$NR_{Z,Y}^6R_{Z,Y}^7$;

is provided for the treatment and/or prevention of, or for producing a medicament for the treatment and/or prevention of, and/or for the treatment and/or prevention of [sic], CNS diseases or CNS-related diseases.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, the use of at least one 5-ring heteroaromatic compound of general formula I as described above, and/or corresponding enantiomeric, diastereomeric, and/or tautomeric forms thereof, and/or pharmaceutically acceptable salts thereof, and/or active substance precursors ("prodrugs") thereof, wherein the radicals $R^1$, $R^2$, $R^3$, Q, W, X, Y, and Z are defined as stated above, is provided for the treatment and/or prevention of, and/or for producing a medicament for the treatment and/or prevention of, CNS diseases or CNS-related diseases.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, the use of at least one 5-ring heteroaromatic compound of general formula I as described above, and/or corresponding enantiomeric, diastereomeric, and/or tautomeric forms thereof, and/or pharmaceutically acceptable salts thereof, and/or active substance precursors ("prodrugs") thereof, wherein the radicals $R^1$, $R^2$, $R^3$, Q, W, X, Y, and Z are defined as stated above, is provided for the treatment and/or prevention of, and/or for producing a medicament for the treatment and/or prevention of, neuropathological, neuropsychiatric, and/or neurodegenerative disorders, symptoms, and/or dysfunctions.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, the use of at least one 5-ring heteroaromatic compound of general formula I as described above, and/or corresponding enantiomeric, diastereomeric, and/or tautomeric forms thereof, and/or pharmaceutically acceptable salts thereof, and/or active substance precursors ("prodrugs") thereof, wherein the radicals $R^1$, $R^2$, $R^3$, Q, W, X, Y, and Z are defined as stated above, is provided for the treatment and/or prevention of, and/or for producing a medicament for the treatment and/or prevention of, migraines and/or brain damage.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, the use of at least one 5-ring heteroaromatic compound of general formula I as described above, and/or corresponding enantiomeric, diastereomeric, and/or tautomeric forms thereof, and/or pharmaceutically acceptable salts thereof, and/or active substance precursors ("prodrugs") thereof, wherein the radicals $R^1$, $R^2$, $R^3$, Q, W, X, Y, and Z are defined as stated above, is provided for the treatment and/or prevention of, and/or for producing a medicament for the treatment and/or prevention of, neuropathological, neuropsychiatric, and/or neurodegenerative diseases selected from the group comprising cerebral ischemia, stroke, epilepsy, and attacks in general, psychoses, schizophrenia, autism, OCD syndrome, cognitive disorders, attention disorders, depression, bipolar and/or unipolar depression, anxiety, dementia, senile dementia, Alzheimer's dementia, demyelinating diseases, multiple sclerosis, and brain tumors.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, the use of at least one 5-ring heteroaromatic compound of general formula I as described above, and/or corresponding enantiomeric, diastereomeric, and/or tautomeric forms thereof, and/or pharmaceutically acceptable salts thereof, and/or active substance precursors ("prodrugs") thereof, wherein the radicals $R^1$, $R^2$, $R^3$, Q, W, X, Y, and Z are defined as stated above, is provided for the treatment and/or prevention of, and/or for producing a medicament for the treatment and/or prevention of, diseases selected from the group comprising cerebrovascular disorders, pain, pain-related disorders, dependency, drug-related disorders, amnesia, alcohol abuse, drug abuse, circadian rhythm disorders, and Cushing's syndrome.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, the use of at least one 5-ring heteroaromatic compound of general formula I as described above, and/or corresponding enantiomeric, diastereomeric, and/or tautomeric forms thereof, and/or pharmaceutically acceptable salts thereof, and/or active substance precursors ("prodrugs") thereof, wherein the radicals $R^1$, $R^2$, $R^3$, Q, W, X, Y, and Z are defined as stated above, is provided for the treatment and/or prevention of diseases which are modulated by 5-HT5 receptor activity, and/or for producing a medicament for the treatment and/or prevention of diseases which are modulated by 5-HT5 receptor activity.

Each of the above-referenced definitions of a variable may be combined with any given number of the above-referenced definitions of the remaining variables. This applies in particular for the combination of preferred definitions of a variable with any given or preferred definitions of the remaining variables.

According to a further aspect of the present invention, the use of at least one 5-ring heteroaromatic compound of general formula I as described above, and/or corresponding enantiomeric, diastereomeric, and/or tautomeric forms thereof, and/or pharmaceutically acceptable salts thereof, and/or active substance precursors ("prodrugs") thereof, wherein the radicals $R^1$, $R^2$, $R^3$, Q, W, X, Y, and Z are defined as stated above, is provided for the treatment and/or prevention of diseases which are modulated by 5-HT5 receptor activity, and/or for producing a medicament for the treatment and/or prevention of diseases which are modulated by 5-HT5 receptor activity, wherein the modulation of the 5-HT5 receptor activity is selected from the group comprising antagonization (antagonist), agonization (agonist), partial agonization (partial agonist), inverse agonization (inverse agonist), and partial inverse agonization (partial inverse agonist). Preferred are substances which have an antagonistic effect on the 5-HT5 receptor, i.e., antagonists or partial agonists. Antagonists of the 5-HT5 receptor are particularly preferred.

Within the context of the invention, the term "agonist" means a substance which produces an effect on the receptor (in this case, the 5-HT5 receptor) that is similar to the physiological ligands; "antagonist" means a substance which reduces or eliminates the biological effect of an agonist; "partial agonist" means a substance which produces a submaximal effect on the receptor, whereby in the absence of an agonist the partial agonist may have an agonistic effect, and in the presence of an agonist the partial agonist may have an antagonistic effect; "inverse agonist" means a substance which produces a negative effect; "competitive antagonist" means a substance which has affinity for the receptor, reversible binding to the receptor (competition for the agonist), and no intrinsic activity at the receptor (relative efficacy: ability of a substance to initiate an effect for the same receptor loading); and "noncompetitive antagonist" is a substance which has allosteric binding at the receptor and which influences the efficacy (and possibly the agonist binding) by means of a change in the receptor conformation.

According to a further aspect of the present invention, the use of at least one 5-ring heteroaromatic compound of general formula I as described above, and/or corresponding enantiomeric, diastereomeric, and/or tautomeric forms thereof, and/or pharmaceutically acceptable salts thereof, and/or active substance precursors ("prodrugs") thereof, wherein the radicals $R^1$, $R^2$, $R^3$, Q, W, X, Y, and Z are defined as stated above, is provided for the treatment and/or prevention of diseases, and/or for producing a medicament for the treatment and/or prevention of diseases which are modulated by 5-HT5 receptor activity, wherein the treatment and/or prevention is based on selectivity for the 5-HT5 receptor.

Each of the above-referenced definitions of a variable may be combined with any given number of the above-referenced definitions of the remaining variables. This applies in particular for the combination of preferred definitions of a variable with any given or preferred definitions of the remaining variable.

According to a further aspect of the present invention, the use of at least one 5-ring heteroaromatic compound of general formula I as described above, and/or corresponding enantiomeric, diastereomeric, and/or tautomeric forms thereof, and/or pharmaceutically acceptable salts thereof, and/or active substance precursors ("prodrugs") thereof, wherein the radicals $R^1$, $R^2$, $R^3$, Q, W, X, Y, and Z are defined as stated above, is provided for the treatment and/or prevention of, or for producing a medicament for the treatment and/or prevention of, diseases which are modulated by 5-HT5 receptor activity, wherein the treatment and/or prevention is based on selectivity for the 5-HT5 receptor, and the modulation of the 5-HT5A receptor activity is selected from the group comprising antagonization (antagonist), competitive antagonization (competitive antagonist), noncompetitive antagonization (mixed-type inhibition) (noncompetitive antagonist), agonization (agonist), partial agonization (partial agonist), inverse agonization (inverse agonist), and partial inverse agonization (partial inverse agonist). Preferred are substances having an antagonistic effect on the 5-HT5A receptor, i.e., antagonists or partial agonists. Antagonists of the 5-HT5A receptor are particularly preferred.

Each of the above-referenced definitions of a variable may be combined with any given number of the above-referenced definitions of the remaining variables. This applies in particular for the combination of preferred definitions of a variable with any given or preferred definitions of the remaining variable.

According to a further aspect of the present invention, the use of at least one 5-ring heteroaromatic compound of general formula I as described above, and/or corresponding enantiomeric, diastereomeric, and/or tautomeric forms thereof, and/or pharmaceutically acceptable salts thereof, and/or active substance precursors ("prodrugs") thereof, wherein the radicals $R^1$, $R^2$, $R^3$, Q, W, X, Y, and Z are defined as stated above, is provided for the treatment and/or prevention of, and/or for producing a medicament for the treatment and/or prevention of, diseases which are modulated by 5-HT5 receptor activity, and wherein the treatment and/or prevention is based on selectivity for the 5-HT5A receptor with a binding affinity (Ki) of less than or equal to 600 nM.

Each of the above-referenced definitions of a variable may be combined with any given number of the above-referenced definitions of the remaining variables. This applies in particular for the combination of preferred definitions of a variable with any given or preferred definitions of the remaining variable.

According to a further aspect of the present invention, the use of at least one 5-ring heteroaromatic compound of general formula I as described above, and/or corresponding enantiomeric, diastereomeric, and/or tautomeric forms thereof, and/or pharmaceutically acceptable salts thereof, and/or active substance precursors ("prodrugs") thereof, wherein the radicals $R^1$, $R^2$, $R^3$, Q, W, X, Y, and Z are defined as stated above, is provided for the treatment and/or prevention of, and/or for producing a medicament for the treatment and/or prevention of, diseases which are modulated by 5-HT5 receptor activity, and in which the treatment and/or prevention is based on selectivity for the 5-HT5A receptor with a binding affinity (Ki) of less than or equal to 600 nM, and the modulation of the 5-HT5A receptor activity is selected from the group comprising antagonization (antagonist), agonization (agonist), partial agonization (partial agonist), inverse agonization (inverse agonist), and partial inverse agonization (partial inverse agonist). Preferred are substances having an antagonistic effect on the 5-HT5A receptor, i.e., antagonists or partial agonists. Antagonists of the 5-HT5A receptor are particularly preferred.

Each of the above-referenced definitions of a variable may be combined with any given number of the above-referenced definitions of the remaining variables. This applies in particular for the combination of preferred definitions of a variable with any given or preferred definitions of the remaining variable.

According to one preferred embodiment, the use of at least one 5-ring heteroaromatic compound of general formula I as described above and the radicals $R^1$, $R^2$, $R^3$, Q, W, X, Y, and Z as stated above are defined, is provided, wherein the treatment and/or prevention is carried out in a human or nonhuman mammal.

Each of the above-referenced definitions of a variable may be combined with any given number of the above-referenced definitions of the remaining variables. This applies in particular for the combination of preferred definitions of a variable with any given or preferred definitions of the remaining variable.

DETAILED DESCRIPTION OF THE INVENTION

The radicals of formula I have the following meanings in preferred embodiments:

W is defined as above, and preferably represents W1.

A is located in the 2-position on the ring as defined above, and preferably stands for halogen, $NH_2$, CN, $CF_3$, $CHF_2$, $OCF_3$, $OCHF_2$, or in each case optionally substituted $O$—$C_1$-$C_6$ alkyl, $S$—$C_1$-$C_6$ alkyl, or in each case optionally substituted $O$—$R_A^1$, $S$—$R_A^1$, $O$—$CH_2$—$COO$—$R_A^1$, $NR_A^2R_A^3$, $SO_2NH_2$, $SO_2$—$R_A^1$, $NR_A^4$—$SO_2$—$R_A^1$, or $SO_2$—$NR_A^2R_A^3$.

A is particularly preferably F, Cl, $OCF_3$, $OCHF_2$, in each case optionally substituted $C_1$-$C_6$ alkyl, $O$—$C_1$-$C_6$ alkyl, or $S$—$C_1$-$C_6$ alkyl, or $O$—$R_A^1$;

A is more preferably F, Cl, $OCF_3$, $OCHF_2$, in each case optionally substituted $C_1$-$C_6$ alkyl, $O$—$C_1$-$C_6$ alkyl, O-benzyl, O-phenyl, or $S$—$C_1$-$C_6$ alkyl. Of these, most preferred for A are F, Cl, $OCF_3$, $OCHF_2$, $C_1$-$C_6$ alkyl, $O$—$C_1$-$C_6$ alkyl, or $S$—$C_1$-$C_6$ alkyl. A is most preferably methyl, $OCF_3$, $OCH_3$, O-ethyl, O-n-propyl, or O-isopropyl.

$R_A^1$ is defined as above, and preferably stands for $C_1$-$C_6$ alkyl, $C_3$-$C_7$ cycloalkyl, phenyl, or benzyl optionally substituted in each case. $R_A^1$ is more preferably methyl, ethyl, n-propyl, or isopropyl. $R_A^1$ is most preferably methyl or ethyl.

$R_A^2$ is defined as above, and preferably stands for hydrogen or $C_1$-$C_6$ alkyl, phenyl, benzyl, phenethyl, $CO$—$C_1$-$C_6$ alkyl, CO aryl, $CO$—$O$—$C_1$-$C_6$ alkyl, $SO_2$—$C_1$-$C_4$ alkyl, $SO_2$-aryl, $SO_2$-hetaryl, or $SO_2$—$C_1$-$C_4$ alkylene-aryl optionally substituted in each case.

$R_A^2$ is more preferably hydrogen, $C_1$-$C_6$ alkyl, phenyl, or benzyl.

In one embodiment $R_A^2$ is preferably hydrogen, methyl, ethyl, n-propyl, isopropyl, or phenyl.

$R_A^3$ is defined as above, and preferably stands for $C_1$-$C_6$ alkyl, phenyl, benzyl, phenethyl, $CO$—$C_1$-$C_6$ alkyl, CO-aryl, $CO$—$O$—$C_1$-$C_6$ alkyl, $SO_2$—$C_1$-$C_4$ alkyl, $SO_2$-aryl, $SO_2$-hetaryl, or $SO_2$—$C_1$-$C_4$ alkylene-aryl optionally substituted in each case.

$R_A^3$ is more preferably $C_1$-$C_6$ alkyl, phenyl, or benzyl, most preferably methyl, ethyl, n-propyl, or isopropyl, or phenyl.

As previously described, the two radicals $R_A^2$ and $R_A^3$ together with the nitrogen may also form a 3- to 7-membered heterocycle. The two radicals $R_A^2$ and $R_A^3$ together preferably form a 5- or 6-membered saturated or unsaturated ring which is optionally substituted in each case, and which may contain one or two further heteroatoms, which may be the same or different, from the group O, N, and S.

$R_A^4$ is defined as above, and preferably stands for hydrogen or an optionally substituted $C_1$-$C_6$ alkyl radical. $R_A^4$ is most preferably hydrogen, methyl, ethyl, n-propyl, or isopropyl.

B is defined as above, and preferably stands for hydrogen, halogen, CN, $CF_3$, $CHF_2$, $OCF_3$, $OCHF_2$, or in each case optionally substituted $C_1$-$C_6$ alkyl or $C_2$-$C_6$ alkenyl, $O$—$CH_2$—$COO$—$R_A^1$, $O$—$R_A^1$, $S$—$R_A^1$, $NR_A^2R_A^3$, $NR_A^4$—$CO$—$R_A^1$, or $CO$—$NR_A^4$—$R_A^1$.

B is particularly preferably hydrogen, halogen, OH, $OCF_3$, $OCHF_2$, in each case optionally substituted $C_1$-$C_6$ alkyl, $O$—$R_A^1$, or $S$—$R_A^1$.

B is more preferably hydrogen, halogen, $OCF_3$, $OCHF_2$, or in each case optionally substituted $C_1$-$C_6$ alkyl, $O$—$C_1$-$C_6$ alkyl, O-benzyl, O-phenyl, or $S$—$C_1$-$C_6$. Of these, B is more preferably hydrogen, F, Cl, $OCF_3$, $OCHF_2$, or in each case optionally substituted $C_1$-$C_6$ alkyl, $O$—$C_1$-$C_6$ alkyl, or $S$—$C_1$-$C_6$ alkyl. B is most preferably hydrogen, $OCF_3$, $OCH_3$, O-ethyl, O-n-propyl, or O-isopropyl.

B is preferably located in the 5- or 6-position on the ring, more preferably in the 6-position.

$R_w^1$ is defined as above, and preferably stands for hydrogen, F, Cl, CN, $CF_3$, $CHF_2$, $O$—$CF_3$, $OCHF_2$, or in each case optionally substituted $C_1$-$C_6$ alkyl, $O$—$C_1$-$C_6$ alkyl, aryl, $C_1$-$C_6$ alkylamino, or $C_1$-$C_6$ dialkylamino. $R_w^1$ is more preferably hydrogen, F, Cl, CN, $CF_3$, or $O$—$CF_3$, or O-Me, most preferably hydrogen.

$R_w^1$ is preferably located in the 4- or 5-position on the ring, more preferably in the 5-position.

For B and $R_w^1$ the condition preferably applies that when W=W1, $R_w^1$ and/or B is not an optionally substituted N-pyrrolidinyl radical in the 4-position (para position) with respect to the coupling position with Q;

D is defined as above, and preferably stands for halogen, OH, CN, $CF_3$, $CHF_2$, $OCF_3$, $OCHF_2$, or in each case optionally substituted $C_1$-$C_6$ alkyl or $C_2$-$C_6$ alkenyl, or $O$—$CH_2$—$COO$—$R_A^1$, $O$—$R_A^1$, $S$—$R_A^1$, $NR_A^2R_A^3$, $NR_A^4$—$CO$—$R_A^1$, or $CO$—$NR_A^4$—$R_A^1$.

D is particularly preferably halogen, OH, $OCF_3$, $OCHF_2$, in each case optionally substituted $C_1$-$C_6$ alkyl, $O$—$R_A^1$, or $S$—$R_A^1$.

D is more particularly preferably halogen, OH, $OCF_3$, $OCHF_2$, in each case optionally substituted $C_1$-$C_6$ alkyl, $O$—$C_1$-$C_6$ alkyl, O-benzyl, O-phenyl, or $S$—$C_1$-$C_6$ alkyl.

Of these, D is more preferably OH, F, Cl, $OCF_3$, $OCHF_2$, in each case optionally substituted $C_1$-$C_6$ alkyl, $O$—$C_1$-$C_6$ alkyl, or $S$—$C_1$-$C_6$ alkyl. D is most preferably OH, $OCF_3$, $OCH_3$, O-ethyl, O-n-propyl, or O-isopropyl.

D is preferably located in the 3- or 4-position on the ring, more preferably in the 3-position.

Overall, W preferably represents a radical which is composed of the preferred combinations of A, B, $R_A^1$, $R_A^2$, $R_A^3$, $R_A^4$, and $R_W^1$.

Q is defined as above, wherein the sum of the indices a, b, and c is equal to 1, 2, 3, 4, or 5, preferably 1, 2, or 3, more preferably 1 or 2. In particular a is 0, 1, 2, 3, or 4, preferably 1, 2, or 3, more preferably 1 or 2, most preferably 1. Index b is 0 or 1, preferably 0. Index c is 0, 1, 2, 3, or 4, preferably 0, 1, or 2, most preferably 0.

For the case that X=N, Y=$CR^4$, Z=$CR^6$, the sum of a, b, and c may also be 0.

Q is preferably $C_1$-$C_4$ alkylene or $C_1$-$C_4$ alkyleneoxy optionally substituted in each case, more preferably —$CH_2$—, —$CH_2$—O—, —$CH_2$—$CH_2$—, —$CH_2$—$CH_2$—$CH_2$—, or —$CH_2$—$CH_2$—O—, more preferably —$CH_2$—, —$CH_2$—O—, —$CH_2$—$CH_2$—, or —$CH_2$—$CH_2$—O—, most preferably —$CH_2$—.

$R_Q^1$, $R_Q^2$, $R_Q^3$, and $R_Q^4$ are defined as above, and preferably independently stand for hydrogen, halogen, OH, or optionally substituted $C_1$-$C_6$ alkyl, more preferably hydrogen, F, or $CH_3$. $R_Q^1$, $R_Q^2$, $R_Q^3$, and $R_Q^4$ most preferably are all hydrogen.

$V_Q$ is defined as above, and preferably stands for —CO—, —CO—$N_Z^5$—, —$NR_Z^5$—CO—, —O—, —S—, more preferably —O— or —S—, most preferably —O—.

$R_Q^5$ and $R_Q^{5*}$ are defined as above, and preferably independently stand for hydrogen or $CH_3$.

$R_Q^6$ and $R_Q^7$ are defined as above, and preferably independently stand for hydrogen or $CH_3$, most preferably hydrogen.

$R^1$, $R^2$ are defined as above, and preferably independently stand for hydrogen, OH, CN, or in each case optionally substituted $C_1$-$C_6$ alkyl, O—$C_1$-$C_6$ alkyl, O-aryl, $C_1$-$C_6$ alkylene-O—$C_1$-$C_6$ alkyl, substituted aryl, benzyl, CO—$C_1$-$C_6$ alkyl, CO-aryl, CO—$C_1$-$C_4$ alkylene-aryl, more preferably hydrogen, OH, CN, O-methyl, O-phenyl, acetyl, or benzoyl. It is particularly preferred that $R^1$ is hydrogen, and the second radical $R^2$ is hydrogen, OH, acetyl, or benzoyl, and most preferably all radicals $R^1$ and $R^2$ are hydrogen.

$R^3$ is hydrogen or a free electron pair,

X, Y, Z are defined as above, and preferably stand for X=N, Y=$CR^4$, Z=$CR^6$, or X=C, Y=$CR^4$, Z=$NR^7$, or X=N, Y=$NR^5$, Z=$CR^6$, or X=N, Y=N, Z=$CR^6$. It is particularly preferred that X=N, Y=$CR^4$, Z=$CR^6$, or X=C, Y=$CR^4$, Z=$NR^7$. It is likewise particularly preferred that X=N, Y=N, Z=$CR^6$. It is most preferred that X=N, Y=$CR^4$, Z=$CR^6$.

$R^4$, $R^5$, $R^6$, and $R^7$ may in each case be independently selected from one of groups 1-6, whereby the selection may basically be made from the same or different groups. The division by groups is only for improved clarity of the possible substituents, and does not represent a selection rank. Groups 1-6 are defined as above, and preferably have the following definitions:

For group 1.), $R^4$ and/or $R^6$ in each case preferably independently stand for a radical selected from the group comprising hydrogen, F, Cl, CN, $CF_3$, $CHF_2$, O—$CH_2$—COOH, or in each case optionally substituted $C_1$-$C_{10}$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, or $C_1$-$C_4$ alkylene-hetaryl. Hydrogen, $C_1$-$C_6$ alkyl, for example methyl, ethyl, n-propyl, isopropyl or tert-butyl, cyclopentyl or cyclohexyl, or $CF_3$ are particularly preferred.

For group 2.), $R^5$ and/or $R^7$ are a free electron pair or as defined above, preferably hydrogen, in each case optionally substituted $C_1$-$C_{10}$ alkyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, COO—$C_1$-$C_6$ alkyl, or $SO_2$—$R_{Z,Y}^5$, $SO_2NH_2$, $CONH_2$, $SO_2$—$NR_{Z,Y}^6R_{Z,Y}^7$, or CO—$N_{Z,Y}^6R_{Z,Y}^7$. Hydrogen, $C_1$-$C_6$ alkyl, for example, methyl, ethyl, n-propyl, isopropyl or tert-butyl, cyclopentyl or cyclohexyl, $SO_2$—$R_{Z,Y}^5$, $SO_2NH_2$, or $SO_2$—$NR_{Z,Y}^6R_{Z,Y}^7$ are particularly preferred.

For group 3.), $R^4$, $R^5$, $R^6$, and $R^7$ in each case preferably independently stand for a radical selected from the group comprising phenyl, 1-naphthyl, or 2-naphthyl, particularly preferably phenyl, in each case optionally substituted with $R_{Z,Y}^1$, $R_{Z,Y}^2$, and/or $R_{Z,Y}^3$.

$R_{Z,Y}^1$, $R_{Z,Y}^2$, and $R_{Z,Y}^3$ are defined as above, and in each case preferably independently stand for a substituent from the following group:

Hydrogen, $NO_2$, CN, $CF_3$, $CHF_2$, $OCF_3$, $OCHF_2$, O—$CH_2$—COOH, halogen, or in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted O—$R_{Z,Y}^4$, S—$R_{Z,Y}^4$, $NR_{Z,Y}^6R_{Z,Y}^7$, $NR_{Z,Y}^7$—CO—O—$R_{Z,Y}^5$, $NR_{Z,Y}^7$—CO—$R_{Z,Y}^5$, $SO_2$—$R_{Z,Y}^5$, $NR_{Z,Y}^7$—$SO_2$—$R_{Z,Y}^5$, $SO_2NH_2$, $SO_2$—$NR_{Z,Y}^6R_{Z,Y}^7$, or CO—$NR_{Z,Y}^6R_{Z,Y}^7$.

In one embodiment, hydrogen, CN, $CF_3$, $CHF_2$, $OCF_3$, $OCHF_2$, Cl, and F or in each case optionally substituted aryl, hetaryl, heterocycloalkyl, $C_1$-$C_6$ alkyl, $C_3$-$C_7$ cycloalkyl, O—$R_{Z,Y}^4$, $NR_{Z,Y}^6R_{Z,Y}^7$, or $NR_{Z,Y}^7$—$SO_2$—$R_{Z,Y}^6$ are preferred.

It is also possible that in each case two of the radicals from $R_{Z,Y}^1$, $R_{Z,Y}^2$, or $R_{Z,Y}^3$ together may form a 3- to 7-membered saturated or unsaturated carbocycle optionally substituted in each case, or may form a saturated or unsaturated heterocycle, optionally substituted in each case, which may contain one, two, or three further heteroatoms, which may be different or the same, from the group O, N, S.

In one embodiment, $R^4$ and $R^5$ are hydrogen or a free electron pair, $R^6$ and $R^7$ are phenyl, and $R_{Z,Y}^1$, $R_{Z,Y}^2$, or $R_{Z,Y}^3$ are preferably hydrogen in each case, or two of the substituents are hydrogen and the third substituent is a radical other than hydrogen, preferably CN or $NR_{Z,Y}^7$—$SO_2$—$R_{Z,Y}^5$.

$R_{Z,Y}^4$ is defined as above, and preferably stands for $C_1$-$C_4$ alkylene-$C_3$-$C_7$ cycloalkyl, $C_1$-$C_4$ alkylene-heterocycloalkyl, heterocycloalkyl, hetaryl, aryl, $C_1$-$C_4$ alkylene-hetaryl, hetaryl, $C_1$-$C_4$ alkylene-aryl optionally substituted in each case, or $C_1$-$C_6$ alkyl which is optionally substituted with a substituent from the group comprising halogen, $NO_2$, $NH_2$, OH, CN, $CF_3$, $CHF_2$, $OCF_3$, $OCHF_2$, optionally substituted NH—($C_1$-$C_6$ alkyl), and optionally substituted N($C_1$-$C_6$ alkyl)$_2$, most preferably methyl or ethyl, or $CH_2NH$—($C_1$-$C_6$ alkyl) or $CH_2N(C_1$-$C_6$ alkyl)$_2$;

$R_{Z,Y}^5$ is defined as above, and preferably stands for in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, heterocycloalkyl, or $C_1$-$C_6$ alkylene-O—$C_1$-$C_6$ alkyl, dioxymethylenephenyl, or aryl or hetaryl optionally singly to triply substituted in each case with substituents independently selected from the group comprising halogen, $NO_2$, $NH_2$, OH, CN, $CF_3$, $CHF_2$, $OCF_3$, $OCHF_2$, NH—($C_1$-$C_6$ alkyl), or N($C_1$-$C_6$ alkyl)$_2$, COOH, O—$CH_2$—COOH, SH, or in each case optionally substituted $C_1$-$C_6$ alkyl, $C_3$-$C_7$ cycloalkyl, aryl, hetaryl, or heterocycloalkyl, or each case optionally substituted O—$R_A^1$, S—$R_A^1$, $NR_A^4$—CO—O—$R_A^1$, O—$CH_2$—COO—$R_A^1$, $NR_A^2R_A^3$, $CONH_2$, $SO_2NH_2$, $SO_2$—$R_A^1$, $NR_A^4$—$SO_2$—$R_A^1$, or $SO_2$—$NR_A^2R_A^3$;

$R_{Z,Y}^5$ most preferably is methyl, ethyl, isopropyl, cyclohexyl, or aryl or hetaryl optionally singly, doubly, or triply substituted in each case with substituents independently selected from the group comprising halogen, $NH_2$, CN, $CF_3$, $CHF_2$, $OCF_3$, $OCHF_2$, optionally substituted NH—($C_1$-$C_6$ alkyl) or optionally substituted N($C_1$-$C_6$ alkyl)$_2$, or optionally substituted $C_1$-$C_6$ alkyl, or O—$R_A^1$, $NR_A^2R_A^3$, $SO_2NH_2$, $SO_2$—$R_A^1$, $NR_A^4$—$SO_2$—$R_A^1$, or $SO_2$—$NR_A^2R_A^3$;

$R_{Z,Y}^6$ is defined as above, and preferably stands for hydrogen, or in each case optionally substituted $C_1$-$C_6$ alkyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, $C_1$-$C_4$ alkylene-aryl, $C_1$-$C_4$ alkylene-hetaryl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, CO—O—$C_1$-$C_4$ alkylene-aryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl, more preferably hydrogen, or in each case optionally substituted $C_1$-$C_6$ alkyl, aryl, $C_1$-$C_4$ alkylene-aryl, $C_1$-$C_4$ alkylene-hetaryl, $SO_2$—$C_1$-$C_6$ alkyl, $SO_2$-aryl, $SO_2$-hetaryl, or $SO_2$—$C_1$-$C_4$ alkylene-aryl.

Of these, hydrogen, $C_1$-$C_6$ alkyl, phenyl, or benzyl are more preferable, and hydrogen, methyl, ethyl, or phenyl are most preferable.

$R_{Z,Y}^7$ is defined as above, and preferably stands for hydrogen or optionally substituted $C_1$-$C_6$ alkyl.

Hydrogen or methyl are more preferable.

It is likewise preferred that the two radicals $R_{Z,Y}^6$ and $R_{Z,Y}^7$ together with the nitrogen form a 3- to 7-membered saturated or unsaturated heterocycle which is optionally substituted in each case and which may contain one, two, or three further heteroatoms, which may be different or the same, from the group O, N, S;

More preferably, the two radicals $R_{Z,Y}^6$ and $R_{Z,Y}^7$ together with the nitrogen form an optionally substituted 5- or 6-membered saturated heterocycle which may contain a further heteroatom O, N, or S, preferably O or N. A 5-membered saturated heterocycle containing one N and a 6-membered saturated heterocycle containing two N or one N and one O are preferred.

For group 4.) the radicals $R^4$, $R^5$, $R^6$, and $R^7$ are defined as above, preferably a 5- or 6-membered aromatic heterocycle which may contain one, two, or three heteroatoms, which may be different or the same, from the group O, N, S, and which may be substituted in each case with $R_{Z,Y}^1$, $R_{Z,Y}^2$, and $R_{Z,Y}^3$.

Preferably, $R^4$ and/or $R^6$ in each case independently stand for a radical, optionally substituted in each case, selected from the group comprising 2-pyrrolyl, 3-pyrrolyl, benzothiophenyl, benzofuranyl, quinolinyl, isoquinolinyl, which in each case may be optionally substituted with one or two substituents; or 2-thienyl or 3-thienyl optionally substituted in each case with one or two substituents, wherein the substituents are selected from the group comprising halogen, in particular Cl, and —$NO_2$, —$NH_2$, —OH, —CN, —$CF_3$, —$OCF_3$, —$CHF_2$, O—$CHF_2$, or in each case optionally substituted $C_1$-$C_6$ alkyl, in particular methyl or ethyl, O—$C_1$-$C_6$ alkyl, NH—($C_1$-$C_6$ alkyl), and N($C_1$-$C_6$ alkyl)$_2$, NHCO—$C_1$-$C_6$ alkyl, $NHSO_2$—$C_1$-$C_4$ alkyl, and $SO_2$—$C_1$-$C_4$ alkyl.

It is particularly preferred that $R^4$ and/or $R^6$ in each case independently stand for benzothiophenyl, benzofuranyl, quinolinyl, isoquinolinyl, 2-thienyl, or 3-thienyl, optionally substituted in each case, wherein the two latter compounds are preferably substituted with halogen, in particular Cl, or $C_1$-$C_6$ alkyl, in particular methyl or ethyl.

In one embodiment, $R^4$ and/or $R^5$ in each case preferably independently stand for 2-pyridyl, 3-pyridyl, 4-pyridyl, 2-pyrimidyl, 4-pyrimidyl, 5-pyrimidyl, 6-pyrimidyl, 2-thienyl, 3-thienyl, benzothiophenyl, benzofuranyl, benzimidazolyl, quinolinyl, or isoquinolinyl, more preferably 2-pyridyl, 3-pyridyl, 4-pyridyl, 2-thienyl, 3-thienyl, benzothiophenyl, benzofuranyl, quinolinyl, or isoquinolinyl, which in each case may optionally be substituted with one or two radicals. The radicals are preferably selected from the group comprising halogen, in particular Cl or F, or —$NO_2$, —$NH_2$, —OH, —CN, —$CF_3$, —$OCF_3$, —$CHF_2$, O—$CHF_2$, $C_1$-$C_6$ alkyl, in particular methyl or ethyl, O—$C_1$-$C_6$ alkyl, NH—($C_1$-$C_6$ alkyl), and N($C_1$-$C_6$ alkyl)$_2$, NHCO—$C_1$-$C_6$ alkyl, $NHSO_2$—$C_1$-$C_4$ alkyl, and $SO_2$—$C_1$-$C_4$ alkyl, most preferably halogen, in particular Cl or F, or $C_1$-$C_6$ alkyl, in particular methyl or ethyl.

Particularly preferred are in each case optionally substituted 2-pyridyl, 3-pyridyl, 4-pyridyl, or 2-pyrimidyl, in particular 2-pyridyl, 3-pyridyl, or 4-pyridyl.

For group 5.), $R^4$, $R^5$, $R^6$, and $R^7$ preferably are optionally substituted adamantyl.

For group 6.) the radicals $R^4$ and $R^6$ are defined as above, and together with X and Y form a benzo radical, which may be substituted with one to three radicals which may be independently selected from the group $R_{Z,Y}^8$.

$R_{Z,Y}^8$: is defined as above, and preferably stands for hydrogen, $NH_2$, OH, $OCF_3$, $OCHF_2$, O—$CH_2$—COOH, SH, halogen, or in each case optionally substituted aryl, $C_1$-$C_6$ alkyl, $C_3$-$C_7$ cycloalkyl, or $C_1$-$C_4$ alkylene-aryl, or in each case optionally substituted O—$R_{Z,Y}^4$, S—$R_{Z,Y}^4$, $NR_{Z,Y}^6R_{Z,Y}^7$, $NR_{Z,Y}^7$—CO—$R_{Z,Y}^5$, $NR_{Z,Y}^7$—CO—$R_{Z,Y}^5$, $SO_2$—$R_{Z,Y}^5$, $NR_{Z,Y}^7$—$SO_2$—$R_{Z,Y}^5$, $SO_2NH_2$, $CONH_2$, $SO_2$—$NR_{Z,Y}^6R_{Z,Y}^7$, or CO—$NR_{Z,Y}^6R_{Z,Y}^7$.

The condition preferably applies that when $R^4$ and $R^6$ have the meanings given for group 6.), the radicals A, B, Q, $R_Q^1$, and $R_Q^2$ are defined as follows:

A is defined as in Claim 1 under $R_{Z,Y}^8$, and as stated in W1 is located in the 2-position with respect to Q and preferably stands for $OCF_3$, $OCHF_2$, O—$C_1$-$C_6$ alkyl, or O—$R_A^1$, S—$R_A^1$, $SO_2$—$R_A^1$. A preferably stands for F, Cl, $OCF_3$, $OCHF_2$, $C_1$-$C_6$ alkyl, O—$C_1$-$C_6$ alkyl, or S—$C_1$-$C_6$ alkyl. A most preferably stands for methyl, $OCF_3$, $OCH_3$, O-ethyl, O-n-propyl, or O-isopropyl.

B is defined as in Claim 1 under $R_{Z,Y}^8$, and is located in the 6-position with respect to Q and preferably stands for halogen, $CF_3$, $CHF_2$, $OCF_3$, $OCHF_2$, O—$C_1$-$C_6$ alkyl, S—$C_1$-$C_6$ alkyl, optionally substituted $C_1$-$C_6$ alkyl, or O—$R_A^1$, S—$R_A^1$. B preferably stands for F, Cl, $OCF_3$, $C_1$-$C_6$ alkyl, O—$C_1$-$C_6$ alkyl, or S—$C_1$-$C_6$ alkyl. B most preferably stands for F, Cl, methyl, $OCF_3$, $OCH_3$, O-ethyl, O-n-propyl, or O-isopropyl.

Q is defined as in Claim 1 under $R_{Z,Y}^8$, and preferably stands $CH_2$.

$R_Q^1$ and $R_Q^2$ are defined as in Claim 1 under $R_{Z,Y}^8$, and preferably independently stand for hydrogen and methyl. Most preferably, $R_Q^q$ and $R_Q^2$ are both hydrogen.

The two radicals $R^6$ and $R^7$ are preferably selected from groups 1.) through 4.), more preferably 1.) through 3.), including the preferred embodiments thereof, and the radicals $R^4$ and $R^5$ are selected from group 1.) or 2.), including the respective preferred embodiments thereof. The radical $R^4$ is methyl or hydrogen, and $R^5$ is preferably a free electron pair.

In one preferred embodiment the radical $R^6$ is selected from group 1.), including the preferred embodiments from group 1.), the radical $R^4$ is methyl or hydrogen, and $R^5$ is preferably a free electron pair.

In a further preferred embodiment the radical $R^6$ is selected from group 4.), including the preferred embodiments from group 4.), and the radical $R^4$ is methyl or hydrogen and $R^5$ is preferably a free electron pair.

In another preferred embodiment the radical $R^7$ is selected from group 2.), including the preferred embodiments from group 2.), and the radical $R^4$ is methyl or hydrogen and $R^5$ is preferably a free electron pair.

The above-described embodiments of each of the radicals, including the preferred embodiments, may be combined in any manner with the respective embodiments, including the preferred embodiments, of the other remaining radicals.

In the present invention the terms used have the meanings given below:

The term "alkyl" is equivalently applied to an unsubstituted or optionally substituted straight-chain or branched saturated hydrocarbon chain containing the respective stated number of carbon atoms, preferably 1, 2, 3, 4, 5, 6, 7, 8, 9, or 10 carbon atoms, particularly preferably 1, 2, 3, 4, 5, or 6, more preferably 1, 2, 3, or 4 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, n-hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, or 1-ethyl-2-methylpropyl, preferably methyl, ethyl, propyl, n-butyl, or isobutyl. The term "alkyl" is also intended to include halogen-substituted alkyl ("haloalkyl").

The term "alkylene" is equivalently applied to an unsubstituted or optionally substituted straight-chain or branched alkyl group as defined above, in which a hydrogen atom is replaced by a bond. Named in particular are methylene, 1,2-ethylene, 1,2-propylene, 1,3-propylene, 1,2-butylene, 1,3-butylene, 2,3-butylene, 1,4-butylene, 2-methyl-1,3-propylene, 1,2-pentylene, 1,3-pentylene, 1,4-pentylene, 1,5-pentylene, 2,3-pentylene, 2,4-pentylene, 1-methyl-1,4-butylene, 2-methyl-1,4-butylene, 2-methyl-1,3-butylene, 2-ethyl-1,3-propylene, 3,4-hexylene, 3-methyl-2,4-pentylene, 3,5-heptylene, 2-ethyl-1,3-pentylene, 3-ethyl-3,5-heptylene, etc., preferably methylene, 1,2-ethylene, and 1,2-propylene. The term "alkylene" is also intended to include halogen-substituted alkylene ("haloalkylene").

The term "cycloalkyl" is equivalently applied to an unsubstituted or optionally substituted branched or unbranched saturated hydrocarbon ring containing 3, 4, 5, 6, or 7, preferably 3, 4, 5, or 6, carbon atoms, such as cyclopropyl, cyclobutyl, cyclopentyl, cyclohexyl, or cycloheptyl. The term "cycloalkyl" is also intended to include halogen-substituted cycloalkyl ("halocycloalkyl").

The term "alkylene-O-alkyl" is equivalently applied to a straight-chain or branched saturated alkyl ether chain which is unsubstituted or optionally substituted in the alkylene and/or alkyl radical, containing a total of 2 to 12 carbon atoms and one oxygen atom, wherein the alkylene radical and the alkyl radical independently contain 1, 2, 3, 4, 5, or 6, more preferably 1, 2, 3, or 4, most preferably 1 or 2, carbon atoms, both radicals being defined as above. Preferred examples of alkylene-O-alkyl include methoxymethylene, ethoxymethylene, t-butoxymethylene, methoxyethylene, or ethoxyethylene. The term "alkylene-O-alkyl" is also intended to include halogen-substituted alkylene-O-alkyl in the sense of "haloalkylene-O-alkyl" or "alkylene-O-haloalkyl" or "haloalkylene-O-haloalkyl."

The term "thioalkyl" is equivalently applied to an unsubstituted or optionally substituted straight-chain or branched alkylene sulfanyl chain containing 1, 2, 3, 4, 5, or 6 carbon atoms and one sulfur atom. The alkylene radical preferably contains 1, 2, 3, or 4, more preferably 1 or 2, carbon atoms, where alkylene is defined as above. Examples of thioalkyl include thiomethyl or thio-tert-butyl. The term "thioalkyl" is also intended to include halogen-substituted thioalkyl ("halothioalkyl").

The term "alkenyl" is equivalently applied to an unsubstituted or optionally substituted branched or unbranched hydrocarbon chain having at least one double bond and containing 2, 3, 4, 5, or 6, preferably 2, 3, or 4, carbon atoms. The alkenyl preferably has one or two double bonds, most preferably one double bond. Examples of alkenyl groups include those stated above for alkyl, wherein these groups have one or two double bonds, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-entenyl, [sic; 3-methyl-4-pentenyl], 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl, and 1-ethyl-2-methyl-2-propenyl, in particular 2-propenyl, 2-butenyl, 3-methyl-2-butenyl, or 3-methyl-2-pentenyl. The term "alkenyl" is also intended to include halogen-substituted alkenyl ("haloalkenyl").

The term "alkynyl" is equivalently applied to an unsubstituted or optionally substituted branched or unbranched hydrocarbon chain having at least one triple bond and containing 2, 3, 4, 5, or 6, preferably 2, 3, or 4, carbon atoms. The alkynyl preferably has one or two triple bonds, most preferably one triple bond. Examples of alkynyl groups include those stated above for alkyl, wherein these groups have one or two triple bonds, for example ethynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl, and 1-ethyl-1-methyl-2-propynyl, preferably ethynyl, 2-propynyl, 2-butynyl, 1-methyl-2-propynyl, or 1-methyl-2-butynyl. The term "alkynyl" is also intended to include halogen-substituted alkynyl ("haloalkynyl").

The term "heterocycloalkyl" is equivalently applied to an unsubstituted or optionally substituted saturated alkyl ring, or an alkyl ring to which a further unsubstituted or optionally substituted saturated alkyl ring is anellated, preferably containing a total of 3, 4, 5, 6, 7, 8, 9, or 10 ring atoms, more preferably 3, 4, 5, or 6 ring atoms, most preferably 5 or 6 ring atoms, wherein this heterocycloalkyl contains at least one heteroatom, preferably 1, 2, or 3 heteroatoms, which may be the same or different, selected from the group comprising O, N, and S, and containing 1, 2, 3, 4, 5, or 6, preferably 1, 2, 3, 4, or 5, carbon atoms. The heterocycloalkyl preferably contains 1 or 2 heteroatoms, which may be the same or different, preferably selected from the group comprising N and O. Examples of a heterocycloalkyl group include N-pyrrolidinyl, N-piperidinyl, N-hexahydroazepinyl, N-morpholinyl, or N-piperazinyl, wherein for heterocycles which contain amino groups, for example N-piperazinyl, these amino groups may be substituted with common radicals, for example methyl, benzyl, Boc(tert-butoxycarbonyl), benzyloxycarbonyl, tosyl (p-toluenesulfonyl), —$SO_2$—$C_1$-$C_4$ alkyl, —$SO_2$-phenyl, or —$SO_2$-benzyl. The term "heterocycloalkyl" is also intended to include halogen-substituted heterocycloalkyl ("haloheterocycloalkyl").

The term "aryl" is equivalently applied to an unsubstituted or optionally substituted aromatic mono-, bi-, or polycyclic radical preferably containing 6, 7, 8, 9, 10, 11, 12, 13, 14, 15, 16, 17, 18, 19, or 20 carbon atoms, more preferably 6, 7, 8, 9, or 10 carbon atoms, and is preferably selected from phenyl, biphenyl, naphthyl, tetrahydronaphthyl, fluorenyl, indenyl, and phenanthrenyl, more preferably from phenyl and naphthyl, such as 1-naphthyl or 2-naphthyl. Phenyl is most preferred.

The term "alkylenearyl" is equivalently applied to optionally substituted aryl which is bonded by $C_1$-$C_6$ alkylene, more preferably $C_1$-$C_4$ alkylene, in the aryl and/or alkylene radical, whereby alkylene and aryl are defined as above. Alkylenearyl in particular is an optionally substituted benzyl or phenethyl in the aryl radical. The term "alkenylaryl" is also intended to include halogen-substituted alkenylaryl ("haloalkenylaryl").

The term "aryloxy" or "–O-aryl" is equivalently applied to an unsubstituted or optionally substituted aryl, defined as above, in particular —O-phenyl, which is bonded by oxygen.

The term "hetaryl" (or also "heteroaryl" or "heteroaromatic") is equivalently applied to an unsubstituted or optionally substituted mono-, bi-, or tricyclic aromatic ring containing at least one heteroatom, preferably 1, 2, or 3 heteroatoms which may be the same or different, more preferably 1 or 2 heteroatoms which may be the same or different, selected from the group comprising O, N, and S, and preferably containing 1, 2, 3, 4, 5, 6, 7, 8, 9, 10, 11, or 12, more preferably 1, 2, 3, 4, 5, or 6, carbon atoms. The aromatic ring is preferably a 5- or 6-membered ring. Hetaryl also includes the derivatives thereof anellated with aryl, namely, an aromatic radical preferably containing 6, 7, 8, 9, 10, 11, 12, 13, 14, 15, 16, 17, 18, 19, or 20 carbon atoms, more preferably 6, 7, 8, 9, or 10 carbon atoms, most preferably phenyl, which is anellated with this aromatic ring, which preferably contains at least one heteroatom. Hetaryl may also be selected from an aromatic radical preferably containing 6, 7, 8, 9, 10, 11, 12, 13, 14, 15, 16, 17, 18, 19, or 20, more preferably 6, 7, 8, 9, or 10, carbon atoms, most preferably phenyl, having a heterocycloalkyl group anellated thereto. The heterocycloalkyl group is defined as above.

Hetaryl is preferably selected from 2-furyl, 3-furyl, 2-pyrrolyl, 3-pyrrolyl, 2-thienyl, 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl, triazinyl, indolinyl, benzothienyl, naphthothienyl, benzofuranyl, chromenyl, indolyl, isoindolyl, indazolyl, quinolyl, isoquinolyl, phthalazinyl, quinoxalinyl, benzimidazolyl, and benzoxazolyl, 2,3-dihydro-1,4-benzodioxinyl, 1,3-benzodioxolyl, and 2,1,3-benzothiadiazolyl. The heterocycle may have one or more endo- or exocyclic double bonds ("unsaturated heterocycle"), or may be saturated ("saturated heterocycle"). The heterocycle may also be aromatic, whereby in the case of ring structures having multiple rings, in particular for anellated rings, the entire heterocycle or only one or more of its subrings may have an aromatic character ("aromatic heterocycle").

In the context of the present invention, the terms "pyridyl" and "pyridinyl" refer to the same radical. The same applies for "pyrimidyl" and "pyrimidinyl."

The term "alkylenehetaryl" refers to an optionally substituted hetaryl which is bonded by $C_1$-$C_6$ alkylene, more preferably $C_1$-$C_4$ alkylene, in the alkenyl and/or hetaryl radical, wherein alkylene and hetaryl are as defined herein.

Alkylenehetaryl is preferably optionally substituted —$CH_2$-2-pyridyl, —$CH_2$-3-pyridyl, —$CH_2$-4-pyridyl, —$CH_2$-2-thienyl, —$CH_2$-3-thienyl, —$CH_2$-2-thiazolyl, —$CH_2$-4-thiazolyl, $CH_2$-5-thiazolyl, —$CH_2$—$CH_2$-2-pyridyl, —$CH_2$—$CH_2$-3-pyridyl, —$CH_2$—$CH_2$-4-pyridyl, —$CH_2$—$CH_2$-2-thienyl, —$CH_2$—$CH_2$-3-thienyl, —$CH_2$—$CH_2$-2-thiazolyl, —$CH_2$—$CH_2$-4-thiazolyl, or —$CH_2$—$CH_2$-5-thiazolyl. The term "alkenylhetaryl" is also intended to include halogen-substituted alkenylhetaryl ("haloalkenylhetaryl").

The term "carbocycle" refers to an optionally substituted ring structure composed of carbon atoms as ring atoms. The ring structure is preferably mono-, bi-, or tricyclic or has a higher number of rings. The rings may be anellated or bridged. The number of carbon atoms in the ring is preferably between 3 and 12 C atoms, particularly preferably between 6 and 10 C atoms, as ring atoms. The ring structure may have one or more endo- or exocyclic double bonds ("unsaturated carbocycle"), or may be saturated ("saturated carbocycle"). The carbocycle may also be aromatic, whereby in the case of ring structures having multiple rings, in particular for anellated rings, the entire carbocycle or only one or more of its subrings may have an aromatic character ("aromatic carbocycle").

The term "cyclic compound" refers to an optionally substituted ring system selected from the group comprising "aryl," "hetaryl," "carbocycle," and "heterocycle."

A "bi- or tricyclic, saturated hydrocarbon radical" is an unsubstituted or optionally substituted bicycloalkyl or tricycloalkyl radical, and contains 5, 6, 7, 8, 9, 10, 11, 12, 13, 14, 15, 16, 17, or 18 carbon atoms. For a bicycloalkyl radical the ring system preferably contains 5, 6, 7, 8, 9, 10, 11, or 12, more preferably 6, 7, 8, 9, or 10, carbon atoms. For a tricycloalkyl radical the ring system preferably contains 6, 7, 8, 9, 10, 11, 12, 13, 14, 15, or 16, more preferably 6, 7, 8, 9, 10, 11, or 12, carbon atoms. Examples of a bicycloalkyl radical include indanyl, camphyl, and norbornyl. Examples of a tricycloalkyl radical include adamantyl.

"Halogen" refers to a halogen atom selected from fluorine, chlorine, bromine, or iodine, preferably fluorine, chlorine, or bromine, more preferably fluorine or chlorine, most preferably fluorine.

Halogen-substituted alkyl ("haloalkyl") refers to an alkyl radical as defined above which is partially or completed substituted by fluorine, chlorine, bromine, and/or iodine, for example $CH_2F$, $CHF_2$, $CF_3$, $CH_2Cl$, 2-fluoroethyl, 2-chloroethyl, 2,2,2-trifluoroethyl. This applies analogously to the terms "haloalkylene," "haloalkenyl," "haloalkynyl," "haloalkenylaryl," "haloalkenylhetaryl," "haloalkylene-O- alkyl," or "alkylene-O-haloalkyl," "haloalkylene-O-haloalkyl," "halothioalkyl," and "halocycloalkyl."

When the term "optionally substituted" is used, the radicals and groups may preferably be singly or multiply, more preferably singly, doubly, or triply, most preferably singly or doubly, substituted. The term "in each case optionally substituted" is intended to clarify that not only the radical directly following, but also all of the radicals named in the particular group may be substituted the same or differently.

Examples of suitable substituents for the terms "optionally substituted" or "in each case optionally substituted" include the following: halogen, CN, $CF_3$, $CHF_2$, $OCF_3$, $OCHF_2$, $NO_2$, $NH_2$, OH, COOH, in each case branched or unbranched, optionally substituted $C_1$-$C_6$ alkyl, $C_3$-$C_7$-cycloalkyl, $C_1$-$C_6$ alkylene-O—$C_1$-$C_6$ alkyl, or $C_1$-$C_6$ thioalkyl, O—$C_1$-$C_6$ alkyl, $N(C_1$-$C_6$ alkyl)($C_1$-$C_6$ alkyl), $NH(C_1$-$C_6$ alkyl), aryl, —O-aryl, $C_1$-$C_6$ alkylene-O-aryl, hetaryl, heterocycloalkyl, $C_1$-$C_4$ alkylene-aryl, $C_1$-$C_4$ alkylene-hetaryl, $C_1$-$C_4$ alkylene-$C_3$-$C_7$ cycloalkyl, $C_1$-$C_4$ alkylene-heterocycloalkyl, NHCO—$C_1$-$C_4$ alkyl, NH—$SO_2$—$C_1$-$C_4$ alkyl, CO—$C_1$-$C_6$ alkyl, COO—$C_1$-$C_6$ alkyl, O—CO—$C_1$-$C_6$ alkyl, $SO_2$—$C_1$-$C_6$ alkyl, and NHCO-aryl, $NHSO_2$-aryl, $CONH_2$, $SO_2NH_2$, $SO_2$-aryl, SO—$C_1$-$C_6$ alkyl, $SO_2$—$C_1$-$C_6$ alkyl, SO-aryl, N-pyrrolidinyl, N-piperidinyl, and N-morpholinyl optionally substituted in the aryl radical. Preferred substituents are F, Cl, $CF_3$, $OCF_3$, $NH_2$, $NO_2$, OH, COOH, $C_1$-$C_4$ alkyl, methoxy, acetyl, NH-acetyl, and $SO_2NH_2$.

The prefix "$C_1$-$C_6$" means that the subsequently named radical, for example the radical "alkyl" in "$C_1$-$C_6$ alkyl," may contain 1, 2, 3, 4, 5, or 6 carbon atoms. The same analogously applies to the meaning of the other prefixes used in the present patent specification and the claims, for example "$C_3$-$C_7$" (3, 4, 5, 6, or 7 carbon atoms), "$C_1$-$C_4$" (1, 2, 3, or 4 carbon atoms), "$C_2$-$C_6$" (2, 3, 4, 5, or 6 carbon atoms), etc.

The term "3- to 7-membered" carbocycle, heterocycle, or ring refers to the total number of ring members, i.e., to a ring containing a total of 3, 4, 5, 6, or 7 ring members. In the case of ring systems anellated to one another, whereby "anellated" may mean neighboring (vicinal) as well as geminal (spriro-bridged ring systems), the term "3- to 7-membered" means the total number of ring members, including the ring members which are part of the neighboring anellated ring system. The same analogously applies for the terms "5- to 7-membered," "5- or 6-membered," "4- to 7-membered," etc.

In general, a radical placed in parentheses, for example, the radical "($C_1$-$C_6$ alkyl)" in the term "$N(C_1$-$C_6$ alkyl)$_2$," together with a numerical value associated with the expression in parentheses refers to the multiple occurrence, corresponding to the numerical value, of the particular radical, i.e., in the case of the above-referenced example stands for a radical "$N(C_1$-$C_6$ alkyl)($C_1$-$C_6$ alkyl)," wherein the multiply occurring radicals in each case may independently have the same or different meanings. The same analogously applies for all expressions according to the scheme "(radical)$_x$," where x is an integer equal to or greater than two.

Optical Isomers—Diastereomers—Geometric Isomers—Tautomers

The compounds of general formula I according to the invention or the salts thereof may have at least one asymmetrical center, and may be present as racemates and racemic mixtures, individual enantiomers, diastereomeric mixtures, and individual diastereomers. The present invention encompasses all of these stereoisomeric forms of the compounds of general formula I according to the invention.

The compounds of general formula I according to the invention may be split into their individual stereoisomers by use of customary methods, for example fractional crystallization from a suitable solvent such as methanol or ethyl acetate or a mixture thereof, or by chiral chromatography, using an optically active stationary phase. The absolute configuration may be determined by X-ray crystallography of the crystalline products or crystalline intermediate products which, if necessary, may be derivatized using a reactant containing an asymmetrical center having a known absolute configuration.

Alternatively, any given stereoisomer of a compound of general formula I according to the invention may be obtained by stereospecific synthesis, using optically pure starting materials or reactants having a known absolute configuration, or by use of asymmetrical synthesis methods.

Use of an enantiomerically or diastereomerically pure compound is preferred.

In particular, the compounds of general formula I according to the invention may also be present in the form of various tautomers, it being obvious to one skilled in the art that the type of tautomerism depends on the nature of the radicals. Other tautomers such as keto enol tautomers may also be present. All of the individually possible tautomers as well as mixtures thereof are encompassed by the compounds of general formula I according to the invention.

Salts

The term "pharmaceutically acceptable salts" refers to salts that are prepared from pharmaceutically acceptable, physiologically tolerable bases or acids, including inorganic or organic bases and inorganic or organic acids.

Salts that are derived from inorganic bases contain aluminum, ammonium, calcium, copper, iron(II), iron(III), lithium, magnesium, manganese, potassium, sodium, zinc, and the like. Particularly preferred are the ammonium, calcium, lithium, magnesium, potassium, and sodium salts derived from pharmaceutically acceptable organic, nontoxic bases, and include salts of primary, secondary, and tertiary amines, substituted amines, including naturally occurring substituted amines, cyclic amines, and basic ion exchange resins such as arginine, betaine, caffeine, choline, N,N'-dibenzylethylenediamine, diethylamine, 2-diethylaminomethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purine, theobromine, triethylamine, trimethylamine, tripropylamine, tromethamine, and the like.

When the compounds of general formula I according to the invention are basic, salts of pharmaceutically acceptable, physiologically tolerable acids, including inorganic and organic acids, may be prepared. Such acids include, among others, acetic acid (acetate), benzenesulfonic acid, benzoic acid, camphorsulfonic acid, citric acid, ethanesulfonic acid, formic acid, fumaric acid, gluconic acid, glutaminic acid, hydrobromic acid, hydrochloric acid, lactic acid, malic acid, maleic acid, mandelic acid, methanesulfonic acid, malonic acid, nitric acid, pantothenic acid, phosphoric acid, propionic acid, succinic acid, sulfuric acid, tartaric acid, p-toluenesulfonic acid, trifluoroacetic acid, and the like. Acetic acid, citric acid, fumaric acid, hydrobromic acid, hydrochloric acid, maleic acid, phosphoric acid, sulfuric acid, and malic acid are particularly preferred.

When reference is made to the compounds of general formula I according to the invention, this is intended to mean that the pharmaceutically acceptable salts thereof are also included.

When reference is made to the compounds of general formula I according to the invention, this is intended to mean that the active substance precursors ("prodrugs") thereof are also included. "Prodrugs" are understood to mean derivatives of the compounds of general formula I according to the invention which under the physiological, including the physical, thermal, chemical, or enzymatic, conditions are converted to the compounds of general formula I according to the invention after administration to a patient, preferably a human or nonhuman mammal.

Use, Fields of Application, and Effects

The subject matter of the invention also concerns the use of 5-ring heteroaromatic compounds of formula I or IA for the treatment of:

Depression and/or bipolar disorders, for example dysthymic disorders, seasonally related disorders, and/or psychotic disorders Anxiety and/or stress-related disorders, for example general anxiety disorders, panic attacks, compulsive disorders, post-traumatic stress disorders, acute stress disorders, and/or social phobias Memory disorders and/or Alzheimer's disease Schizophrenia, psychoses, psychotic disorders, and/or psychosis-related disorders Cerebrovascular disorders Pain and/or pain-related disorders, dependency and drug-related disorders, including medication-related disorders Amnesia Alcohol and/or drug abuse, including medication abuse Circadian rhythm disorders and/or Cushing's syndrome.

The term "disorder" in the sense of the invention refers to anomalies which are generally regarded as medical conditions and which may be identified by virtue of specific signs, symptoms and/or dysfunctions. The treatment may be directed to individual disorders, i.e., anomalies or medical conditions, or multiple anomalies which may be etiologically associated can also be combined into patterns, i.e., syndromes, which may be treated according to the invention. This state may be transient, progressive, or persistent.

Compounds of the present invention may be used for the treatment or prevention of various diseases for which 5-HT5 receptors are involved in the origin and/or progression thereof, i.e., diseases which are modulated by 5-HT5 receptor activity, such as mental disorders. Examples of such mental disorders include those [classified] in the American Psychiatric Association DSM-IV, Diagnostic and Statistical Manual of Mental Disorders, 4th edition, 1994: Attention disorders and socially disruptive behavior; learning disabilities, delirium, dementia, and amnesiac and other cognitive disorders; disorders relating to various substances, for example disorders relating to alcohol consumption and alcohol-induced disorders, withdrawal symptoms; schizophrenia and other psychotic disorders, for example schizoid disorders, schizoaffective disorder, and delusional disorder; substance-induced psychoses; paranoid disorders; disorders induced by neuroleptic agents; affective disorders, for example depressive disorders (major depression, dysthymic disorder, seasonally related disorders, depressive disorders not further classified), bipolar disorders (bipolar I disorder, bipolar II disorder, cyclothymic disorder, bipolar disorders not further classified, substance-induced affective disorder (amphetamine or amphetamine-like substances), affective disorders not further classified); stress-related disorders, for example acute traumatic stress; anxiety disorders, for example panic attacks without agoraphobia, attacks with agoraphobia, agoraphobia without a previous history of panic attacks, specific phobias, social phobias, compulsive disorder, post-traumatic stress disorder, acute traumatic stress disorder, generalized anxiety, substance-induced anxiety; somatoform disorders, for example somatic disorder, somatic disorders not further classified, conversion disorder, pain disorder, eating disorders; sleep disorders, for example primary sleep disorders (dyssomnia, parasomnia), sleep disorders in conjunction with another mental disorder.

The subject matter of the invention in particular also concerns the use of the 5-ring heteroaromatic compounds I for the treatment of neuropathological, neuropsychiatric, and neurodegenerative disorders.

Neuropathological disorders are understood to be disorders that are accompanied by neurological deficits, i.e., a condition characterized by neurological symptoms.

The treatment of neurodegenerative and/or neuropsychiatric disorders is preferred according to the invention. These disorders occur in particular in neuropathological medical conditions which as a rule cause brain damage, for example cerebral ischemia, stroke, epilepsy, and attacks in general, chronic schizophrenia, other psychotic conditions, depression, anxiety, bipolar disorders, dementia, in particular Alzheimer's dementia, demyelinating diseases, in particular multiple sclerosis, brain tumors, and general inflammatory processes. Migraines and the associated signs, symptoms and dysfunctions represent a further neuropathological disorder.

According to a further aspect of the present invention, neuropathological disorders which are accompanied by a glial reaction are treated. The use according to the invention relates in particular to the modulation of a glial reaction. One advantageous effect of the binding partners is shown for the preventative or acute treatment of neurological deficits, which are observed in patients with psychiatric conditions such as epilepsy, psychosis, for example psychoses of the acute exogenous reaction type, or accompanying psychoses of organic or exogenous origin, such as those following trauma, primarily brain lesions and diffuse brain damage, for metabolic disorders, infections, and endocrinopathy; endogenous psychoses such as schizophrenia and schizoid and delusional disorders; affective disorders, such as depressive, manic, or manic-depressive states; and mixed forms of the previously described psychoses; senile dementia and Alzheimer's-type senile dementia, and in the treatment or prevention of demyelination processes.

The 5-ring heteroaromatic compounds according to the invention are particularly effective for the treatment of ischemic conditions, for example as the result of brain and spinal cord trauma, as well as vascular occlusion or heart failure. Noted in particular is stroke (synonyms: apoplexia cerebri, cerebral or apoplectic stroke, cerebrovascular accident). Conditions which may be treated according to the invention include transitory ischemic attacks, reversible ischemic neurological deficits, prolonged reversible ischemic neurological deficits, partially reversible ischemic neurological symptoms, and persistent complete cerebral infarctions. The treatment of acute forms according to the invention is particularly advantageous.

The forms of neuropathological disorders preferably treated according to the invention are based on one or more of the following listed changes in the nerve tissues: Degeneration or death of neurons, in particular of ganglocytes, for example tigrolysis, nuclear membrane blurring, cell shrinkage, cytoplasmic vacuolation and encrustation, cerebral parenchymal necroses, cerebral edemas, neuronal changes caused by oxygen deficiency, atrophy, morphological changes such as demyelination, in particular myelin sheath degeneration, perivascular infiltrates, glial proliferation and/or glial scars; degeneration of the substantia nigra.

The indication to be treated according to the invention is frequently characterized by a progressive development; i.e., the above-described states change over time, generally with increased severity, it being possible for states to intermerge, or for states to occur in addition to the existing states. As the result of treatment according to the invention of neuropathological, neuropsychiatric, or neurodegenerative disorders or their underlying conditions, a number of additional signs, symptoms, and/or dysfunctions may be treated which are associated with these disorders, i.e., which in particular accompany the above-described medical conditions. These include, for example, shock lung; cranial nerve deficits, for example retrobulbar neuritis, paralysis of the ocular muscles, staccato speech, spastic paralyses, cerebellar symptoms, sensitivity disorders, bladder and rectal disorders, euphoria, dementia; hypokinesis and akinesis, absence of synkinesis, shuffling gait, bent posture of trunk and limbs, pro-, retro-, and lateropulsion, tremors, lack of facial expression, monotonous speech, depression, apathy, labile or rigid affectivity, deficient spontaneity and resolution, slowing of thought, reduced association ability; muscular atrophy.

Treatment in the sense of the invention encompasses not only the treatment of acute or chronic signs, symptoms, and/or dysfunctions, but also preventative treatment (prophylaxis), in particular as recidivism or phase prophylaxis. The treatment may be directed to symptoms, for example as symptom suppression. The treatment may be oriented toward short- or medium-term measures, or it may also be a long-term treatment, for example within the scope of maintenance therapy.

The term "binding partner for 5-HT5 receptors" describes substances which bind to 5-HT5 receptors, and which therefore may also be referred to as 5-HT5 receptor ligands.

"Binding" is understood as the molecular interaction between the binding partner and the receptor, in particular under physiological conditions. These are generally classical interactions which include electrostatic attraction, hydrogen bridge bonding, hydrophobic bonds, van der Waals forces, or metal complex-like coordinative bonds. In addition to the above-referenced reversible molecular interactions, irreversible interactions between binding partner and receptor are also possible, such as covalent bonds.

Five-ring heteroaromatic compounds according to the invention are able to competitively inhibit the binding of comparison binding partners such as 5-HT (5-hydroxytryptamine) or 5-CT (5-carboxamidotryptamine) to 5-HT5 receptors. Competitive inhibition is understood to mean that the compounds of formula I according to the invention compete with a comparison binding partner, in the present case 5-HT or 5-CT, for example, for the binding to the receptor.

According to a further embodiment, 5-ring heteroaromatic compounds according to the invention noncompetitively inhibit the binding of comparison binding partners, such as 5-HT (5-hydroxytryptamine) or 5-CT (5-carboxamidotryptamine), to 5-HT5 receptors. Noncompetitive inhibition is understood to mean that 5-ring heteroaromatic compounds according to the invention by means of their binding to the receptor modulate the binding of a comparison binding partner, in the present case 5-HT or 5-CT, for example, and in particular reduce its binding affinity.

At least for the case of competitive inhibition, i.e., reversible binding, the principle applies that the displacement of one binding partner by another increases with decreasing binding affinity of the one binding partner, i.e., increasing binding affinity of the other binding partner with respect to the receptor. Therefore, it is practical for 5-ring heteroaromatic compounds according to the invention to have a high binding affinity for 5-HT5 receptors. Such a binding affinity on the one hand allows an effective displacement of naturally occurring binding partners for 5-HT5 receptors, for example serotonin (5-hydroxytryptamine, 5-HT) itself, whereby the concentration of the 5-ring heteroaromatic compound according to the invention necessary for binding a given quantity of this binding partner to 5-HT5 receptors decreases with increasing binding affinity. With respect to medical use, 5-ring heteroaromatic compounds are therefore preferred whose binding affinity is so great that these may be administered in justifiable quantities as an active substance within the scope of an effective medical treatment.

The competition experiments referenced above, according to which the concentration of the 5-ring heteroaromatic compounds according to the invention which suppresses 50% of the other comparison binding partner from the receptor binding site (IC50-values) is determined in vitro, offers one possibility for expressing the binding affinity. Thus, the competitive inhibition of the binding of 5-CT to 5-HT5 receptors is evaluated in such a way that preferred 5-ring heteroaromatic compounds according to the invention have half-maximal IC50 inhibition constants of less than $10^{-5}$ M, preferably less than $10^{-6}$ M, and in particular less than $10^{-7}$ M. The binding affinity of 5-ring heteroaromatic compounds according to the invention may also be expressed by means of the inhibition constant Ki, which generally is likewise determined in vitro by means of competition experiments. For binding to 5-HT5 receptors, 5-ring heteroaromatic compounds according to the invention preferably have Ki values of less than $10^{-6}$ M, advantageously less than $10^{-7}$ M, and particularly preferably less than $10^{-8}$ M.

Binding partners which may be used are able to bind to 5-HT5 with an affinity that is less than, essentially the same as, or greater than that for a given receptor other than 5-HT5. Thus, binding partners for 5-HT5 receptors with regard to use according to the invention are in particular those whose binding affinity for 5-HT5 receptors compared to the affinity for 5-HT receptors is so high that they are advantageously suited for use according to the invention. This does not necessarily assume a comparatively more selective binding to 5-HT5 receptors, although selective binding partners for 5-HT5 receptors are a preferred embodiment of the present invention.

For example, binding partners may be used which have high affinity for 5-HT5 as well as for other 5-HT receptors. In this context, "high affinity" means Ki values which generally range from $1 \cdot 10^{-10}$ M to $1 \cdot 10^{-6}$ M. According to one particular embodiment, 5-ring heteroaromatic compounds according to the invention have a binding profile in the high-affinity range for 5-HT receptors which is characterized by a binding affinity for 5-HT5 which in comparison to other binding affinities in this range is essentially the same or only slightly lower. Factors of 10 or less may be advantageous.

Five-ring heteroaromatic compounds according to the invention have binding affinities for 5-HT5 receptors which are greater than those for one or more 5-HT receptors other than 5-HT5, i.e., in particular receptors associated with the above-mentioned 5-HT receptor classes 5-HT1, 5-HT2, 5-HT3, 5-HT4, 5-HT6, and 5-HT7. If the binding affinity of a binding partner for 5-HT5 receptors is greater than that for a 5-HT receptor other than 5-HT5, the binding of this binding partner to 5-HT5 receptors is referred to as selective binding with respect to a 5-HT receptor other than 5-HT5. Special binding partners are those whose binding affinity for 5-HT5 receptors is greater than that for at least one 5-HT receptor. Five-ring heteroaromatic compounds whose binding affinity for 5-HT5 receptors is greater than that for all 5-HT receptors other than 5-HT5 represent a further special class of 5-ring heteroaromatic compounds according to the invention.

Selectivity is understood as the property of a binding partner to preferentially bind to 5-HT5 receptors. For the selectivity described above, it is crucial that there is an adequate difference between the binding affinities for 5-HT5 receptors and the binding affinities for one or more 5-HT receptors other than 5-HT5. Affinity differences are preferred for which the binding affinity ratio is at least 2, advantageously at least 5, particularly advantageously at least 10, preferably at least 20, particularly preferably at least 50, and most particularly preferably at least 100.

According to a further embodiment, 5-ring heteroaromatic compounds according to the invention bind selectively to 5-HT5 receptors having the above-described advantageous binding affinities with respect to one or more 5-HT receptors other than 5-HT5.

According to a further embodiment, 5-ring heteroaromatic compounds according to the invention bind selectively to 5-HT5 receptors having the above-described advantageous binding affinities with respect to all 5-HT receptors other than 5-HT5.

Particularly advantageous are 5-ring heteroaromatic compounds of formula I which bind with the above-described affinities and selectivities to 5-HT5 receptors which are expressed by glia cells and in particular by astrocytes. According to the invention, the human receptor variant is a preferred target for the 5-ring heteroaromatic compounds according to the invention.

The binding of 5-ring heteroaromatic compounds according to the invention to 5-HT5 receptors is coupled to an effector function. Binding partners may act agonistically or antagonistically, as well as partially agonistically and/or partially antagonistically. According to the invention, compounds which completely or partially mimic the activity of 5-HT on 5-HT5 receptors are referred to as agonists. Five-ring heteroaromatic compounds according to the invention which are able to block the agonistic activity of 5-HT on 5-HT5 receptors are referred to as antagonists.

According to one preferred embodiment of the present invention, 5-ring heteroaromatic compounds are used whose binding at least to 5-HT5 receptors of h5-HT5-transfected CHO, HEK 293, or SHSY-5Y cells brings about a change in the agonist-induced stimulation of GTP binding to membrane-bound G proteins, a change in intracellular calcium levels, a change in the agonist-induced induction of phospholipase C activity, and/or a change in cAMP production. With regard to the change in intracellular calcium levels, the use of 5-ring heteroaromatic compounds which bring about an increase in intracellular calcium levels represents a preferred embodiment of the invention. This embodiment also includes 5-ring heteroaromatic compounds which are active in known animal models for neurodegenerative and neuropsychiatric processes.

Preferred are 5-ring heteroaromatic compounds which are also selective for 5-HT5 receptors with respect to their effector function in the sense described above.

Administration Forms and Formulation

On account of their pharmacological properties, the 5-ring heteroaromatic compounds according to the invention may be used as active substances for therapeutic purposes. The 5-ring heteroaromatic compounds according to the invention are preferably brought into a suitable administration form before administration. Therefore, the subject matter of the present invention is also concerned with compositions, in particular pharmaceutical compositions, containing at least one 5-ring heteroaromatic compound according to the invention and a pharmaceutically acceptable carrier or diluent.

Carriers or adjuvants which are known for use in the field of pharmacy and related fields, in particular those listed in relevant pharmacopoeias (for example, DAB (Deutsches Arzneimittelbuch), Ph. Eur. (Pharmacopoeia Europaea), BP (Baccalaureus Pharmaciae), NF (National Formulary), USP (United States Pharmacopoeia), as well as other carriers having properties that are compatible with physiological use are pharmaceutically acceptable.

Suitable carriers and adjuvants may be the following: wetting agents; emulsifying and suspending agents; preservatives; antioxidants; anti-irritants; chelate-forming agents; dragee adjuvants; emulsion stabilizers; film-forming agents; gel-forming agents; odor masking agents, flavorants; resins; hydrocolloids; solvents; solubilizers; neutralizing agents; permeation accelerators; pigments; quaternary ammonium compounds; emollients and moisturizers; salve, creme, or oil bases; silicone derivatives; spreading agents; stabilizers; sterilizers; suppository bases; tabletting adjuvants such as binders, fillers, lubricants, disintegrants, or coatings; propellants; drying agents; opacifiers; thickeners; waxes; softeners; and white oils. This type of formulation is based on technical knowledge as described, for example, in Fiedler, H. P., Lexikon der Hilfsstoffe für Pharmazie, Kosmetik and angrenzende Gebiete [Lexicon of Adjuvants for Pharmacy, Cosmetics, and Related Fields], 4th Edition, Aulendorf: ECV-Editio-Kantor-Verlag, 1996.

Examples of suitable carriers and diluents include lactose, dextrose, sucrose, sorbitol, mannitol, starches, gum acacia, calcium phosphate, alginate, gum tragacanth, gelatin, calcium silicate, microcrystalline cellulose, polyvinyl pyrrolidone, cellulose, water syrup, methylcellulose, methyl- and propylhydroxybenzoates, talcum, magnesium stearate, and mineral oil.

The 5-ring heteroaromatic compounds according to the invention may be formulated to ensure immediate or delayed release of the active substance to the patient.

Examples of suitable pharmaceutical compositions include solid dosage forms such as meals, powders, granulates, tablets, in particular film tablets, lozenges, sachets, cachets, dragees, capsules such as hard and soft gelatin capsules, suppositories or vaginal dosage forms, semisolid dosage forms such as salves, cremes, hydrogels, pastes, or plasters, and liquid dosage forms such as solutions, emulsions, in particular oil-in-water emulsions, suspensions, for example lotions, injection and infusion preparations, and eye drops and ear drops. Implanted dispensing devices may also be used to administer the 5-ring heteroaromatic compounds according to the invention. Liposomes or microspheres may also be used.

The compositions according to the invention may be administered, for example, using customary methods.

In the preparation of the compositions according to the invention, the active substances are usually mixed or diluted with a suitable adjuvant, in this case also referred to as an excipient. Excipients may be solid, semisolid, or liquid materials which serve as a vehicle, carrier, or medium for the active substance. If necessary, further adjuvants are admixed in a manner known as such. Shaping steps, optionally in conjunction with mixing processes, may be carried out, such as granulation, compression, and the like.

The use according to the invention of the active substances according to the invention includes a process within the scope of treatment. The individual to be treated, preferably a mammal, in particular a human, or also a domestic animal or house pet, is administered an effective quantity of at least one 5-ring heteroaromatic of formula I, generally formulated according to pharmaceutical practice.

The invention further relates to the preparation of agents for treating an individual, preferably a mammal, in particular a human, domestic animal, or house pet.

The 5-ring heteroaromatic compounds of formula I or the corresponding pharmaceutical composition may be administered by oral, rectal, topical, parenteral, including subcutaneous, intravenous and intramuscular, and ocular, pulmonary, or nasal means. Oral administration is preferred.

Effective dosing of the active substance may depend on the type of 5-ring heteroaromatic, the mode of administration, the condition to be treated, and the severity of the condition to be treated. Such an effective dosing of the active substance may be easily determined by one skilled in the art in the field.

The dosage depends on the age, condition, and weight of the patient, as well as the mode of administration. As a rule, the daily dose of active substance is between approximately 0.5 and 100 mg/kg body weight for oral administration, and between approximately 0.1 and 10 mg/kg body weight for parenteral administration.

Preparation of the 5-Ring Heteroaromatic Compounds

The 5-ring heteroaromatic compounds according to the invention may be prepared analogously to methods known from the literature, which are familiar to one skilled in the art. The synthesis of pyrazoles in general is described in Synthetic Communications 2004, 34 (23), 4359; Heterocyclic Communications 2004, 10 (2-3), 163; Journal of Medicinal Chemistry 2004, 47 (24), 5872-5893; WO 2004037794; WO 2002004424; or said compounds may be prepared analogously to Example 4. Hydrazines are commercially available, or may be prepared according to methods known from the literature (for example, Houben-Weyl, Methoden der organischen Chemie [Methods of Organic Chemistry], Volumes X/2 and E16A, Stuttgart, 1967 and 1994; M. B. Smith, J. March, March's Advanced Organic Chemistry, New York, 2001).

Derivativization of the free amino group in III (for example, acylation or alkylation) may be carried out according to methods known from the literature, which are familiar to those skilled in the art (also see Diagram 1).

Diagram 1:

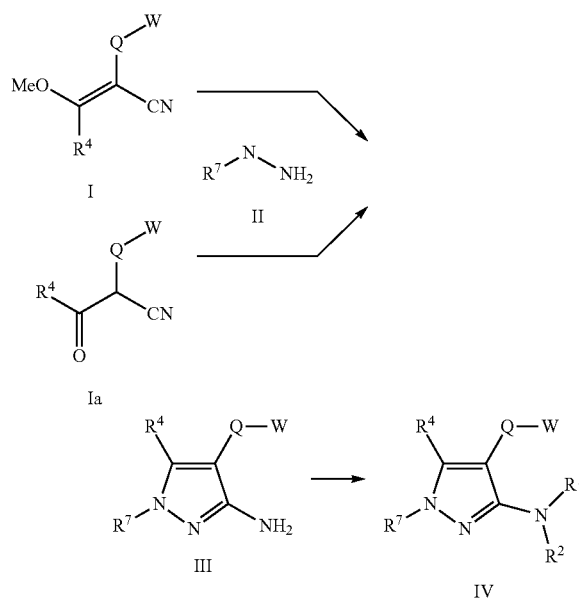

The synthesis of triazoles is described in Journal of the Chemical Society Abstracts, 1950, 612-614, and Journal of Medicinal Chemistry, 2002, 45(14), 2942-2952, or said compounds may be prepared analogously to Example 5. Hydrazides and thiohydrazides are commercially available, or may be prepared according to methods known from the literature (for example, Houben-Weyl, Methoden der organischen Chemie, Volumes VIII, X/2, and E5, Stuttgart, 1952, 1967, and 1985, and E5, Stuttgart, 1985; M. B. Smith, J. March, March's Advanced Organic Chemistry, New York, 2001). The aldehyde/ketones VI and amines XIV used in the synthesis path illustrated in Diagram 2 are likewise commercially available, or may be prepared according to known methods (for example, Houben-Weyl, Methoden der organischen Chemie, Volume XI/1, Stuttgart, 1957, and Houben-Weyl, Methoden der organischen Chemie, Volumes VII/1, VII2A, EIII, Stuttgart, 1954, 1973, 1983). In these cases as well, derivativization of the free amino group in VIII and XII (for example, acylation or alkylation) may be carried out according to methods known from the literature, which are familiar to those skilled in the art (Diagrams 2 and 2a).

Diagram 2:

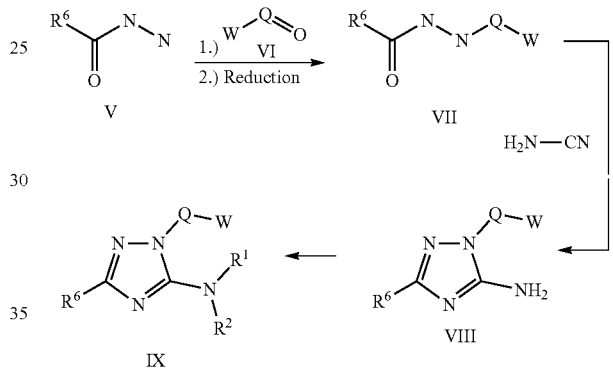

Diagram 2a:

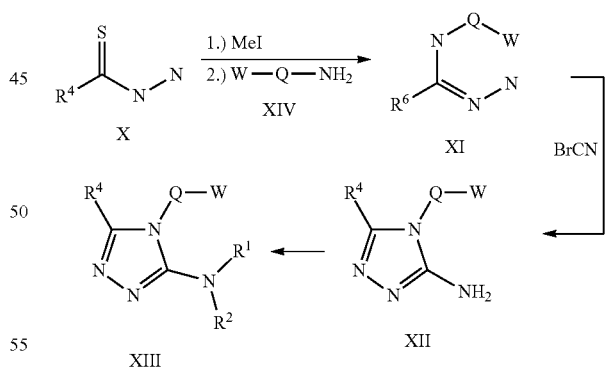

For the case that the 5-ring heteroaromatic compounds are imidazoles and the 5-intermediate products thereof, analogous syntheses are described in Journal of the Chemical Society—Abstracts, 1950, 2775-2784; Journal of Medicinal Chemistry 1993, 36 (22), 3337; Arzneimittelforschung 1977, 27 (10), 1889-1918; Tetrahedron 2004, 60 (18), 3987-3997; European Journal of Medicinal Chemistry 1992, 27 (7), 717-722; Arzneimittelforschung 1984, 34 (11A), 1612-1624, Journal of Organic Chemistry 1994, 59(24), 7299-7305; Tetrahedron 2002, 58 (49), 9865-9870; Journal of Organic Chemistry 1994, 59 (6), 1589-90; or said compounds may be prepared analogously to Examples 1 through 3 (Diagrams 3 and 3a). The synthesis of aminonitriles XXI is possible via the Strecker synthesis, for example, and is described, for example, in Houben-Weyl, Methoden der organischen Chemie, Volumes VIII and E5, Stuttgart, 1952 and 1985, and in Bioorganic & Medicinal Chemistry Letters 2004, 14 (21), 5317-5322, Tetrahedron 2004, 60 (46) 10559, or Synlett 2004, (4), 688-692.

Diagram 3:

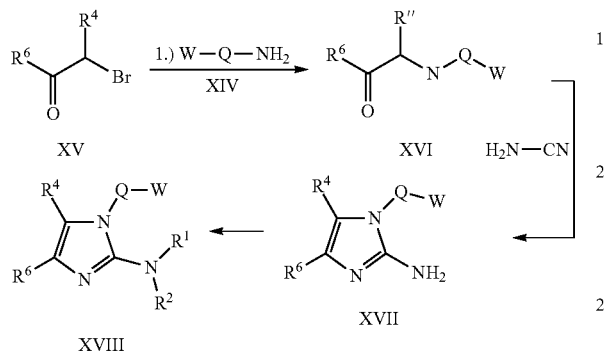

Diagram 3a:

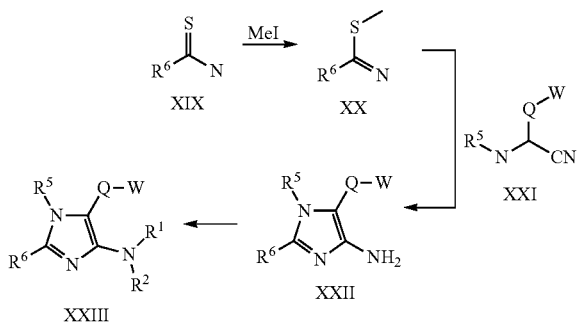

The α-haloketones and thioamides which are also needed are commercially available or may be prepared according to methods known from the literature (for example, Houben-Weyl, Methoden der organischen Chemie, 4th Edition, Volume VII/2c, Stuttgart, 1977, and Houben-Weyl, Methoden der organischen Chemie, Volume E5, Stuttgart, 1985).

Further methods for synthesizing the 5-ring heteroaromatic compounds are found in Houben-Weyl, Methoden der organischen Chemie, Volumes E8b and E8c, Stuttgart, 1994; M. B. Smith, J. March, March's Advanced Organic Chemistry, New York, 2001; and in the literature sources cited above for the use and preparation of imidazoles, triazoles, and pyrazoles.

The 5-ring heteroaromatic compounds according to the invention as well as any intermediate products may be obtained and, if necessary, purified by conventional means, for example by recrystallization from common organic solvents, preferably a short-chain alcohol such as ethanol, or by using chromatographic techniques.

Depending on the starting materials, the guanidine compounds of the formula according to the invention occur in the free form or as acid addition salts. The compounds in free form as well as the salts of said compounds resulting from the method may be converted to the desired acid addition salts or to the free form in a manner known as such.

The following examples illustrate the invention without limiting same. It is noted that the designation and formulaic representation of salts containing protonated nitrogen reflect only one of the many possibilities with regard to the charge distribution. This applies for tautomeric forms as well.

PRODUCTION EXAMPLES

Example 1

4-(4-Bromophenyl)-1-(2-methoxybenzyl)-1H-imidazole-2-ylamine 1.1
1-(4-Bromophenyl)-2-(2-methoxybenzylamino)ethanone A mixture of 500 mg (1.8 mmol) 2-bromo-1-(4-bromophenyl)ethanone and 520 mg (3.8 mmol) 2-methoxybenzylamine in 100 mL diethyl ether was stirred for 2 hr at room temperature. The resulting precipitate was then filtered, and the filtrate was combined with 1 M isopropanolic HCl and diluted with diethyl ether. The precipitate thus obtained was filtered and used in the subsequent step without further purification.

1.2. 4-(4-Bromophenyl)-1-(2-methoxybenzyl)-1H-imidazole-2-ylamine

A solution of the ketoamine (670 mg, 1.8 mmol crude product from 1.1) in 40 mL tetrahydrofuran/water (1:1) was adjusted to pH 4.5 with saturated $NaHCO_3$ solution, combined with 380 mg (9 mmol) cyanamide, and stirred for 2 hr under reflux. After the reaction was complete the batch was combined with ethyl acetate and extracted with 1 N NaOH and then with water. The organic phase was dried ($MgSO_4$) and concentrated, and the residue was separated on silica gel using methylene chloride/methanol 50:1, resulting in 100 mg of the target product in solid form.

ESI-MS [M+H$^+$]=358/360

$^1$H-NMR (400 MHz, CDCl$_3$), δ (ppm): 3.90 (s, 3H), 4.45 (d, 2H), 5.60 (s, 2H), 6.90 (m, 2H), 7.0-7.1 (m, 2H), 7.25-7.35 (m, 1H), 7.45 (d, 2H), 7.55 (d, 2H).

Example 2

1-(2-Methoxybenzyl)-4-(4-nitrophenyl)-1H-imidazole-2-ylamine 2.1
N[(4-(4-nitro-phenyl)-1H-imidazole-2-yl]acetamide A solution of 5.0 g (20.5 mmol) 2-bromo-1-(4-nitrophenyl)ethanone and 5.0 g (49.5 mmol) acetylguanidine in 70 mL acetonitrile was stirred for 4 hr at 40° C. and for an additional 72 hr at room temperature. The resulting precipitate was suctioned off in a mixture with methanol, refiltered, and dried. The solid (0.7 g) thus obtained was used without further purification.

ESI-MS [M+H$^+$]=265

2.2 4-(4-Nitrophenyl)-1H-imidazole-2-ylamine 2.7 g (11 mmol) N-[4-(4-nitrophenyl)-1H-imidazole-2-yl] acetamide was taken up in 30 mL EtOH, combined with 50 mL 50% hydrochloric acid, and stirred for 3 hr under reflux. The batch was made alkaline with 6 M NaOH and extracted with ethyl acetate. The organic phase was dried (MgSO$_4$) [and] concentrated. The residue (0.9 g) was further used without purification.

2.3 1-(2-Methoxybenzyl)-4-(4-nitrophenyl)-1H-imidazole-2-ylamine

A mixture of 4-(4-nitrophenyl)-1H-imidazole-2-ylamine (0.9 g, 4.4 mmol), 2-methoxybenzyl chloride (0.69 g, 4.4 mmol), and Cs$_2$CO$_3$ (1.6 g, 4.9 mmol) in dimethylformamide was stirred for 18 hr at room temperature. The batch was combined with 50% sodium chloride solution and extracted with ethyl acetate. The organic phase was washed several times with water and saturated sodium chloride solution and concentrated, and the residue was purified on silica gel using methylene chloride/methanol 50:1 (100 mg of a red solid).
ESI-MS [M+H$^+$]=325
$^1$H-NMR (400 MHz, CDCl$_3$), δ (ppm): 3.85 (s, 3H), 4.45 (d, 2H), 5.80 (s, 2H), 6.85-6.95 (m, 2H), 7.05 (d, 2H), 7.25-7.35 (m, 1H), 7.35 (s, 1H), 7.80 (d, 2H), 8.10 (d, 2H).

Example 3

5-(2-Methoxybenzyl)-2-phenyl-3H-imidazole-4-ylamine

3.1 2-(Benzhydtylideneamino)-3-(2-methoxyphenyl)propionitrile

A solution of 13.7 g (benzhydrylideneamino)acetonitrile (62 mmol) and 10.3 g 2-methoxybenzyl chloride (66 mmol) in 150 mL methylene chloride was combined with 75 mL 11 M NaOH, and after further addition of 1.4 g benzyltriethylammonium chloride (6.2 mmol) was stirred vigorously for 3 hr at room temperature. After the phases were separated, the organic phase was washed with water, dried over Na$_2$SO$_4$, filtered, and concentrated. The residue thus obtained (22.5 g) was used in the subsequent step without further purification.

3.2 2-Amino-3-(2-methoxyphenyl)propionitrile

A solution of 22.5 g 2-(benzhydrylideneamino)-3-(2-methoxyphenyl)propionitrile (66 mmol, crude product from 3.1) in 200 mL tetrahydrofuran was combined with 70 mL 1 M HCl and stirred for 3 hr at room temperature, and the reaction solution was then substantially concentrated on a rotary evaporator. After combination with methylene chloride the organic phase was extracted several times with 6 M HCl; the combined hydrochloric acid phases were made alkaline with 50% NaOH and extracted with methylene chloride, and the organic phase was then dried over Na$_2$SO$_4$ and concentrated. The oily residue (10.4 g) was used without further purification.

3.3 5-(2-Methoxybenzyl)-2-phenyl-3H-imidazole-4-ylamine

A solution of 1.7 g (10 mmol) 2-amino-3-(2-methoxyphenyl) propionitrile and 2.7 g (10 mmol) thiobenzimidic methyl ester hydroiodide in 30 mL dioxane was stirred for 2 hr under reflux. After separation from the resulting precipitate, the solution was concentrated and the residue was taken up in methylene chloride, washed with water, and the organic phase was dried (Na$_2$SO$_4$), filtered, and concentrated, and the residue of 1.4 g was mixed with acetic ethyl ester/heptane 19:1. The precipitate thus obtained was separated, the mother liquor was concentrated (430 mg), and separated by preparative HPLC (eluent: water/acetonitrile/acetic acid). 131 mg target product [was obtained], which was converted to the hydrochloride (92 mg) using 1 M etheric HCl solution.
ESI-MS [M+H$^+$]=280
$^1$H-NMR (400 MHz, d$_6$-DMSO), δ (ppm): 3.85 (s, 3H), 3.95 (s, 2H), 6.9 (t, 1H), 6.78 (s, 1H), 7.05 (t, 2H), 7.35 (t, 1H), 7.5 (m, 3H), 7.9 (d, 2H). 13.9 (s, br, 1H).

Example 4

4-(2-Methoxybenzyl)-1-phenyl-1H-pyrazole-3-ylamine

4.1 2-Methoxymethyl-3-(2-methoxyphenyl)actylonitrile

A mixture of 5.2 g 2-methoxybenzaldehyde (38 mmol) and 4.0 g acrylonitrile (5 mL, 76 mmol) was added drop-wise to a freshly prepared sodium methylate solution (1.3 g Na, 57 mmol in 100 mL methanol) over a period of 1 hr at 10° C., then stirred for 18 hr at room temperature. The batch was then diluted with water and extracted with acetic ethyl ester. Drying and concentration of the organic phase resulted in 10 g crude product, which was purified by chromatography on silica gel (eluent: methylene chloride/methanol 1:19) (4.4 g product as a mixture of at least three isomers).

4.2 4-(2-Methoxybenzyl)-1-phenyl-1H-pyrazole-3-ylamine

A solution of 0.6 mL sodium methylate (30% in methanol, 10.6 mmol) in 10 mL methanol was combined with 1 g (4.9 mmol) 2-methoxymethyl-3-(2-methoxyphenyl)acrylonitrile in 10 mL DMSO at room temperature and heated for 3.5 hr at 85° C., then combined with 0.57 g phenylhydrazine (4.9 mmol). The batch was then heated to 125° C. and the methanol was separated via a water separator. The batch was stirred for 1 additional hour at 115° C., then cooled to 5° C., combined with 50 mL water, and stirred for 1 hr. The resulting precipitate was suctioned off, washed with water, dried (0.6 g), and then mixed with 30 mL diethyl ether (0.35 g target product) ESI-MS [M+H$^+$]=280
$^1$H-NMR (400 MHz, d$_6$-DMSO), δ (ppm): 3.65 (s, 2H), 3.85 (s, 3H), 4.9 (s, 2H), 6.85 (t, 1H), 6.95 (d, 1H), 7.05 (t, 1H), 7.15-7.25 (m, 2H), 7.35 (t, 2H), 7.55 (d, 2H), 7.85 (s, 1H).

Example 5

2-(2-Methoxybenzyl)-5-phenyl-4H-[1,2,4]triazole-3-ylamine

5.1 Benzoic acid [1-(2-methoxyphenyl)methylidene]hydrazide

A suspension of 1.5 g (7.3 mmol) 2-methoxybenzaldehyde and 1 g (7.3 mmol) benzhydrazide in 35 mL n-hexane was stirred overnight at room temperature. The precipitate was suctioned off, dried, and used without further purification (1.75 g).

5.2 Benzoic acid N'-(2-methoxybenzyl)hydrazide 1.8 mL (11.4 mmol) triethylsilane was added to a solution of 1.45 g (5.7 mmol, crude product from 5.1) benzoic acid [1-(2-methoxyphenyl)methylidene]hydrazide in 10 mL trifluoroacetic acid at 0° C., then the mixture was stirred, first for 2 hr at 0° C. and then for 4 hr at room temperature. The yellow reaction solution was then combined with 120 mL 2 N HCl and extracted with methylene chloride, and the organic phase was then shaken with 1 N NaOH, dried with $Na_2SO_4$, and concentrated on a rotary evaporator. Stirring in diisopropyl ether and subsequent drying resulted in approximately 1.1 g product in the form of a white solid.

5.3 2-(2-Methoxybenzyl)-5-phenyl-4H-[1,2,4]triazole-3-ylamine

Benzoic acid N'-(2-methoxybenzyl)hydrazide (200 mg, 0.78 mmol from 5.2) was dissolved in a mixture of 1.5 mL dioxane and 1 mL water, combined with 164 mg (3.9 mmol) cyanamide dissolved in 1 mL water, adjusted to pH 2 with 1 N HCl, then stirred for 4 hr at 120° C. in a microwave oven at 200 watts power. The pH was checked every 30 minutes and readjusted to pH 2 as necessary. The resulting solid was then suctioned off, washed with a small quantity of diethyl ether, and dried (65 mg target product in the form of a light yellow solid).

ESI-MS $[M+H^+]$=281

$^1$H-NMR (400 MHz, $d_6$-DMSO), δ (ppm): 3.85 (s, 3H), 5.1 (s, 2H), 6.35 (s, 2H), 6.75 (d, 1H), 6.90 (t, 1H), 7.05 (d, 1H), 7.25-7.4 (m, 4H), 7.85 (d, 2H).

Production of End Products of Formula I

Compounds 6 and 7 were prepared by reacting suitable starting materials analogously to Example 4; compounds 8-40, 42-50, 52, 54, and 61 were prepared by reacting suitable starting materials analogously to Example 1 or 2; compound 41 was prepared by reacting suitable starting materials analogously to Anthony, Neville J.; Stokker, Gerald E.; Gomez, Robert P.; Solinsky, Kelly M.; Wai, John S.; Williams, Theresa M.; Young, Steven D.; Hutchinson, John H.; Halczenko, Wasyl; Biphenyl-substituted imidazoles useful as inhibitors of farnesyl-protein transferase, PCT Int. Appl. (1997), WO 9736875; compound 53 was prepared analogously to Example 51; compounds 56-60, 63-64 were prepared by reacting suitable starting materials analogously to Example 55; and compound 62 was prepared analogously to Example 3:

Example 6

4-(2-Methoxybenzyl)-1-(4-methoxyphenyl)-1H-pyrazole-3-ylamine

ESI-MS $[M+H^+]$=310

Example 7

1-(4-Fluorophenyl)-4-(2-methoxybenzyl)-1H-pyrazole-3-ylamine

ESI-MS $[M+H^+]$=298

Example 8

1-(2,6-Dimethoxybenzyl)-4-phenyl-1H-imidazole-2-ylamine hydrochloride

ESI-MS $[M+H^+]$=310

Example 9

N-[1-(2-Methoxybenzyl)-4-phenyl-1H-imidazole-2-yl]acetamide

ESI-MS $[M+H^+]$=322

Example 10

1-(2-Methoxybenzyl)-4-phenyl-1H-imidazole-2-ylamine hydrochloride

ESI-MS $[M+H^+]$=280

Example 11

4-tert-Butyl-1-(2-methoxybenzyl)-1H-imidazole-2-ylamine

ESI-MS $[M+H^+]$=260

Example 12

4-(4-Fluorophenyl)-1-(2-methoxybenzyl)-1H-imidazole-2-ylamine

ESI-MS $[M+H^+]$=298

Example 13

1-(2-Methoxybenzyl)-4-thiophene-2-yl-1H-imidazole-2-ylamine

ESI-MS $[M+H^+]$=286

Example 14

1-(2-Methoxybenzyl)-5-methyl-4-phenyl-1H-imidazole-2-ylamine

ESI-MS $[M+H^+]$=294

Example 15

4-Furan-2-yl-1-(2-methoxybenzyl)-1H-imidazole-2-ylamine hydrochloride

ESI-MS $[M+H^+]$=270

Example 16

1-(2-Methoxybenzyl)-4-naphthalene-2-yl-1H-imidazole-2-ylamine hydrochloride

ESI-MS $[M+H^+]$=330

Example 17

4-Benzo[b]thiophene-3-yl-1-(2-methoxybenzyl)-1H-imidazole-2-ylamine hydrochloride

ESI-MS $[M+H^+]$=336

Example 18

1-(2,6-Dimethoxybenzyl)-4-(4-fluorophenyl)-1H-imidazole-2-ylamine

ESI-MS [M+H$^+$]=328

Example 19

1-(2,6-Dimethoxybenzyl)-4-thiophene-2-yl-1H-imidazole-2-ylamine

ESI-MS [M+H$^+$]=316

Example 20

1-(2-Methoxybenzyl)-4-thiophene-3-yl-1H-imidazole-2-ylamine hydrochloride

ESI-MS [M+H$^+$]=286

Example 21

2-Amino-1-(2-methoxybenzyl)-1H-imidazole-4-carboxylic acid ethyl ester

ESI-MS=276

Example 22

1-(2-Methoxybenzyl)-4-(4-trifluoromethoxyphenyl)-1H-imidazole-2-ylamine ESI-MS

[M+H$^+$]=364

Example 23

1-(2-Methoxybenzyl)-4-(3-methoxyphenyl)-1H-imidazole-2-ylamine

ESI-MS [M+H$^+$]=310

Example 24

4-Adamantane-1-yl-1-(2-methoxybenzyl)-1H-imidazole-2-ylamine

ESI-MS [M+H$^+$]=338

Example 25

4-[2-Amino-1-(2,6-dimethoxybenzyl)-1H-imidazole-4-yl]benzonitrile hydrochloride

ESI-MS [M+H$^+$]=335

Example 26

1-(2,6-Dimethoxybenzyl)-4-(2-methoxyphenyl)-1H-imidazole-2-ylamine hydrochloride

ESI-MS [M+H$^+$]=340

Example 27

1-(2-Methoxybenzyl)-4-p-tolyl-1H-imidazole-2-ylamine

ESI-MS [M+H$^+$]=294

Example 28

1-(2-Chloro-6-methoxybenzyl)-4-thiophene-3-yl-1H-imidazole-2-ylamine

ESI-MS [M+H$^+$]=320/322

Example 29

1-(2-Chloro-6-methoxybenzyl)-4-(4-trifluoromethoxyphenyl)-1H-imidazole-2-ylamine

ESI-MS [M+H$^+$]=398/400

Example 30

5-[2-Amino-1-(2-methoxybenzyl)-1H-imidazole-4-yl]isoxazole-3-carboxylic acid ethyl ester

ESI-MS [M+H$^+$]=343

Example 31

1-(2-Fluoro-6-methoxybenzyl)-4-thiophene-3-yl-1H-imidazole-2-ylamine

ESI-MS [M+H$^+$]=304

Example 32

1-(2-Chloro-6-methoxybenzyl)-4-(4-methoxyphenyl)-1H-imidazole-2-ylamine

ESI-MS [M+H$^+$]=344

Example 33

4-[2-Amino-1-(2-fluoro-6-methoxybenzyl)-1H-imidazole-4-yl]benzonitrile

ESI-MS [M+H$^+$]=323

Example 34

1-(2-Chloro-6-methoxybenzyl)-4-(4-chlorophenyl)-1H-imidazole-2-ylamine

ESI-MS [M+H$^+$]=348/350/352

Example 35

4-(2,4-Dichlorophenyl)-1-(2-methoxybenzyl)-1H-imidazole-2-ylamine hydrochloride

ESI-MS [M+H$^+$]=348/350/352

Example 36

1-(2-Methoxybenzyl)-4-(5-methylfuran-2-yl)-1H-imidazole-2-ylamine

ESI-MS [M+H$^+$]=284

Example 37

1-(2-Chloro-6-methoxybenzyl)-4-thiophene-2-yl-1H-imidazole-2-ylamine

ESI-MS [M+H$^+$]=320

Example 38

1-(2-Methoxybenzyl)-4-(5-methylthiophene-2-yl)-1H-imidazole-2-ylamine

ESI-MS [M+H$^+$]=300

Example 39

4-(4-Isopropylphenyl)-1-(2-methoxybenzyl)-1H-imidazole-2-ylamine

ESI-MS [M+H$^+$]=322

Example 40

1-(2,6-Dimethoxybenzyl)-4-(3,4-dimethylphenyl)-1H-imidazole-2-ylamine hydrochloride

ESI-MS [M+H$^+$]=338

Example 41

5-Benzyl-1-(2-methoxybenzyl)-1H-imidazole-2-ylamine

ESI-MS [M+H$^+$]=294

Example 42

4-Benzofuran-2-yl-1-(2-methoxybenzyl)-1H-imidazole-2-ylamine

ESI-MS [M+H$^+$]=320

Example 43

1-(2-Methoxybenzyl)-4-naphthalene-1-yl-1H-imidazole-2-ylamine

ESI-MS [M+H$^+$]=330

Example 44

1-(2-Methoxybenzyl)-4-(4-phenoxyphenyl)-1H-imidazole-2-ylamine hydrochloride

ESI-MS [M+H$^+$]=372

Example 45

1-(2-Methoxybenzyl)-4-(3-nitrophenyl)-1H-imidazole-2-ylamine

ESI-MS [M+H$^+$]=325

Example 46

4-(4-Difluoromethoxyphenyl)-1-(2-methoxybenzyl)-1H-imidazole-2-ylamine ESI-MS

[M+H$^+$]=346

Example 47

1-(2-Methoxybenzyl)-4-(2-phenylthiazole-4-yl)-1H-imidazole-2-ylamine

ESI-MS [M+H$^+$]=363

Example 48

4-(4-Benzyloxyphenyl)-1-(2-methoxybenzyl)-1H-imidazole-2-ylamine

ESI-MS [M+H$^+$]=386

Example 49

1-(2-Methoxybenzyl)-4-thiazole-2-yl-1H-imidazole-2-ylamine hydrochloride

ESI-MS [M+H$^+$]=287

Example 50

5-[2-Amino-1-(2-methoxybenzyl)-1H-imidazole-4-yl]thiophene-2-carbonitrile

ESI-MS [M+H$^+$]=311

Example 51

4-(3-Aminophenyl)-1-(2-methoxybenzyl)-1H-imidazole-2-ylamine 51.1 A mixture of 2.5 g 1-(2-methoxybenzyl)-4-(3-nitrophenyl)-1H-imidazole-2-ylamine (7.7 mmol, Example 45), 2.5 g activated carbon, 30 mg iron(III) chloride (in the form of the hexahydrate) in 100 mL methanol, and 20 mL acetonitrile was heated at reflux, slowly combined with 50 mL hydrazine, and then stirred for an additional 2 hr under reflux. The batch was filtered, concentrated, taken up in acetic ethyl ester, extracted with water, and the organic phase was dried (Na$_2$SO$_4$) and concentrated. The residue thus obtained was mixed with acetic ethyl ester, suctioned off, and dried (2 g target product).

ESI-MS [M+H$^+$]=295

Example 52

1-(2,6-Dimethoxybenzyl)-4-(4-methylthiophene-2-yl)-1H-imidazole-2-ylamine

ESI-MS [M+H$^+$]=330

Example 53

4-(4-Aminophenyl)-1-(2-methoxybenzyl)-1H-imidazole-2-ylamine hydrochloride

ESI-MS [M+H$^+$]=295

Example 54

4-[2-Amino-1-(2-methoxy-4-nitrobenzyl)-1H-imidazole-4-yl]benzonitrile

ESI-MS [M+H$^+$]=350

Example 55

N-{3-[2-Amino-1-(2-methoxybenzyl)-1H-imidazole-4-yl]phenyl}-4-isopropylbenzenesulfonamide 55.1 A solution of 100 mg 4-(3-aminophenyl)-1-(2-methoxybenzyl)-1H-imidazole-2-ylamine (0.34 mmol, Example 51) in 3 mL pyridine was combined with 74 mg 4-isopropylbenzenesulfonic acid chloride at 0° C., then stirred for 18 hr at room temperature. The batch was then diluted with methylene chloride, extracted with 1 M NaOH and with water, and the organic phase was then dried (Na$_2$SO$_4$) and concentrated, and the residue thus obtained was stirred in acetic ethyl ester, suctioned off, and dried (130 mg target product).

ESI-MS [M+H$^+$]=477

Example 56

N-{3-[2-Amino-1-(2-methoxybenzyl)-1H-imidazole-4-yl]phenyl}benzenesulfonamide ESI-MS [M+H$^+$]=435

Example 57

N-{3-[2-Amino-1-(2-methoxybenzyl)-1H-imidazole-4-yl]phenyl}methanesulfonamide

ESI-MS [M+H$^+$]=373

Example 58

N-{3-[2-Amino-1-(2-methoxybenzyl)-1H-imidazole-4-yl]phenyl}benzamide ESI-MS [M+H$^+$]=399

Example 59

N-{4-[2-Amino-1-(2-methoxybenzyl)-1H-imidazole-4-yl]phenyl}benzenesulfonamide

ESI-MS [M+H$^+$]=435

Example 60

Thiophene-2-sulfonic acid {3-[2-amino-1-(2-methoxybenzyl)-1H-imidazole-4-yl]phenyl}amide

ESI-MS [M+H$^+$]=441

Example 61

1-(2-Methoxybenzyl)-4-pyridine-3-yl-1H-imidazole-2-ylamine

ESI-MS [M+H$^+$]=281

Example 62

5-(2-Methoxybenzyl)-2-(4-methoxyphenyl)-3H-imidazole-4-ylamine hydrochloride

ESI-MS [M+H$^+$]=310

Example 63

Biphenyl-4-sulfonic acid {3-[2-amino-1-(2-methoxybenzyl)-1H-imidazole-4-yl]phenyl}amide

ESI-MS [M+H$^+$]=511

Example 64

Propane-2-sulfonic acid {3-[2-amino-1-(2-methoxybenzyl)-1H-imidazole-4-yl]phenyl}amide

ESI-MS [M+H$^+$]=401

Biological Tests 1. h5-HT$_{5A}$-[$^3$H]5-CT Binding Assay

Membranes of HEK293 cells which permanently express the h5-HT$_{5A}$ receptor gene were incubated in 100 mM tris-HCl buffer (pH 7.7) containing 1 mM EDTA, in the presence of 2.5 nM [$^3$H]5-CT (total volume 600 μL). The total binding is defined as the binding that is observed when the membranes are incubated in the presence of only the radioligand. The inhibition induced by the compound is determined by incubation of cell membranes in the presence of the radioligand and various concentrations of the compound of interest. Nonspecific binding is defined as the [$^3$H]5-CT binding obtained by incubation of the membranes, the same as for the total binding, but in the presence of 10 μM methiothepine. Following incubation for 75 min at 30° C., the membrane suspension was filtered through a GF/B-Filter coated with 0.03% PEI, using a Skatron® harvesting system. The residual radioactivity in the filter was quantified by liquid scintillation counting.

2. Functional Assay for Human 5-HT5A Receptor Ligands, Serotonin-Induced Increase in GTP-Europium Binding General Description:

Stimulation of G protein-coupled receptors by means of suitable agonists results in binding of GTP to the α subunit of trimeric G proteins, followed by dissociation of the GTP-bound α subunit of the βγ subunits and the activation of signal transduction. By use of a europium-labeled GTP analog GTP-Eu, the activation of a G protein-coupled receptor by an agonist may be tracked as an increase in the binding of GTP-Eu to the receptor-G protein complex. After removal of unbound GTP-Eu, bound GTP-Eu may be quantified by measuring the time-resolved fluorescence emission in suitable detection devices.

Cell line: h5-HT5A__18.2_SH-sy-5y, a human neuroblastoma cell line which stably expresses the human 5-HT5A receptor.

Membrane preparation: Cell membranes were prepared according to a standard operating procedure in the presence of protease inhibitors, and were partially purified in two successive centrifugation steps at 40000×g. Aliquots were stored at −80° C.

Assay:

The assay was carried out in 96-well filter plates (AcroWell-96, Pall Corp.). The receptor membranes diluted in assay buffer (2.5 µM GDP, 100 mM NaCl, 3 mM $MgCl_2$, 50 mM HEPES at pH 7.4) were added to the filter plate (5 µg receptor membrane/well). Test compounds were dissolved in 100% DMSO, and series dilutions were added to the receptor membranes (DMSO end concentration 0.5%). The reaction was initiated by adding serotonin (end concentration 1 µM, total assay volume 100 µL). After an initial incubation period of 30 min at 30° C. the GTP-Eu (end concentration 10 nM) was added, followed by a second incubation period of 30 min at 30° C. The reaction was terminated by rapid vacuum filtration, and the wells were washed twice with chilled assay buffer. Bound GTP-Eu was measured in a VICTOR multi-label counter (PerkinElmer Corp.), using the time-resolved europium settings. The data were corrected for nonspecific binding, and IC50 values were calculated by means of PRISM4.0 (GraphPad Inc.), using standard nonlinear curve-fitting algorithms. Kb values were calculated from IC50 values, using the Cheng-Prusoff approximation.

Various concentrations of the test substances were used in both assays, and the Ki or IC50 values were determined. The affinities of selected compounds are presented in the following table:

TABLE 1

Affinity of selected compounds for 5-HT5A (Ki)

| Example # | Binding affinity 5-HT5A (Ki) |
|---|---|
| 1 | ++ |
| 2 | ++ |
| 3 | ++ |
| 4 | + |
| 5 | + |
| 6 | + |
| 7 | + |
| 8 | ++ |
| 9 | + |
| 10 | ++ |
| 11 | + |
| 12 | ++ |
| 13 | ++ |
| 14 | ++ |
| 15 | ++ |
| 16 | ++ |
| 17 | ++ |
| 18 | ++ |
| 19 | ++ |
| 20 | ++ |
| 21 | + |
| 22 | ++ |
| 23 | ++ |
| 24 | ++ |
| 25 | ++ |
| 26 | ++ |
| 27 | ++ |
| 28 | ++ |
| 29 | ++ |
| 30 | + |
| 31 | ++ |
| 32 | ++ |
| 33 | ++ |
| 34 | ++ |
| 35 | ++ |
| 36 | ++ |
| 37 | ++ |
| 38 | ++ |
| 39 | ++ |
| 40 | ++ |
| 41 | ++ |
| 42 | ++ |
| 43 | ++ |

TABLE 1-continued

Affinity of selected compounds for 5-HT5A (Ki)

| Example # | Binding affinity 5-HT5A (Ki) |
|---|---|
| 44 | ++ |
| 45 | ++ |
| 46 | ++ |
| 47 | ++ |
| 48 | ++ |
| 49 | ++ |
| 50 | ++ |
| 51 | ++ |
| 52 | ++ |
| 53 | ++ |
| 54 | + |
| 55 | ++ |
| 56 | ++ |
| 57 | ++ |
| 58 | ++ |
| 59 | ++ |
| 60 | ++ |
| 61 | ++ |
| 62 | + |
| 63 | ++ |
| 64 | ++ |

+ stands for an affinity >600 nM
++ stands for an affinity <600 nM

We claim:

1. A 5-ring heteroaromatic compound of general formula I

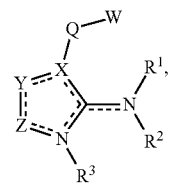

and/or corresponding enantiomeric, diastereomeric, and/or tautomeric forms thereof, and/or pharmaceutically acceptable salts thereof, wherein the stated radicals have the following definitions:

W: is a radical of general formula W1

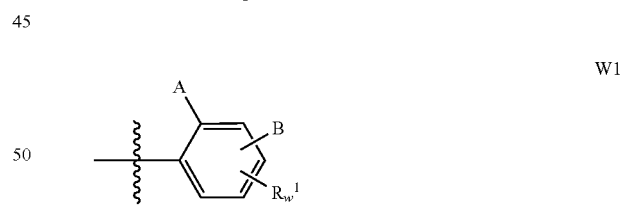

wherein

A: is $NO_2$, $NH_2$, CN, $CF_3$, $OCF_3$, $CHF_2$, $OCHF_2$, COOH, O—$CH_2$—COOH, halogen, SH, or in each case optionally substituted O—$C_1$-$C_6$ alkyl, S—$C_1$-$C_6$ alkyl, —O—CO—$C_1$-$C_6$ alkyl, —O—CO aryl, —O—CO hetaryl, —O—COO—$C_1$-$C_6$ alkyl, or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl, or $C_1$-$C_4$ alkylene-aryl, or in each case optionally substituted O—$R_A^1$, CO—$R_A^1$, S—$R_A^1$, SO—$R_A^1$, CO—O—$R_A^1$, $NR_A^4$—CO—O—$R_A^1$, O—$CH_2$—COO—$R_A^1$, $NR_A^2R_A^3$, $CONH_2$, $SO_2NH_2$, $NR_A^4$ CO—$R_A^1$, $SO_2$—$R_A^1$, $NR_A^4$—$S_2$—$R_A^1$, $SO_2$—$NR_A^2R_A^3$, or CO—$NR_A^2R_A^3$;

$R_A^1$: is in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_2$-$C_6$ alkenylene-aryl, or $C_1$-$C_6$ alkylene-hetaryl;

$R_A^2$: is hydrogen, or in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$-$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$R_A^3$: is in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

or the radicals $R_A^2$ and $R_A^3$ together with the nitrogen form a 3- to 7-membered saturated or aromatic heterocycle which is optionally substituted in each case, which may contain one, two, or three further heteroatoms, which may be different or the same, selected from the group consisting of O, N, and S, wherein two radicals substituted on this heterocycle together may optionally form a 3- to 7-membered anellated, saturated, unsaturated, or aromatic carbocycle or heterocycle, wherein the heterocycle may contain up to three heteroatoms selected from the group consisting of O, N, and S, which may be different or the same, and wherein the cyclic compound thus formed may optionally be substituted, or a further 3- to 7-membered, optionally substituted cyclic compound may be condensed thereon;

$R_A^4$: is hydrogen, or in each case optionally substituted $C_1$-$C_6$ alkyl, $C_2$-$C_6$ alkenyl, $C_2$-$C_6$ alkynyl, $C_3$-$C_7$ cycloalkyl, aryl, $C_1$-$C_4$ alkylene-aryl, $C_1$-$C_6$ alkylene-O—$C_1$-$C_6$ alkyl; or hetaryl;

B: is hydrogen, or is defined as for radical A, independently of radical A, or two of the radicals A, B, or $R_w^1$ in each case independently form, together with the attached C atoms, a 3- to 7-membered, saturated, unsaturated, or aromatic carbocycle which is optionally substituted in each case, or a 3- to 7-membered saturated, unsaturated, or aromatic heterocycle which in each case is optionally substituted and which may contain one, two, or three further heteroatoms, which may be different or the same, selected from the group comprising O, N, and S, wherein in each case two radicals substituted on this carbocycle or heterocycle together may optionally form a 3- to 7-membered anellated, saturated, unsaturated, or aromatic carbocycle or heterocycle, wherein the heterocycle may contain up to three heteroatoms selected from the group consisting of O, N, and S, which may be different or the same, and wherein the cyclic compound that is formed may optionally be substituted;

$R_w^1$: is hydrogen, OH, halogen, $NO_2$, $NH_2$, CN, $CF_3$, $CHF_2$, $CH_2F$, $OCF_3$, $OCHF_2$, $OCH_2F$, or in each case optionally substituted $C_1$-$C_6$ alkyl, $C_3$-$C_7$ cycloalkyl, $C_1$-$C_6$ alkylene-O—$C_1$-$C_6$ alkyl, $C_1$-$C_6$ thioalkyl, aryl, hetaryl, O—$C_1$-$C_6$ alkyl, O-benzyl, $C_1$-$C_6$ alkylamino, $C_1$-$C_6$ dialkylamino, pyrrolidinyl, piperidinyl, morpholinyl, CO—$C_1$-$C_6$ alkyl, $SO_2$—$C_1$-$C_6$ alkyl, CO-aryl, $SO_2$-aryl, CO—$C_1$-$C_4$ alkylene-aryl, $SO_2$—$C_1$-$C_4$ alkylene-aryl, SO-aryl, $CONH_2$, CONH—$C_1$-$C_6$ alkyl, $SO_2NH$—$C_1$-$C_6$ alkyl, CON—$(C_1$-$C_6$ alkyl$)_2$, $SO_2N$—$(C_1$-$C_6$ alkyl$)_2$, NH—SO—$C_1$-$C_6$ alkyl, or NH—CO—$C_1$-$C_6$ alkyl;

Q: is a radical of general formula Q1

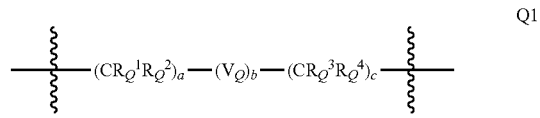

having the indices
a=0-4 (i.e., an integer equal to 0, 1, 2, 3, or 4)
b=0, 1 (i.e., an integer equal to 0 or 1)
c=0-4 (i.e., an integer equal to 0, 1, 2, 3, or 4)
wherein the sum of a, b, and c is at least 1, and 2, 3, 4, and no greater than 5, and
is equal to 0, 1, 2, 3, 4, or 5 for the case: X=N, Y=$CR^4$, Z=$CR^6$;

$R_Q^1$, $R_Q^2$, $R_Q^3$, $R_Q^4$ independently stand for:
hydrogen, halogen, OH, or
in each case optionally substituted $C_1$-$C_6$ alkyl, $C_2$-$C_6$ alkenyl, $C_2$-$C_6$ alkynyl, $C_1$-$C_6$ alkylene-$C_3$-$C_7$ cycloalkyl, $C_3$-$C_7$ cycloalkyl, aryl, $C_1$-$C_4$ alkylene-aryl, hetaryl, or $C_1$-$C_4$ alkylene-hetaryl, or
in each case two radicals $R_Q^1$ and $R_Q^2$ or $R_Q^3$ and $R_Q^4$ independently form together with the respective C atom a 3- to 7-membered, in each case optionally substituted, saturated or unsaturated carbocycle or heterocycle, wherein the heterocycle may contain one, two, or three heteroatoms selected from the group comprising O, N, and S;

$V_Q$: is in each case optionally substituted —CO—, —CO—$NR_Q^5$—, —$NR_Q^5$—CO—, —O—, —S—, —SO—, —$SO_2$—, —$SO_2$—$NR_Q^5$—, —$NR_Q^5$—$SO_2$—, —CS—, —CS—$NR_Q^5$—, —NR—CS—, —CS—O—, —O—CS—, —CO—O—, —O—CO—, —O—, ethynylene, —C(=$CR_Q^6R_Q^7$)—, —$CR_Q^6$=$CR_Q^7$—, —$NR_Q^5$—CO—$NR_Q^{5*}$, —O—CO—$NR_Q^5$—, or —$NR_Q^5$—;

$R_Q^5$, $R_Q^{5*}$ independently stand for:
hydrogen or
in each case optionally substituted $C_1$-$C_6$ alkyl, $C_1$-$C_6$ alkylene-O—$C_1$-$C_6$ alkyl, $C_2$-$C_6$ alkenyl, $C_3$-$C_{12}$ alkynyl, CO—$C_1$-$C_6$ alkyl, CO—O—$C_1$-$C_6$ alkyl, $SO_2$—$C_1$-$C_6$ alkyl, $C_3$-$C_7$ cycloalkyl, aryl, $C_1$-$C_4$ alkylene-aryl, CO—O—$C_1$-$C_4$ alkylene-aryl, CO—$C_1$-$C_4$ alkylene-aryl, CO-aryl, $SO_2$-aryl, hetaryl, CO-hetaryl, or $SO_2$—$C_1$-$C_4$ alkylene-aryl;

$R_Q^6$, $R_Q^7$ independently stand for:
Hydrogen, OH, or
in each case optionally substituted $C_1$-$C_6$ alkyl, $C_1$-$C_6$ alkoxy, $C_2$-$C_6$ alkenyl, $C_2$-$C_6$ alkynyl, $C_1$-$C_6$ alkylene-$C_3$-$C_7$ cycloalkyl, $C_3$-$C_7$ cycloalkyl, aryl, $C_1$-$C_4$ alkylene-aryl, hetaryl, or $C_1$-$C_4$ alkylene-hetaryl;

$R^1$, $R^2$ independently stand for:
  hydrogen, OH, CN, or
  in each case optionally substituted $C_1$-$C_6$ alkyl, O—$C_1$-$C_6$ alkyl, $C_1$-$C_6$ alkylene-O—$C_1$-$C_6$ alkyl, $C_3$-$C_7$ cycloalkyl, O—$C_3$-$C_7$ cycloalkyl, aryl, hetaryl, $C_1$-$C_4$ alkylene-aryl, $C_1$-$C_4$ alkylene-hetaryl, O-aryl, O—$C_1$-$C_4$ alkylene-aryl, O-hetaryl, O—$C_1$-$C_4$ alkylene-hetaryl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O-hetaryl, CO—O—$C_1$-$C_4$ alkylene-aryl, $SO_2$—$C_1$-$C_6$ alkyl, $SO_2$-aryl, $SO_2$-hetaryl, $SO_2$—$C_1$-$C_4$ alkylene-aryl, OCO—$C_1$-$C_6$ alkyl, OCO-aryl, OCO-hetaryl, OCO—$C_1$-$C_4$ alkylene-aryl, OCO—$C_1$-$C_4$ alkylene-hetaryl, $SO_2$—$C_1$-$C_6$ alkyl, $SO_2$-aryl, $SO_2$-hetaryl, or $SO_2$—$C_1$-$C_4$ alkylene-aryl, or
$R^1$ and $R^2$ together with the nitrogen form a 5- to 7-membered saturated or unsaturated heterocycle optionally substituted in each case, which may contain one, two, or three further heteroatoms, which may be different or the same, selected from the group consisting of O, N, and S, wherein in each case two radicals substituted on this carbocycle or heterocycle together may optionally form a 3- to 7-membered anellated, saturated, unsaturated, or aromatic carbocycle or heterocycle which is optionally substituted in each case, wherein the heterocycle may contain up to three heteroatoms, which may be different or the same, selected from the group comprising O, N, and S, and wherein the cyclic compound that is formed may optionally be substituted;
$R^3$ is a free electron pair or hydrogen;
X, Y, Z in each case have the following meanings:
  X=N, Y=$CR^4$, Z=$CR^6$, or
  X=C, Y=$NR^6$, Z=$CR^6$, or
  X=C, Y=$CR^4$, Z=$NR^7$, or
  X=N, Y=N, Z=$CR^6$, or
  X=N, Y=$CR^4$, Z=N;
$R^4$, $R^6$ in each case independently stand for a radical, selected from groups 1.), 3.), 4.) 5.), and 6.), which may be the same or different, and
$R^5$, $R^7$ in each case independently stand for a radical selected from groups 2.), 3.), 4.), and 5.), which may be the same or different;
1.) Hydrogen, $NO_2$, $NH_2$, CN, $CF_3$, $CHF_2$, $OCF_3$, $OCHF_2$, COOH, O—$CH_2$—COOH, halogen, or
  in each case optionally substituted $C_1$-$C_{10}$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, $C_1$-$C_6$ alkylene-O—$C_1$-$C_6$ alkyl, $C_1$-$C_6$ alkylene-O-aryl, COO—$C_1$-$C_6$ alkyl, or $C_1$-$C_4$ alkylene-COO—$C_1$-$C_6$ alkyl, or in each case optionally substituted O—$R_{Z,Y}^4$, S—$R_{Z,Y}^4$, $NR_{Z,Y}^6R_{Z,Y}^7$, CO—$OR_{Z,Y}^5$, CO—$R_{Z,Y}^5$, $NR_{Z,Y}^7$—CO—O—$R_{Z,Y}^5$, O—$CH_2$—COO—$R_{Z,Y}^5$, $NR_{Z,Y}^7$—CO—$R_{Z,Y}^5$, $SO_2$—$R_{Z,Y}^5$, SO—$R_{Z,Y}^5$, $NR_{Z,Y}^7$—$SO_2$—$R_{Z,Y}^5$, $SO_2NH_2$, $CONH_2$, $SO_2$—$NR_{Z,Y}^6R_{Z,Y}^7$, or CO—$NR_{Z,Y}^6R_{Z,Y}^7$;
2.) A free electron pair or hydrogen, $CH_2$—$CF_3$, $CH_2$—$CHF_2$, in each case optionally substituted $C_1$-$C_6$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, $C_1$-$C_6$ alkylene-O—$C_1$-$C_6$ alkyl, $C_1$-$C_6$ alkylene-O-aryl, COO—$C_1$-$C_6$ alkyl, or $C_1$-$C_4$ alkylene-COO—$C_1$-$C_6$ alkyl, or in each case optionally substituted CO—O—$R_{Z,Y}^5$, CO—$R_{Z,Y}^5$, $SO_2$—$R_{Z,Y}^5$, SO—$R_{Z,Y}^5$, $SO_2NH_2$, $CONH_2$, $SO_2$—$NR_{Z,Y}^6R_{Z,Y}^7$, or CO—$NR_{Z,Y}^6R_{Z,Y}^7$;
3.) Phenyl, 1-naphthyl, or 2-naphthyl, which in each case are or may be substituted with one, two, or three radicals selected from $R_{Z,Y}^1$, $R_{Z,Y}^2$ and $R_{Z,Y}^3$, wherein
$R_{Z,Y}^1$, $R_{Z,Y}^2$, and $R_{Z,Y}^3$ in each case independently represent a substituent from the following group:
  Hydrogen, $NO_2$, $NH_2$, OH, CN, $CF_3$, $CHF_2$, $OCF_3$, $OCHF_2$, COOH, O—$CH_2$—COOH, SH, halogen, or
  in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted
  O—$R_{Z,Y}^4$, S—$R_{Z,Y}^4$, $NR_{Z,Y}^6R_{Z,Y}^7$, CO—$OR_{Z,Y}^5$, $NR_{Z,Y}^7$—CO—O—$R_{Z,Y}^5$, O—$CH_2$—COO—$R_{Z,Y}^5$, $NR_{Z,Y}^7$—CO—$R_{Z,Y}^5$, $NR_{Z,Y}^7$—CO—$NR_{Z,Y}^5$, $SO_2$—$R_{Z,Y}^5$, $NR_{Z,Y}^7$—$SO_2$—$R_{Z,Y}^5$, $NR_{Z,Y}^7$—$SO_2$—$N_{Z,Y}^5$, $SO_2NH_2$, $CONH_2$, $SO_2$—$NR_{Z,Y}^6R_{Z,Y}^7$, or CO—$NR_{Z,Y}^6R_{Z,Y}^7$, or
  in each case two of the radicals selected from the group comprising $R_{Z,Y}^1$, $R_{Z,Y}^2$, and $R_{Z,Y}^3$ form, together with the ring atoms bearing these substituents, a 3- to 7-membered saturated or unsaturated carbocycle which in each case is optionally substituted, or a saturated or unsaturated 3- to 7-membered heterocycle which in each case is optionally substituted and which may contain one, two, or three further heteroatoms, which may be different or the same, selected from the group comprising O, N, and S, wherein optionally in each case two radicals substituted on this carbocycle or heterocycle together may form a 3- to 7-membered, anellated, saturated, unsaturated, or aromatic carbocycle or heterocycle, wherein the heterocycle may contain one, two, or three heteroatoms, which may be different or the same, comprising O, N, and S, and wherein the cyclic compound thus formed may optionally be substituted, and/or a further 3-to 7-membered, optionally substituted cyclic compound may be condensed thereon;
$R_{Z,Y}^4$ is in each case optionally substituted $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, heterocycloalkyl, $C_1$-$C_4$ alkylene-hetaryl, hetaryl, $C_1$-$C_4$ alkylene-aryl, aryl, or $C_1$-$C_6$ alkyl, which in each case is optionally substituted with a substituent selected from the group comprising halogen, $NO_2$, $NH_2$, OH, CN, $CF_3$, $CHF_2$, $OCF_3$, $OCHF_2$, optionally substituted NH—($C_1$-$C_6$ alkyl), and optionally substituted N($C_1$-$C_6$ alkyl)$_2$;
$R_{Z,Y}^5$ is in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, heterocycloalkyl, or $C_1$-$C_6$ alkylene-O—$C_1$-$C_6$ alkyl, dioxymethylenephenyl, benzofuranyl, dihydrobenzofuranyl, or indanyl, or aryl or hetaryl which in each case is optionally singly, doubly, or triply substituted with substituents independently selected from halogen, $NO_2$, $NH_2$, OH, CN, $CF_3$, $CHF_2$, $OCF_3$, $OCHF_2$, optionally substituted NH—($C_1$-$C_6$ alkyl), or optionally substituted N($C_1$-$C_6$ alkyl)$_2$, COOH, O—$CH_2$—COOH, or SH, or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl, or $C_1$-$C_4$ alkylene-aryl, or in each case optionally substituted O—$R_A^1$, CO—$R_A^1$, S—$R_A^1$, SO—$R_A^1$, CO—O—$R_A^1$, $NR_A^4$—CO—O—$R_A^1$, O—$CH_2$—COO—$R_A^1$, $NR_A^2R_A^3$, $CONH_2$, $SO_2NH_2$, $NR_A^4$—CO—$R_A^1$, $SO_2$—$R_A^1$, $NR_A^4$—$SO_2$—$R_A^1$, $SO_2$—$NR_A^2R_A^3$, or CO—$NR_A^2R_A^3$, $R_{Z,Y}^6$ is hydrogen, or
in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, $C_1$-$C_4$ alkylene-aryl, $C_1$-$C_4$ alkylene-hetaryl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, CO—O—$C_1$-$C_4$ alkylene-aryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$R_{Z,Y}^7$ is hydrogen or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

or the radicals $R_{Z,Y}^6$ and $R_{Z,Y}^7$ together with the nitrogen form a 3- to 7-membered saturated or aromatic heterocycle which is optionally substituted in each case and which may contain one, two, or three further heteroatoms, which may be different or the same, selected from the group comprising O, N, and S; and in each case two radicals substituted on this heterocycle together may optionally form a 3- to 7-membered anellated, saturated, unsaturated, or aromatic carbocycle or heterocycle, wherein the heterocycle may contain one, two, or three heteroatoms, which may be different or the same, selected from the group comprising O, N, and S, and the cyclic compound thus formed may optionally be substituted, or a further 3- to 7-membered, optionally substituted cyclic compound may be condensed thereon;

4.) A 5- or 6-membered, in each case optionally substituted, aromatic heterocycle which may contain one, two, or three heteroatoms which may be different or the same, selected from the group comprising O, N, and S, and which in each case may be substituted with $R_{Z,Y}^1$, $R_{Z,Y}^2$, and $R_{Z,Y}^3$, where $R_{2x}^1$, $R_{Z,Y}^2$, and $R_{Z,Y}^3$ independently have the meanings given above under 3.);

5.) A $C_5$-$C_{18}$ bi- or tricyclic saturated hydrocarbon radical which in each case is optionally substituted;

6.) $R^4$ and $R^6$ together with X and Y form, optionally substituted in each case, a $C_6$-$C_{10}$-membered saturated, unsaturated, or aromatic carbocycle, which may be substituted in each case with one, two, or three radicals which in each case are independently selected from $R_{Z,Y}^8$;

$R_{Z,Y}^8$: is hydrogen, $NO_2$, $NH_2$, OH, CN, $CF_3$, $CHF_2$, $OCF_3$, $OCHF_2$, COOH, O—$CH_2$—COOH, SH, halogen, or in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted O—$R_{Z,Y}^4$, S—$R_{Z,Y}^4$, $NR_{Z,Y}^6R_{Z,Y}^7$, CO—$OR_{Z,Y}^5$, $NR_{Z,Y}^7$—CO—O—$R_{Z,Y}^5$, O—$CH_2$—COO—$R_{Z,Y}^5$, $NR_{Z,Y}^7$—CO—$R_{Z,Y}^5$, $SO_2$—$R_{Z,Y}^5$, $NR_{Z,Y}^7$—$SO_2$—$R_{Z,Y}^5$, $SO_2NH_2$, $CONH_2$, $SO_2$—$NR_{Z,Y}^6R_{Z,Y}^7$, or CO—$NR_{Z,Y}^8R_{Z,Y}^7$.

2. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, A, $R_A^1$, $R_A^2$, $R_A^3$, $R_A^4$, B, $Rw^1$, Q, a, b, c, $R_Q^1$, $R_Q^2$, $R_Q^3$, $R_Q^4$, $V_Q$, $R_Q^5$, $R_Q^{5*}$, $R_Q^6$, $R_Q^6$, $R_Q^7$, $R_1$, $R_2$, $R_3$, X, Y, and Z, unless stated otherwise below, have the same meaning as in claim 1, and the radicals below have the following definitions:

$R^4$, $R^6$ in each case independently stand for a radical selected from groups 1.), 3.), 4.), and 5.), which may be the same or different, and $R^5$, $R^7$ in each case independently stand for a radical selected from groups 2.), 3.), 4.), and 5.), which may be the same or different, wherein groups 1.)-5.) in each case have the meanings stated in claim 1.

3. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, A, $R_A^1$, $R_A^2$, $R_A^3$, $R_A^4$, B, $R_w^1$, $R_1$, $R_2$, $R_3$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, and $R_{Z,Y}^8$, unless stated otherwise below, have the same meaning stated in claim 1, and the radicals below have the following definitions:

Q: in formula Q1 is the sum of a, b, and c and is equal to 1, 2, or 3;

$R_Q^1$, $R_Q^2$, $R_Q^3$, $R_Q^4$ independently stand for:
hydrogen, halogen, OH, or optionally substituted $C_1$-$C_6$ alkyl;

$V_Q$: is —CO—, —CO—$NR_Q^5$—, —$NR_Q^5$—CO—, —O—, or —S—;

$R_Q^5$: is hydrogen, $CH_3$.

4. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, A, $R_A^1$, $R_A^2$, $R_A^3$, $R_A^4$, B, $R_w^1$, $R_1$, $R_2$, $R_3$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, and $R_{Z,Y}^8$, unless stated otherwise below, have the same meaning stated in claim 1, and the radicals below have the following definitions:

Q: in formula Q1 is the sum of a=1 and b=c=0;

$R_Q^1$, $R_Q^2$ independently stand for:
hydrogen, halogen, OH, or optionally substituted $C_1$-$C_6$ alkyl.

5. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals Q, $R_Q^1$, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, and $R_{Z,Y}^8$, unless stated otherwise below, have the same meaning stated in claim 1, and the radicals below have the following definitions:

wherein the radicals A, B and $R_w^1$ independently, and in each case independently of their respective occurrence, may have one of the meanings stated below:

A: is halogen, $NH_2$, CN, $CF_3$, $OCF_3$, $OCHF_2$, COOH, O—$CH_2$—COOH, SH, O—$C_1$-$C_6$ alkyl, S—$C_1$-$C_6$ alkyl, $C_1$-$C_6$ alkyl, or in each case optionally substituted O—$R_A^1$, CO—$R_A^1$, S—$R_A^1$, O—$CH_2$—COO—$R_A^1$, $NR_A^2R_A^3$, $CONH_2$, $SO_2NH_2$, $SO_2$—$R_A$', $NR_A^4$—$SO_2$—$R_A^1$, $SO_2$—$NR_A^2R_A^3$, or CO—$NR_A^2R_A^3$;

$R_A^1$: is in each case optionally substituted $C_1$-$C_6$ alkyl, $C_3$-$C_7$ cycloalkyl, phenyl, or benzyl;

$R_A^2$; $R_A^3$ independently stand for
hydrogen, or
in each case optionally substituted $C_1$-$C_6$ alkyl, phenyl, benzyl, phenethyl, CO—$C_1$-$C_6$ alkyl, CO-aryl, CO—O—$C_1$-$C_6$ alkyl, $SO_2$—$C_1$-$C_6$ alkyl, $SO_2$-aryl, $SO_2$-hetaryl, or $SO_2$—$C_1$-$C_4$ alkylene-aryl; or both radicals $R_A^2$ and $R_A^3$ together with the nitrogen form a 5- or 6-membered saturated or aromatic ring which is optionally substituted in each case, and which may contain one or two heteroatoms, which may be the same or different, selected from the group comprising O and N;

$R_A^4$: is hydrogen or an optionally substituted $C_1$-$C_6$ alkyl radical;

B: is hydrogen, halogen, CN, $CF_3$, —$CHF_2$, $OCF_3$, $OCHF_2$, or in each case optionally substituted $C_1$-$C_6$ alkyl or $C_2$-$C_6$ alkenyl, or in each case optionally substituted —O—$CH_2$—COO—$R_A^1$, —O—$R_A^1$, S—$R_A^1$, $NRA^2RA^3$, —$NR_A^4$—CO—$R_A^1$, or CO—$NRA^2RA^3$; $NRA^4$ $SO_2$—$RA^1$; or B together with $R_w^1$ forms one of the radicals —$(CH_2)_3$—, —O—$CH_2$—O—, —O—$(CH_2)_2$—O—, —CH=CH—CH=CH—, —O—$(CH_2)_2$—, or —$(CH_2)_2$—O—;

$R_w^1$: is hydrogen, F, Cl, CN, $CF_3$, O—$CF_3$, or in each case optionally substituted $C_1$-$C_6$ alkyl, aryl, $C_1$-$C_6$ alkylamino, or $C_1$-$C_6$ dialkylamino.

6. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, A, $R_A^1$, $R_A^2$, $R_A^3$, $R_A^4$, B, $R_w^1$, Q, a, b, c, $R_Q^1$, $R_Q^2$, $R_Q^3$, $R_Q^4$, $V_Q$, $R_Q^5$, $R_Q^5{*}$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, and $R_{Z,Y}^8$, unless stated otherwise below, have the same meaning stated in claim 1, and the radicals below have the following definitions:

$R^1$, $R^2$ independently stand for:
hydrogen, OH, CN, $C_1$-$C_6$ alkyl, $C_1$-$C_6$ alkylene-O—$C_1$-$C_6$ alkyl, substituted aryl, benzyl, CO—$C_1$-$C_6$ alkyl, CO-aryl, or CO—$C_1$-$C_4$ alkylene-aryl;

$R^3$ is a free electron pair or hydrogen.

7. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, A, $R_A^1$, $R_A^2$, $R_A^3$, $R_A^4$, B, $R_w^1$, Q, a, b, c, $R_Q^1$, $R_Q^2$, $R_Q^3$, $R_Q^4$, $V_Q$, $R_Q^5$, $R_Q^5{*}$, $R_Q^6$, $R_Q^7$, $R_1$, $R_2$, $R_3$, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, and $R_{Z,Y}^8$, unless stated otherwise below, have the same meaning stated in claim 1, and the radicals below have the following definitions:

X, Y, Z X=N, Y=$CR^4$, Z=$CR^6$, or
X=C, Y=$CR^4$, Z=$NR^7$, or
X=N, Y=N, $CR^6$.

8. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, A, $R_A^1$, $R_A^2$, $R_A^3$, $R_A^4$, B, Q, a, b, c, $R_Q^1$, $R_Q^2$, $R_Q^3$, $R_Q^4$, $R_Q^5$, $R_Q^5{*}$, $R_Q^6$, $R_Q^7$, $R_1$, $R_2$, $R_3$, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, and $R_{Z,Y}^8$, unless stated otherwise below, have the same meaning stated in claim 1, and the radicals below have the following definitions:

X, Y, Z X=N, Y=$CR^4$, Z=$CR^6$, or
X=N, Y=N, Z=$CR^6$.

9. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, A, $R_A^1$, $R_A^2$, $R_A^3$, $R_A^4$, B, $R_w^1$, Q, a, b, c, $R_Q^1$, $R_Q^2$, $R_Q^3$, $R_Q^4$, $R_Q^5$, $R_Q^5{*}$, $R_Q^6$, $R_Q^7$, $R_1$, $R_2$, $R_3$, X, Y, and Z, unless stated otherwise below, have the same meaning stated in claim 1, and the radicals below have the following definitions:

$R^4$, $R^6$ in each case independently stand for a radical, selected from groups 1.), 3.), 4.), and 5.), which may be the same or different, and $R^5$, $R^7$ in each case independently stand for a radical selected from groups 2.), 3.), 4.), and 5.), which may be the same or different, wherein groups 1.), 2.), 3.), 4.), and 5.) are defined as follows:

1.) Hydrogen, CN, $CF_3$, $CHF_2$, O—$CH_2$—COOH, halogen, or
in each case optionally substituted $C_1$-$C_{10}$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, or in each case optionally substituted
O—$R_{Z,Y}^4$, $NR_{Z,Y}^6R_{Z,Y}^7$, CO—$OR_{Z,Y}^5$, $NR_{Z,Y}^7$—CO—O—$R_{Z,Y}^5$, O—$CH_2$—COO—$R_{Z,Y}^5$, $NR_{Z,Y}^7$—CO—$R_{Z,Y}^6$, $SO_2$—$R_{Z,Y}^5$, $NR_{Z,Y}^7$—$SO_2$—$R_{Z,Y}^5$, $SO_2NH_2$, $CONH_2$, $SO_2$—$NR_{Z,Y}^6R_{Z,Y}^7$, or CO—$NR_{Z,Y}^6R_{Z,Y}^7$;

2.) A free electron pair or hydrogen,
in each case optionally substituted $C_1$-$C_{10}$ alkyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, COO—$C_1$-$C_6$ alkyl, or in each case optionally substituted SO—$R_{Z,Y}^5$, $SO_2NH_2$, $CONH_2$, $SO_2$-$NR_{Z,Y}^6R_{Z,Y}^7$ or CO—$NR_{Z,Y}^6R_{Z,Y}^7$;

3.) Phenyl, 1-naphthyl, or 2-naphthyl, in each case substituted with $R_{Z,Y}^1$, $R_{Z,Y}^2$, and $R_{Z,Y}^3$, wherein
$R_{Z,Y}^1$, $R_{Z,Y}^2$, and $R_{Z,Y}^3$ in each case independently represent a substituent from the following group:
Hydrogen, $NH_2$, CN, $CF_3$, $CHF_2$, $OCF_3$, $OCHF_2$, O—$CH_2$—COON, halogen, or
in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted
O—$R_{Z,Y}^4$, S—$R_{Z,Y}^4$, $NR_{Z,Y}^6R_{Z,Y}^7$, $NR_{Z,Y}^7$—CO—O—$R_{Z,Y}^5$, $NR_{Z,Y}^7$—CO—$R_{Z,Y}^5$, $SO_2$—$R_{Z,Y}^5$, $N_{Z,Y}^7$—$SO_2$—$R_{Z,Y}^5$, $SO_2NH_2$, $CONH_2$, $SO_2$—$NR_{Z,Y}^6R_{Z,Y}^7$, or CO—$NR_{Z,Y}^6R_{Z,Y}^7$, or in each case two of the radicals selected from $R_{Z,Y}^1$, $R_{Z,Y}^2$, and $R_{Z,Y}^3$ form, together with the ring atoms bearing these substituents, a 3- to 7-membered saturated or unsaturated carbocycle which in each case is optionally substituted, or a saturated or unsaturated heterocycle which in each case is optionally substituted and which may contain one, two, or three further heteroatoms, which may be the same or different, selected from the group comprising O, N, and S;

$R_{Z,Y}^4$ is in each case optionally substituted $C_1$-$C_4$ alkylene-$C_3$-$C_7$ cycloalkyl, $C_1$-$C_4$ alkylene-heterocycloalkyl, heterocycloalkyl, hetaryl, aryl, $C_1$-$C_4$ alkylene-hetaryl, hetaryl, $C_1$-$C_4$ alkylene-aryl, or $C_1$-$C_6$ alkyl, which in each case is optionally substituted with a substituent selected from the group comprising halogen, $NO_2$, $NH_2$, OH, CN, $CF_3$, $CHF_2$, $OCF_3$, $OCHF_2$, $NH-(C_1-C_6$ alkyl), and $N(C_1-C_6$ alkyl$)_2$;

$R_{Z,Y}^5$ is in each case optionally substituted $C_1-C_6$ alkyl, $C_2-C_6$ alkenyl, $C_2-C_6$ alkynyl, $C_3-C_7$ cycloalkyl, $C_1-C_4$ alkylene-$C_3-C_7$ cycloalkyl, $C_1-C_4$ alkylene-heterocycloalkyl, heterocycloalkyl, or $C_1-C_6$ alkylene-O—$C_1-C_6$ alkyl, or dioxymethylenephenyl, or aryl or hetaryl which in each case is optionally singly, doubly, or triply substituted with substituents independently selected from the group comprising halogen, $NO_2$, $NH_2$, OH, CN, $CF_3$, $CHF_2$, $OCF_3$, $OCHF_2$, $NH-(C_1-C_6$ alkyl), or $N(C_1-C_6$ alkyl$)_2$, COOH, O—$CH_2$—COOH, SH, or in each case optionally substituted $C_1-C_6$ alkyl, $C_3-C_7$ cycloalkyl, aryl, hetaryl, heterocycloalkyl, or in each case optionally substituted O—$R_A^1$, S—$R_A^1$, $NR_A^4$—CO—O—$R_A^1$, O—$CH_2$—COO—$R_A^1$, $NR_A^2 R_A^3$, $CONH_2$, $SO_2NH_2$, $SO_2$—$R_A^1$, $NR_A^4$—$SO_2$—$R_A^1$, or $SO_2$—$NR_A^2 R_A^3$;

$R_{Z,Y}^6$ is hydrogen, or
  in each case optionally substituted $C_1-C_6$ alkyl, $C_3-C_7$ cycloalkyl, $C_1-C_4$ alkylene-$C_3-C_7$ cycloalkyl, $C_1-C_4$ alkylene-heterocycloalkyl, aryl, hetaryl, heterocycloalkyl, $C_1-C_6$ alkylene-O—$C_1-C_6$ alkyl, CO—$C_1-C_6$ alkyl, $C_1-C_4$ alkylene-aryl, $C_1-C_4$ alkylene-hetaryl, CO-aryl, CO-hetaryl, CO—$C_1-C_4$ alkylene-aryl, CO—$C_1-C_6$ alkylene-hetaryl, CO—O—$C_1-C_6$ alkyl, CO—O-aryl, CO—O—$C_1-C_4$ alkylene-aryl, CO—O-hetaryl, CO—O—$C_1-C_4$ alkylene-hetaryl, CO—O—$C_1-C_4$ alkylene-aryl, $SO_2$—$C_1-C_6$ alkyl, $SO_2$-aryl, $SO_2$-hetaryl, $SO_2$—$C_1-C_4$ alkylene-aryl, or $SO_2$—$C_1-C_4$ alkylene-hetaryl;

$R_{Z,Y}^7$ is hydrogen or in each case optionally substituted $C_1-C_6$ alkyl,
  or the radicals $R_{Z,Y}^6$ and $R_{Z,Y}^7$ together with the nitrogen form a 3- to 7-membered saturated or aromatic heterocycle which is optionally substituted in each case, which may contain one, two, or three further heteroatoms, which may be different or the same, selected from the group comprising O, N, and S;

4.) A 5- or 6-membered aromatic heterocycle which may contain one, two, or three heteroatoms selected from the group
  comprising O, N, and S, and which in each case may be substituted with a substituent selected from the group consisting of $R_{Z,Y}^1$, $R_{Z,Y}^2$, and $R_{Z,Y}^3$;

5.) A $C_5-C_{10}$ bi- or tricyclic saturated hydrocarbon radical which is optionally substituted.

10. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals Q, a, b, c, $R_Q^1$, $R_Q^2$, $R_Q^3$, $R_Q^4$, $R_Q^5$, $R_Q^{5*}$, $R_Q^6$, $R_Q^7$, $R_1$, $R_2$, $R_3$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, and $R_{Z,Y}^8$, unless stated otherwise below, have the same meaning stated in claim 1, and the radicals below have the following definitions:
  A: is F, Cl, $OCF_3$, or $OCHF_2$, or in each case optionally substituted $C_1-C_6$ alkyl, O—$C_1-C_6$ alkyl, S—$C_1-C_6$ alkyl, or $OR_A^1$;
  B: is hydrogen, F, Cl, $CF_3$, $OCF_3$, or $OCHF_2$, or in each case optionally substituted $C_1-C_6$ alkyl, O—$C_1-C_6$ alkyl, or S—$C_1-C_6$ alkyl;
  $R_w^1$: is hydrogen, F, Cl, CN, $CF_3$, or O—$CF_3$;
  $R_A^1$: is $C_1-C_6$ alkyl or phenyl optionally substituted in each case.

11. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, A, $R_A^1$, $R_A^2$, $R_A^3$, $R_A^4$, B, $R_w^1$, $R_1$, $R_2$, $R_3$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, and $R_{Z,Y}^8$, unless stated otherwise below, have the same meaning stated in claim 1, and the radicals below have the following definitions:
  Q: is —$CR_Q^1 R_Q^2$—;
  $R_Q^1$, $R_Q^2$ in each case independently stand for hydrogen, F, or $CH_3$.

12. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, A, $R_A^1$, $R_A^2$, $R_A^3$, $R_A^4$B, $R_w^1$, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, and $R_{Z,Y}^8$, unless stated otherwise below, have the same meaning stated in claim 1, and the radicals below have the following definitions:
  $R^1$, $R^2$ independently stand for:
    hydrogen, OH, CN, O-methyl, O-phenyl, acetyl, benzoyl, O-acetyl, or O-benzoyl;
  $R^3$ is a free electron pair or hydrogen.

13. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, A, $R_A^1$, $R_A^2$, $R_A^3$, $R_A^4$, B, $R_w^1$, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, X, Y, Z, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, and $R_{Z,Y}^8$, unless stated otherwise below, have the same meaning stated in claim 1, and the radicals below have the following definitions:
  $R^1$, $R^2$ are hydrogen;
  $R^3$ is a free electron pair or hydrogen.

14. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, A, $R_A^1$, $R_A^2$, $R_A^3$, $R_A^4$, B, $R_w^1$, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, $R_4$, $R_5$, $R_6$, $R_7$, $R_{Z,Y}^1$, $R_{Z,Y}^2$, $R_{Z,Y}^3$, $R_{Z,Y}^4$, $R_{Z,Y}^5$, $R_{Z,Y}^6$, $R_{Z,Y}^7$, and $R_{Z,Y}^8$, unless stated otherwise below, have the same meaning stated in claim 1, and the radicals below have the following definitions:
  X=N, Y=$CR^4$, Z=$CR^6$.

15. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, A, $R_A^1$, $R_A^2$, $R_A^3$, $R_A^4$, B, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, X, Y, and Z, unless stated otherwise below, have the same meaning stated in claim 1, and the radicals below have the following definitions:
  $R^4$, $R^6$ in each case independently stand for a radical, selected from groups 1.), 3.), 4.) and 5.), which may be the same or different, and
  $R^5$, $R^7$ is a radical selected from groups 2.) and 3.), which may be the same or different, wherein groups 1.), 2.), 3.), 4.), and 5.) are defined as follows:
  1.) Hydrogen, $CF_3$, $CHF_2$, or
    in each case optionally substituted $C_1-C_{10}$ alkyl, $C_3-C_7$ cycloalkyl, $C_1-C_6$ alkylene-$C_3-C_7$ cycloalkyl, $C_1-C_4$ alkylene-aryl, $C_1-C_4$ alkylene-hetaryl, or in each case optionally substituted
    $NR_{Z,Y}^7$—CO—O—$R_{Z,Y}^5$, $SO_2$—$R_{Z,Y}^5$, $NR_{Z,Y}^7$—$SO_2$—$R_{Z,Y}^5$, $CONH_2$, $SO_2$—$NR_{Z,Y}^6 R_{Z,Y}^7$ or CO—$NR_{Z,Y}^6 R_{Z,Y}^7$;

2.) A free electron pair or hydrogen, or
in each case optionally substituted $C_1$-$C_{10}$ alkyl, or $C_3$-$C_7$ cycloalkyl;
3.) Phenyl or naphthyl, in each case substituted with $R_{Z,Y}^1$, $R_{Z,Y}^2$, and $R_{Z,Y}^3$, wherein $R_{Z,Y}^1$, $R_{Z,Y}^2$, and $R_{Z,Y}^3$ in each case independently represent a substituent from the following group:
Hydrogen, CN, $NH_2$, $CF_3$, $CHF_2$, $OCF_3$, $OCHF_2$, $O-CH_2-COOH$, halogen, or
in each case optionally substituted aryl, hetaryl, heterocycloalkyl, $C_1$-$C_6$ alkyl, $C_3$-$C_7$ cycloalkyl, or in each case optionally substituted
$O-R_{Z,Y}^4$, $NR_{Z,Y}^6 R_{Z,Y}^7$, $SO_2-NR_{Z,Y}^6 R_{Z,Y}^7$, or $N_{Z,Y}^7 SO_2-R_{Z,Y}^5$, or in each case two of the radicals from $R_{Z,Y}^1$, $R_{Z,Y}^2$, or $R_{Z,Y}^3$ form, together with the ring atoms bearing these substituents, a 3- to 7-membered saturated or unsaturated carbocycle which in each case is optionally substituted, or a saturated or unsaturated heterocycle which in each case is optionally substituted and which may contain one, two, or three further heteroatoms selected from the group comprising O, N, and S; wherein
$R_{Z,Y}^4$ in each case is an optionally substituted hetaryl, aryl, or
$C_1$-$C_6$ alkyl, which in each case is optionally substituted with a substituent selected from the group comprising halogen, CN, $CF_3$, $CHF_2$, $OCF_3$, $OCHF_2$, optionally substituted $NH-(C_1$-$C_6$ alkyl), and optionally substituted $N(C_1$-$C_6$ alkyl)$_2$;
$R_{Z,Y}^5$ in each case is an optionally substituted $C_1$-$C_6$ alkyl, or
aryl or hetaryl, which in each case is optionally singly, doubly, or triply substituted with substituents independently selected from halogen, $NH_2$, CN, $CF_3$, $CHF_2$, $OCF_3$, $OCHF_2$, $NH-(C_1$-$C_6$ alkyl), or $N(C_1$-$C_6$ alkyl)$_2$, or optionally substituted $C_1$-$C_6$ alkyl, or in each case optionally substituted
$O-R_A^1$, $NR_A^2 R_A^3$, $SO_2 NH_2$, $SO_2-R_A^1$, $NR_A^4-SO_2-R_A^1$, or $SO_2-NR_A^2 R_A^3$;
$R_{Z,Y}^6$ is hydrogen, or
in each case optionally substituted $C_1$-$C_6$ alkyl, aryl, $C_1$-$C_4$ alkylene-aryl, $C_1$-$C_4$ alkylene-hetaryl, $SO_2-C_1$-$C_6$ alkyl, $SO_2$-aryl, $SO_2$-hetaryl, or $SO_2-C_1$-$C_4$ alkylene-aryl;
$R_{Z,Y}^7$ is hydrogen or in each case optionally substituted $C_1$-$C_6$ alkyl;
or the radicals $R_{Z,Y}^6$ and $R_{Z,Y}^7$ together with the nitrogen form a 3- to 7-membered saturated or aromatic heterocycle which is optionally substituted in each case and which may contain one, two, or three further heteroatoms, which may be different or the same, selected from the group comprising O, N, and S;
4.) A 5- or 6-membered aromatic heterocycle which may contain one, two, or three heteroatoms, which may be different or the same, selected from the group comprising O, N, and S, and which in each case may be substituted with a substituent selected from the group consisting of $R_{Z,Y}^1$, $R_{Z,Y}^2$, and $R_{Z,Y}^3$, as defined above;
5.) Optionally substituted adamantyl.

16. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, $R_Q^1, R_Q^2, R_Q^3, R_Q^4, V_Q, R_Q^5, R_Q^{5*}, R_Q^6, R_Q^7, R_4, R_5, R_6, R_7, R_{Z,Y}^1, R_{Z,Y}^2, R_{Z,Y}^3, R_{Z,Y}^4, R_{Z,Y}^5, R_{Z,Y}^6, R_{Z,Y}^7$, and $R_{Z,Y}^8$, unless stated otherwise below, have the same meaning stated in claim 1, and the radicals below have the following definitions:

A: is $NH_2$, $OCF_3$, $OCHF_2$, COOH, $O-CH_2-COOH$, SH, or in each case optionally substituted $O-C_1$-$C_6$ alkyl, $S-C_1$-$C_6$ alkyl, $C_1$-$C_6$ alkyl, or in each case optionally substituted
$O-R_A^1$, $CO-R_A^1$, $S-R_A^1$, $O-CH_2-COO-R_A^1$, $NR_A^2 R_A^3$, $CONH_2$, $SO_2 NH_2$, $SO_2-R_A^1$, $NR_A^4-SO_2-R_A^1$, $SO_2-NRA^2 R_A^3$, or $CO-NR_A^2 R_A^3$;
wherein
$R_A^1$: is in each case optionally substituted $C_1$-$C_6$ alkyl, $C_3$-$C_7$ cycloalkyl, phenyl, or benzyl;
$R_A^2$; $R_A^3$ independently stand for
hydrogen, or
in each case optionally substituted $C_1$-$C_6$ alkyl, phenyl, benzyl, phenethyl, $CO-C_1$-$C_6$ alkyl, CO-aryl, $CO-O-C_1$-$C_6$ alkyl, $SO_2-C_1$-$C_6$ alkyl, $SO_2$-aryl, $SO_2$-hetaryl, or $SO_2-C_1$-$C_4$ alkylene-aryl;
or both radicals $R_A^2$ and $R_A^3$ together with the nitrogen form a 5- or 6-membered saturated or aromatic ring which is optionally substituted in each case, and which may contain one or two further heteroatoms, which may be the same or different, selected from the group comprising O and N;
$R_A^4$: is hydrogen or an optionally substituted $C_1$-$C_6$ alkyl radical;
B: is hydrogen, halogen, CN, $CF_3$, $-CHF_2$, $OCF_3$, $OCHF_2$, or in each case optionally substituted $C_1$-$C_6$ alkyl or $C_2$-$C_6$ alkenyl, or in each case optionally substituted $-O-CH_2-COO-R_A^1$, $-O-R_A^1$, $S-R_A^1$, $NR_A^2 R_A^3$, $-NR_A^4-CO-R_A^1$, or $-CO-NRA^2 R_A^3$; $NRA^4-SO_2-R_A^1$;
or B together with $R_w^1$ forms one of the radicals $-(CH_2)_3-$, $-O-CH_2-O-$, $-O-(CH_2)_2-O-$, $-CH=CH-CH=CH-$, $-O-(CH_2)_2-$, or $-(CH_2)_2-O-$;
$R_w^1$: is hydrogen, F, Cl, CN, $CF_3$, $O-CF_3$, or
in each case optionally substituted $C_1$-$C_6$ alkyl, aryl, $C_1$-$C_6$ alkylamino, or $C_1$-$C_6$ dialkylamino;
Q: in formula Q1 is the sum of a, b, and c, which is equal to 1, 2, or 3;
$R_Q^1, R_Q^2, R_Q^3, R_Q^4$ independently stand for:
hydrogen, halogen, OH, or optionally substituted $C_1$-$C_6$ alkyl;
$V_Q$: is $-CO-$, $-CO-NR_Q^5-$, $-NR_Q^5-CO-$, $-O-$, or $-S-$;
$R_Q^5$: is hydrogen, or $CH_3$;
$R^1, R^2$ independently stand for:
hydrogen, OH, CN, or in each case optionally substituted $C_1$-$C_6$ alkyl, $C_1$-$C_6$ alkylene-$O-C_1$-$C_6$ alkyl, substituted aryl, benzyl, $CO-C_1$-$C_6$ alkyl, CO-aryl, or $CO-C_1$-$C_4$ alkylene-aryl;
$R^3$ is a free electron pair or hydrogen;
X, Y Z X=N, Y=$CR^4$, Z=$CR^6$, or
X=C, Y=$CR^4$, Z=$NR^7$, or
X=N, Y=N, Z=$CR^6$;
$R^4, R^6$ in each case independently stand for a radical, selected from groups 1.), 3.), 4.), and 5.), which may be the same or different, and
$R^5, R^7$ in each case independently stand for a radical selected from groups 2.), 3.), 4.), and 5.), which may be the same or different, wherein groups 1.) through 5.) have the following meanings:
1.) Hydrogen, CN, $CF_3$, $CHF_2$, $O-CH_2-COON$, halogen, or in each case optionally substituted $C_1$-$C_{10}$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, or $C_1$-$C_4$ alkylene-hetaryl, or in each case optionally substituted O—$R_{Z,Y}^4$, $NR_{Z,Y}^6R_{Z,Y}^7$, CO—$OR_{Z,Y}^5$, $NR_{Z,Y}^7$—CO—O—$R_{Z,Y}^5$, O—$CH_2$—COO—$R_{Z,Y}^7$, $NR_{Z,Y}^7$—CO—$R_{Z,Y}^5$, $SO_2$—$R_{Z,Y}^5$, $NR_{Z,Y}^7$—$SO_2$—$R_{Z,Y}^5$, $SO_2NH_2$, $CONH_2$, $SO_2$—$NR_{Z,Y}^6R_{Z,Y}^7$, or CO—$NR_{Z,Y}^6R_{Z,Y}^7$;

2.) A free electron pair or hydrogen,
in each case optionally substituted $C_1$-$C_{10}$ alkyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, COO—$C_1$-$C_6$ alkyl, or SO—$R_{Z,Y}^5$, $SO_2NH_2$, $CONH_2$, or in each case optionally substituted $SO_2$—$NR_{Z,Y}^6R_{Z,Y}^7$, or CO—$NR_{Z,Y}^6R_{Z,Y}^7$;

3.) Phenyl, 1-naphthyl, or 2-naphthyl, which in each case are or may be substituted with a substituent selected from the group consisting of $R_{Z,Y}^1$, $R_{Z,Y}^2$, and $R_{Z,Y}^3$, wherein $R_{Z,Y}^1$, $R_{Z,Y}^2$, and $R_{Z,Y}^3$ in each case independently represent a substituent selected from the following group:
Hydrogen, $NH_2$, CN, $CF_3$, $CHF_2$, $OCF_3$, $OCHF_2$, O—$CH_2$—COON, halogen, or
in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted
O—$R_{Z,Y}^4$, S—$R_{Z,Y}^4$, $NR_{Z,Y}^6R_{Z,Y}^7$, $R_{Z,Y}^7$—CO—$OR_{Z,Y}^5$, $NR_{Z,Y}^7$—CO—$R_{Z,Y}^5$, $SO_2$—$R_{Z,Y}^5$, $NR_{Z,Y}^7$—$SO_2$—$R_{Z,Y}^5$, $SO_2NH_2$, $SO_2$—$NR_{Z,Y}^6R_{Z,Y}^7$, $CO_2NH_2$, or CO—$NR_{Z,Y}^6R_{Z,Y}^7$, or
in each case two of the radicals from $R_{Z,Y}^1$, $R_{Z,Y}^2$, or $R_{Z,Y}^3$ form, together with the ring atoms bearing these substituents, a 3- to 7-membered saturated or unsaturated carbocycle which in each case is optionally substituted, or a saturated or unsaturated heterocycle which in each case is optionally substituted and which may contain one, two, or three further heteroatoms, which may be different or the same, selected from the group comprising O, N, and S;

$R_{Z,Y}^4$ is in each case optionally substituted $C_1$-$C_4$ alkylene-$C_3$-$C_7$ cycloalkyl, $C_1$-$C_4$ alkylene-heterocycloalkyl, heterocycloalkyl, hetaryl, aryl, $C_1$-$C_4$ alkylene-hetaryl, hetaryl, $C_1$-$C_4$ alkylene-aryl, or
$C_1$-$C_6$ alkyl which in each case is optionally substituted with a substituent selected from the group comprising halogen, $NO_2$, $NH_2$, OH, CN, $CF_3$, $CHF_2$, $OCF_3$, $OCHF_2$, optionally substituted NH—($C_1$-$C_6$ alkyl), and optionally substituted N($C_1$-$C_6$ alkyl)$_2$;

$R_{Z,Y}^5$ is in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, heterocycloalkyl, or $C_1$-$C_6$ alkylene-O—$C_1$-$C_6$ alkyl, or dioxymethylenephenyl, or aryl or hetaryl which in each case is optionally singly, doubly, or triply substituted with substituents independently selected from halogen, $NO_2$, $NH_2$, OH, CN, $CF_3$, $CHF_2$, $OCF_3$, $OCHF_2$, optionally substituted NH—($C_1$-$C_6$ alkyl), or optionally substituted N($C_1$-$C_6$ alkyl)$_2$, COOH, O—$CH_2$—COOH, SH, or
optionally substituted $C_1$-$C_6$ alkyl, $C_3$-$C_7$ cycloalkyl, aryl, hetaryl, heterocycloalkyl, or
O—$R_A^1$, S—$R_A^1$, $NR_A^4$—CO—O—$R_A^1$, O—$CH_2$—COO—$R_A^1$, $NR_A^2R_A^3$, $CONH_2$, $SO_2NH_2$, SO—$R_A^1$, $NR_A^4$—$SO_2$—$R_A^1$, or $SO_2$—$NR_A^2R_A^3$;

$R_{Z,Y}^6$ is hydrogen, or
in each case optionally substituted $C_1$-$C_6$ alkyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, $C_1$-$C_4$ alkylene-aryl, $C_1$-$C_4$ alkylene-hetaryl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, CO—O—$C_1$-$C_4$ alkylene-aryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$R_{Z,Y}^7$ is hydrogen or in each case optionally substituted $C_1$-$C_6$ alkyl;
or the radicals $R_{Z,Y}^6$ and $R_{Z,Y}^7$ together with the nitrogen form a 3- to 7-membered saturated or aromatic heterocycle which is optionally substituted in each case and which may contain one, two, or three further heteroatoms, which may be different or the same, selected from the group comprising O, N, and S;

4.) A 5- or 6-membered aromatic heterocycle which may contain one, two, or three heteroatoms, which may be different or the same, selected from the group comprising O, N, and S, and which in each case may be substituted with a substituent selected from the group consisting of $R_{Z,Y}^1$, $R_{Z,Y}^2$, and $R_{Z,Y}^3$, as defined above;

5.) A $C_5$-$C_{10}$ bi- or tricyclic saturated hydrocarbon radical which is optionally substituted in each case.

17. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, A, $R_A^1$, $R_A^2$, $R_A^3$, $R_A^4$, B, $R_w^1$, Q, a, b, c, $R_a^1$, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, X, Y, and Z, unless stated otherwise below, have the same meaning stated in claim 1, and the radicals below have the following definitions:

A: is F, Cl, $OCF_3$, $OCHF_2$, in each case optionally substituted $C_1$-$C_6$ alkyl, O—$C_1$-$C_6$ alkyl, S—$C_1$-$C_6$ alkyl, or optionally substituted $OR_A'$;

$R_A^1$: is in each case optionally substituted $C_1$-$C_6$ alkyl or phenyl;

B: is hydrogen, F, Cl, $CF_3$, $OCF_3$, $OCHF_2$, or in each case optionally substituted $C_1$-$C_6$ alkyl, O—$C_1$-$C_6$ alkyl, or S—$C_1$-$C_6$ alkyl;

$R_w^1$: is hydrogen, F, Cl, CN, $CF_3$, or O—$CF_3$;

Q: is —$CR_Q^1R_Q^2$;

$R_Q^1$, $R_Q^2$ in each case independently stand for hydrogen, F, or $CH_3$;

$R^1$, $R^2$ independently stand for:
hydrogen, OH, CN, O-methyl, O-phenyl, acetyl, benzoyl, O-acetyl, or O-benzoyl;

$R^3$ is a free electron pair or hydrogen;

X, Y, Z X=N, Y=$CR^4$, Z=$CR^6$, or
X=N, Y=N, Z=$CR^6$;

$R^4$, $R^6$ in each case independently stand for a radical, selected from groups 1.), 3.), 4.), and 5.), which may be the same or different, and $R^5$ is a radical selected from groups 2.) and 3.), which may be the same or different, wherein groups 1.) through 5.) have the following meanings:

1.) Hydrogen, CN, $CF_3$, $CHF_2$, O—$CH_2$—COOH, halogen, or in each case optionally substituted $C_1$-$C_{10}$ alkyl, $C_2$-$C_{10}$ alkenyl, $C_2$-$C_{10}$ alkynyl, $C_3$-$C_7$ cycloalkyl, $C_1$-$C_6$ alkylene-$C_3$-$C_7$ cycloalkyl, $C_1$-$C_4$ alkylene-aryl, or $C_1$-$C_4$ alkylene-hetaryl, or in each case optionally substituted O—$R_{Z,Y}^4$, $NR_{Z,Y}^6R_{Z,Y}^7$, CO—$OR_{Z,Y}^6$, $NR_{Z,Y}^7$, —CO—O—$R_{Z,Y}^6$, O—$CH_2$—COO—$R_{Z,Y}^5$, $NR_{Z,Y}^7$—CO—$R_{Z,Y}^6$, $SO_2$—$R_{Z,Y}^5$, $NR_{Z,Y}^7$—$SO_2$—$R_{Z,Y}^5$, $SO_2NH_2$, $CONH_2$, $SO_2$—$NR_{Z,Y}^6R_{Z,Y}^7$, or CO—$NR_{Z,Y}^6R_{Z,Y}^7$;

2.) A free electron pair or hydrogen,
   in each case optionally substituted $C_1$-$C_{10}$ alkyl, $C_3$-$C_7$ cycloalkyl, $C_1$-$C_6$ alkylene-$C_3$-$C_7$ cycloalkyl, $C_1$-$C_4$ alkylene-aryl, $C_1$-$C_4$ alkylene-hetaryl, COO—$C_1$-$C_4$ alkyl, or SO—$R_{Z,Y}^5$, $SO_2NH_2$, $CONH_2$, optionally substituted $SO_2$—$NR_{Z,Y}^6R_{Z,Y}^7$, or optionally substituted CO—$NR_{Z,Y}^6R_{Z,Y}^7$;

3.) Phenyl, 1-naphthyl, or 2-naphthyl, which in each case may be substituted with $R_{Z,Y}^1$, $R_{Z,Y}^2$, and $R_{Z,Y}^3$, wherein $R_{Z,Y}^1$, $R_{Z,Y}^2$, and $R_{Z,Y}^3$ in each case independently represent a substituent from the following group:
   Hydrogen, $NH_2$, CN, $CF_3$, $CHF_2$, $OCF_3$, $OCHF_2$, O—$CH_2$—COOH, halogen, or
   in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl, or $C_1$-$C_4$ alkylene-hetaryl, or in each case optionally substituted
   O—$R_{Z,Y}^4$, S—$R_{Z,Y}^4$, $N_{Z,Y}^6R_{Z,Y}^7$, $NR_4Y^6R_{Z,Y}^7$—CO—$OR_{Z,Y}^5$, $NR_{Z,Y}^7$—CO—$R_{Z,Y}^5$, $SO_2$—$R_{Z,Y}^5$, $NR_{Z,Y}^7$—$SO_2$—$R_{Z,Y}^5$, $SO_2NH_2$, $SO_2$—$NR_{Z,Y}^6R_{Z,Y}^7$, or CO—$NR_{Z,Y}^6R_{Z,Y}^7$, or
   in each case two of the radicals from $R_{Z,Y}^1$, $R_{Z,Y}^2$, or $R_{Z,Y}^3$ form, together with the ring atoms bearing these substituents, a 3- to 7-membered saturated or unsaturated carbocycle which in each case is optionally substituted, or a saturated or unsaturated heterocycle which in each case is optionally substituted and which may contain one, two, or three further heteroatoms selected from the group comprising O, N, and S;

$R_{Z,Y}^4$ in each case is an optionally substituted $C_1$-$C_4$ alkylene-$C_3$-$C_7$ cycloalkyl, $C_1$-$C_4$ alkylene-heterocycloalkyl, heterocycloalkyl, hetaryl, aryl, $C_1$-$C_4$ alkylene-hetaryl, hetaryl, $C_1$-$C_4$ alkylene-aryl, or
   $C_1$-$C_6$ alkyl which in each case is optionally substituted with a substituent selected from the group comprising halogen, $NO_2$, $NH_2$, OH, CN, $CF_3$, $CHF_2$, $OCF_3$, $OCHF_2$, optionally substituted NH—($C_1$-$C_6$ alkyl), and optionally substituted N($C_1$-$C_6$ alkyl)$_2$;

$R_{Z,Y}^5$ is in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, heterocycloalkyl, or $C_1$-$C_6$ alkylene-O—$C_1$-$C_6$ alkyl,
   or dioxymethylenephenyl, or aryl or hetaryl which in each case is optionally singly, doubly, or triply substituted with substituents independently selected from halogen, $NO_2$, $NH_2$, OH, CN, $CF_3$, $CHF_2$, $OCF_3$, $OCHF_2$, optionally substituted NH—($C_1$-$C_6$ alkyl),
   optionally substituted N($C_1$-$C_6$ alkyl)$_2$, COOH, O—$CH_2$—COOH, or SH, or in each case optionally substituted $C_1$-$C_6$ alkyl, $C_3$-$C_7$ cycloalkyl, aryl, hetaryl, or heterocycloalkyl, or in each case optionally substituted
   O—$R_A^1$, S—$R_A^1$, $NR_A^4$—CO—O—$R_A^1$, O—$CH_2$—COO—$R_A^1$, $NR_A^2R_A^3$, $CONH_2$, $SO_2NH_2$, $SO_2$—$R_A^1$, $NR_A^4$—$SO_2$—$R_A^1$, or $SO_2$—$NR_A^2R_A^3$;

$R_{Z,Y}^6$ is hydrogen, or
   in each case optionally substituted $C_1$-$C_6$ alkyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, $C_1$-$C_4$ alkylene-aryl, $C_1$-$C_4$ alkylene-hetaryl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, CO—O—$C_1$-$C_4$ alkylene-aryl, $SO_2$—$C_1$-$C_6$ alkyl, $SO_2$-aryl, $SO_2$-hetaryl, $SO_2$—$C_1$-$C_4$ alkylene-aryl, or $SO_2$—$C_1$-$C_4$ alkylene-hetaryl;

$R_{Z,Y}^7$ is hydrogen or optionally substituted $C_1$-$C_6$ alkyl;
   or the radicals $R_{Z,Y}^6$ and $R_{Z,Y}^7$ together with the nitrogen form a 3- to 7-membered saturated or aromatic heterocycle which is optionally substituted in each case and which may contain one, two, or three further heteroatoms, which may be different or the same, selected from the group comprising O, N, and S;

4.) A 5- or 6-membered aromatic heterocycle which may contain one, two, or three heteroatoms, which may be different or the same, selected from the group comprising O, N, and S, and which in each case may be substituted with a substituent selected from the group consisting of $R_{Z,Y}^1$, $R_{Z,Y}^2$, and $R_{Z,Y}^3$, as defined above;

5.) Optionally substituted adamantyl.

18. A 5-ring heteroaromatic compound of general formula I according to claim 1, and/or corresponding enantiomeric, diastereomeric, and/or tautomeric forms thereof, and/or pharmaceutically acceptable salts thereof, wherein the radicals W, A, $R_A^1$, $R_A^2$, $R_A^3$, $R_A^4$, B, $R_w^1$, Q, a, b, c, $R_Q^1$, $R_Q^2$, $R_Q^3$, $R_Q^4$, $V_Q$, $R_Q^5$, $R_Q^{5*}$, $R_Q^6$, $R_Q^7$, $R_1$, $R_2$, $R_3$, X, Y, and Z, unless stated otherwise below, have the same meaning stated in claim 1, and the radicals below have the following definitions:
   A: is $OCF_3$, $OCHF_2$, $OCH_3$, methyl, O-ethyl, O-propyl, or O-isopropyl;
   B: is hydrogen, F, Cl, $CF_3$, $OCF_3$, $OCHF_2$, optionally substituted $C_1$-$C_6$ alkyl, or optionally substituted O—$C_1$-$C_6$ alkyl;
   $R_w^1$: is hydrogen, F, or Cl;
   Q: is —$CH_2$—;
   $R^1$, $R^2$ are hydrogen;
   $R^3$ is a free electron pair or hydrogen;
   X is N;
   Y is $CR^4$;
   Z is $CR^6$;
   $R^4$, $R^6$ in each case independently stand for a radical, selected from groups 1.), 2.), and 3.) which may be the same or different, wherein groups 1.) through 3.) mean the following:
   1.) Hydrogen, $CF_3$, $CHF_2$, or in each case optionally substituted $C_1$-$C_{10}$ alkyl; or
   2.) Phenyl, 1-naphthyl, or 2-naphthyl, which in each case are substituted with a substituent selected from the group consisting of $R_{Z,Y}^1$, $R_{Z,Y}^2$, and $R_{Z,Y}^3$, wherein $R_{Z,Y}^1$, $R_{Z,Y}^2$, and $R_{Z,Y}^3$ in each case independently represent a substituent from the following group:
   Hydrogen, CN, $CF_3$, $CHF_2$, $OCF_3$, $OCHF_2$, O—$CH_2$—COON, halogen, or
   in each case optionally substituted $C_1$-$C_6$ alkyl, aryl, or in each case optionally substituted O—$R_{Z,Y}^4$, $NR_{Z,Y}^6R_{Z,Y}^7$, $NR_{Z,Y}^7$—$SO_2$—$R_{Z,Y}^6$, or
   in each case two of the radicals selected from the group comprising $R_{Z,Y}^1$, $R_{Z,Y}^2$, and $R_{Z,Y}^3$ together form one of the radicals
   —O—$CH_2$—O—, —O—$CH_2$—$CH_2$—O—, —O—$CH_2$—$CH_2$—, or —$CH_2$—$CH_2$—$CH_2$—;

$R_{Z,Y}^4$ is in each case optionally substituted hetaryl, aryl, or $C_1$-$C_6$ alkyl;

$R_{Z,Y}^5$ is in each case optionally substituted $C_1$-$C_6$ alkyl, or aryl or hetaryl which in each case is optionally singly, doubly, or triply substituted with substituents independently selected from halogen, $NH_2$, CN, $CF_3$, $CHF_2$, $OCF_3$, $OCHF_2$, or optionally substituted NH—($C_1$-$C_6$ alkyl), or in each case optionally substituted N($C_1$-$C_6$ alkyl)$_2$, or optionally substituted $C_1$-$C_6$ alkyl, or optionally substituted O—$R_A^1$, $NR_A^2R_A^3$, $SO_2NH_2$, $SO_2$—$R_A^1$, $NR_A^4$—$SO_2$—$R_A^1$, or $SO_2$—$NR_A^2R_A^3$;

$R_{Z,Y}^6$ is hydrogen, or
in each case optionally substituted $C_1$-$C_6$ alkyl, aryl, $SO_2$—$C_1$-$C_6$ alkyl; $SO_2$-aryl;

$R_{Z,Y}^7$ is hydrogen or optionally substituted $C_1$-$C_6$ alkyl

3.) Benzothiophenyl, benzofuranyl, quinolinyl, isoquinolinyl, thienyl, furanyl, pyridinyl, pyrimidinyl, or thiazolyl, which in each case may be substituted with a substituent selected from the group consisting of $R_{Z,Y}^1$, $R_{Z,Y}^2$, and $R_{Z,Y}^3$.

19. A pharmaceutical composition containing at least one 5-ring heteroaromatic compound of general formula I according to claim 1, and/or corresponding enantiomeric, diastereomeric, and/or tautomeric forms thereof, and/or pharmaceutically acceptable salts thereof, and optionally at least one pharmaceutically acceptable carrier and/or diluent.

20. A 5-ring heteroaromatic compound of general formula I according to claim 1, and/or corresponding enantiomeric, diastereomeric, and/or tautomeric forms thereof, and/or pharmaceutically acceptable salts thereof, wherein $R_W^1$ or B is not an optionally substituted N-pyrrolidinyl radical in the 4-position (para position) with respect to the coupling position with Q.

21. A 5-ring heteroaromatic compound of general formula I according to claim 1, and/or corresponding enantiomeric, diastereomeric, and/or tautomeric forms thereof, and/or pharmaceutically acceptable salts thereof, wherein $R^4$ and $R^6$ together with X and Y form a benzo radical, which may be substituted with one, two, or three radicals which are independently selected from $R_{Z,Y}^8$.

22. A 5-ring heteroaromatic compound of general formula I according to claim 1, and/or corresponding enantiomeric, diastereomeric, and/or tautomeric forms thereof, and/or pharmaceutically acceptable salts thereof, comprising one, two, or three of the conditions selected from (i), (ii), and (iii):

(i) $R^4$ and $R^6$ together with X and Y form, optionally substituted in each case, a $C_6$-$C_{10}$-membered saturated, unsaturated, or aromatic carbocycle, which may be substituted in each case with one, two, or three radicals which in each case are independently selected from $R_{Z,Y}^8$;

wherein

A is located in W1 in the 2-position as indicated and stands for $NH_2$, $OCF_3$, $OCHF_2$, O—$CH_2$—COOH, O—$C_1$-$C_6$ alkyl, S—$C_1$-$C_6$ alkyl, or O—$R_A^1$, CO—$R_A^1$, S—$R_A^1$, SO—$R_A^1$, $SO_2$—$R_A^1$, or $SO_2$—$NR_A^2R_A^3$;

B is located in W1 in the 6-position and stands for halogen, CN, $CF_3$, —$CHF_2$, $OCF_3$, $OCHF_2$, or in each case optionally substituted $C_1$-$C_6$ alkyl or $C_2$-$C_6$ alkenyl, —O—$CH_2$—COO—$R_A^1$, —O—$R_A^1$, S—$R_A^1$, $NR_A^2R_A^3$, —$NR_A^4$—CO—$R_A^1$, or —CO—$NR_A^2R_A^3$; $NR_A^4$—$SO_2$—$R_A^1$; or B together with $R_Q^1$ forms one of the radicals —$(CH_2)_3$—, —O—$CH_2$—O—, —O—$(CH_2)_2$—O—, —CH=CH—CH=CH—, —O—$(CH_2)_2$—, or —$(CH_2)_2$—O—;

Q is —$CR_Q^1R_Q^2$—;

$R_Q^1$, $R_Q^2$ independently stand for:
hydrogen, halogen, or optionally substituted $C_1$-$C_6$ alkyl;

ii) $R_W^1$ or B is not an optionally substituted N-pyrrolidinyl radical in the 4-position (para position) with respect to the coupling position with Q;

(iii) the sum of a, b, and c is 1, 2, 3, 4, or 5 when X=N, Y=$CR^4$, and Z=$CR^6$.

23. The compound of claim 1, and/or corresponding enantiomeric, diastereomeric, and/or tautomeric forms thereof, and/or pharmaceutically acceptable salts thereof, selected from the group consisting of:

4-(4-Bromophenyl)-1-(2-methoxybenzyl)-1H-imidazole-2-ylamine;
1-(2-Methoxybenzyl)-4-(4-nitrophenyl)-1H-imidazole-2-ylamine;
5-(2-Methoxybenzyl)-2-phenyl-3H-imidazole-4-ylamine;
4-(2-Methoxybenzyl)-1-phenyl-1H-pyrazole-3-ylamine;
2-(2-Methoxybenzyl)-5-phenyl-4H-[1,2,4]triazole-3-ylamine;
4-(2-Methoxybenzyl)-1-(4-methoxyphenyl)-1H-pyrazole-3-ylamine;
1-(4-Fluorophenyl)-4-(2-methoxybenzyl)-1H-pyrazole-3-ylamine;
1-(2,6-Dimethoxybenzyl)-4-phenyl-1H-imidazole-2-ylamine hydrochloride;
N-[1-(2-Methoxybenzyl)-4-phenyl-1H-imidazole-2-yl]acetamide;
1-(2-Methoxybenzyl)-4-phenyl-1H-imidazole-2-ylamine hydrochloride;
4-tert-Butyl-1-(2-methoxybenzyl)-1H-imidazole-2-ylamine;
4-(4-Fluorophenyl)-1-(2-methoxybenzyl)-1H-imidazole-2-ylamine;
1-(2-Methoxybenzyl)-4-thiophene-2-yl-1H-imidazole-2-ylamine;
1-(2-Methoxybenzyl)-5-methyl-4-phenyl-1H-imidazole-2-ylamine;
4-Furan-2-yl-1-(2-methoxybenzyl)-1H-imidazole-2-ylamine hydrochloride;
1-(2-Methoxybenzyl)-4-naphthalene-2-yl-1H-imidazole-2-ylamine hydrochloride;
4-Benzo[b]thiophene-3-yl-1-(2-methoxybenzyl)-1H-imidazole-2-ylamine hydrochloride;
1-(2,6-Dimethoxybenzyl)-4-(4-fluorophenyl)-1H-imidazole-2-ylamine;
1-(2,6-Dimethoxybenzyl)-4-thiophene-2-yl-1H-imidazole-2-ylamine;
1-(2-Methoxybenzyl)-4-thiophene-3-yl-1H-imidazole-2-ylamine hydrochloride;
2-Amino-1-(2-methoxybenzyl)-1H-imidazole-4-carboxylic acid ethyl ester;
1-(2-Methoxybenzyl)-4-(4-trifluoromethoxyphenyl)-1H-imidazole-2-ylamine
1-(2-Methoxybenzyl)-4-(3-methoxyphenyl)-1H-imidazole-2-ylamine;
4-Adamantane-1-yl-1-(2-methoxybenzyl)-1H-imidazole-2-ylamine;
4-[2-Amino-1-(2,6-dimethoxybenzyl)-1H-imidazole-4-yl]benzonitrile hydrochloride;
1-(2,6-Dimethoxybenzyl)-4-(2-methoxyphenyl)-1H-imidazole-2-ylamine hydrochloride;
1-(2-Methoxybenzyl)-4-p-tolyl-1H-imidazole-2-ylamine;
1-(2-Chloro-6-methoxybenzyl)-4-thiophene-3-yl-1H-imidazole-2-ylamine;
1-(2-Chloro-6-methoxybenzyl)-4-(4-trifluoromethoxyphenyl)-1H-imidazole-2-ylamine;

5-[2-Amino-1-(2-methoxybenzyl)-1H-imidazole-4-yl]
isoxazole-3-carboxylic acid ethyl ester;
1-(2-Fluoro-6-methoxybenzyl)-4-thiophene-3-yl-1H-imidazole-2-ylamine;
1-(2-Chloro-6-methoxybenzyl)-4-(4-methoxyphenyl)-1H-imidazole-2-ylamine;
4-[2-Amino-1-(2-fluoro-6-methoxybenzyl)-1H-imidazole-4-yl]benzonitrile;
1-(2-Chloro-6-methoxybenzyl)-4-(4-chlorophenyl)-1H-imidazole-2-ylamine;
4-(2,4-Dichlorophenyl)-1-(2-methoxybenzyl)-1H-imidazole-2-ylamine hydrochloride;
1-(2-Methoxybenzyl)-4-(5-methylfuran-2-yl)-1H-imidazole-2-ylamine;
1-(2-Chloro-6-methoxybenzyl)-4-thiophene-2-yl-1H-imidazole-2-ylamine;
1-(2-Methoxybenzyl)-4-(5-methylthiophene-2-yl)-1H-imidazole-2-ylamine;
4-(4-Isopropylphenyl)-1-(2-methoxybenzyl)-1H-imidazole-2-ylamine;
1-(2,6-Dimethoxybenzyl)-4-(3,4-dimethylphenyl)-1H-imidazole-2-ylamine hydrochloride;
5-Benzyl-1-(2-methoxybenzyl)-1H-imidazole-2-ylamine;
4-Benzofuran-2-yl-1-(2-methoxybenzyl)-1H-imidazole-2-ylamine;
1-(2-Methoxybenzyl)-4-naphthalene-1-yl-1H-imidazole-2-ylamine;
1-(2-Methoxybenzyl)-4-(4-phenoxyphenyl)-1H-imidazole-2-ylamine hydrochloride;
1-(2-Methoxybenzyl)-4-(3-nitrophenyl)-1H-imidazole-2-ylamine;
4-(4-Difluoromethoxyphenyl)-1-(2-methoxybenzyl)-1H-imidazole-2-ylamine;
1-(2-Methoxybenzyl)-4-(2-phenylthiazole-4-yl)-1H-imidazole-2-ylamine;
4-(4-Benzyloxyphenyl)-1-(2-methoxybenzyl)-1H-imidazole-2-ylamine;
1-(2-Methoxybenzyl)-4-thiazole-2-yl-1H-imidazole-2-ylamine hydrochloride;
5-[2-Amino-1-(2-methoxybenzyl)-1H-imidazole-4-yl]thiophene-2-carbonitrile;
4-(3-Aminophenyl)-1-(2-methoxybenzyl)-1H-imidazole-2-ylamine;
1-(2,6-Dimethoxybenzyl)-4-(4-methylthiophene-2-yl)-1H-imidazole-2-ylamine;
4-(4-Aminophenyl)-1-(2-methoxybenzyl)-1H-imidazole-2-ylamine hydrochloride;
4-[2-Amino-1-(2-methoxy-4-nitrobenzyl)-1H-imidazole-4-yl]benzonitrile;
N-{3-[2-Amino-1-(2-methoxybenzyl)-1H-imidazole-4-yl]phenyl}-4-isopropylbenzenesulfonamide;
N-{3-[2-Amino-1-(2-methoxybenzyl)-1H-imidazole-4-yl]phenyl}benzenesulfonamide;
N-{3-[2-Amino-1-(2-methoxybenzyl)-1H-imidazole-4-yl]phenyl}methanesulfonamide;
N-{3-[2-Amino-1-(2-methoxybenzyl)-1H-imidazole-4-yl]phenyl}benzamide
N-{4-[2-Amino-1-(2-methoxybenzyl)-1H-imidazole-4-yl]phenyl}benzenesulfonamide;
Thiophene-2-sulfonic acid {3-[2-amino-1-(2-methoxybenzyl)-1H-imidazole-4-yl]phenyl}amide;
1-(2-Methoxybenzyl)-4-pyridine-3-yl-1H-imidazole-2-ylamine;
5-(2-Methoxybenzyl)-2-(4-methoxyphenyl)-3H-imidazole-4-ylamine hydrochloride;
Biphenyl-4-sulfonic acid {3-[2-amino-1-(2-methoxybenzyl)-1H-imidazole-4-yl]phenyl}amide; and
Biphenyl-4-sulfonic acid {3-[2-amino-1-(2-methoxybenzyl)-1H-imidazole-4-yl]phenyl}amide.

* * * * *